US011123380B2

(12) United States Patent
Chang et al.

(10) Patent No.: US 11,123,380 B2
(45) Date of Patent: Sep. 21, 2021

(54) ENGINEERED THERAPEUTIC PROBIOTIC SYSTEM AND METHOD

(71) Applicants: Matthew Wook Chang, Singapore (SG); Chun Loong Ho, Singapore (SG)

(72) Inventors: Matthew Wook Chang, Singapore (SG); Chun Loong Ho, Singapore (SG)

(*) Notice: Subject to any disclaimer, the term of this patent is extended or adjusted under 35 U.S.C. 154(b) by 211 days.

(21) Appl. No.: 16/240,648

(22) Filed: Jan. 4, 2019

(65) Prior Publication Data
US 2019/0209625 A1 Jul. 11, 2019

Related U.S. Application Data

(60) Provisional application No. 62/615,392, filed on Jan. 9, 2018.

(51) Int. Cl.
| | | |
|---|---|---|
| *C12N 1/20* | (2006.01) | |
| *A61K 35/741* | (2015.01) | |
| *C12N 9/24* | (2006.01) | |
| *C12N 15/52* | (2006.01) | |
| *A61P 35/00* | (2006.01) | |

(52) U.S. Cl.
CPC ............ *A61K 35/741* (2013.01); *A61P 35/00* (2018.01); *C12N 9/2402* (2013.01); *C12N 15/52* (2013.01); *C12Y 302/01147* (2013.01)

(58) Field of Classification Search
CPC .................................. C12N 1/20; C12N 15/09
See application file for complete search history.

(56) References Cited

PUBLICATIONS

Knelson et al., "Heparan sulfate signaling in cancer," Cell Press 39(6):277-288, 2014.*
Nastruzzi et al., "In vitro antiproliferative activity of isothiocyanates and nitriles generated by myrosinase-mediated hydrolysis of glucosinolates from seeds of cruciferous vegetables," J Agric Food Chem 48:3572-3575, 2000.*

* cited by examiner

*Primary Examiner* — Rosanne Kosson
(74) *Attorney, Agent, or Firm* — BioInnovation Legal PLLC; James C. Schroeder

(57) ABSTRACT

The claimed invention provides therapeutic as well as protective measures against colorectal cancer by utilizing genetically modified gut bacteria (101) in conjunction with an optimized diet high in cruciferous vegetable intake. According to the claimed system and method, engineered gut bacteria maximize the therapeutic value of the cruciferous vegetable diet to eradicate, offset or prophylactically prevent the onset of colorectal cancer. In the claimed invention gut bacteria *Escherichia coli* bind specifically to the heparan sulphate proteoglycan on colorectal cancer cells to secrete the enzyme myrosinase to transform host-ingested glucosinolates which are natural components of cruciferous vegetables to sulphoraphane, an organic small molecule with known anti-cancer activity.

8 Claims, 35 Drawing Sheets

Specification includes a Sequence Listing.

101

101

103　　　　　　　　　105　　　　　　　　　107

201

203

205

303

305

401

403

405

407

501

503

505

507

509

511

601

603

609

611

613

701

903

905

907

909

911

1001

1401

1501  1503  1505  1507

1601

1603

1701

1703

1801

1803

1901

1903

2201

2301

2401

2501

2601

2701

Figure 30a & 30b Sequence guide key: Myrosinase II (underline), Ice-nucleating protein leader sequence (double underline), Promoter region (bold), YebF secretion tag (italics), Restriction sites (grey background) Histone-like protein A (dashed underline), Double terminator (bold italics), Ribosomal Binding site (dotted underline bold)

Figure 30a
DNA construct

TTTACGGCTAGCTCAGTCCTAGGTACTATGCTAGCAAAAAAAAAGAGGAGAAAAAAAAT
GGCCGATCACTGCGGTCTTATCTGGCCAGCGTCCGGTACTGTGGAATCTCGTTACTGGCAGTC
TACCCGTCGCCATGAGAACGGTCTGGTAGGTTTACTGTGGGTGCTGGCACCAGCGCATTCCT
CAGCGTGCATGCAGATGCTCGTTGGATTGTCTGTGAAGTTGCCGTTGCAGACATCATCAGTC
TGGAAGAGCCGGGTATGGTGAAGTTTCCGCGTGCCGAAGTGGTTCATGTCGGCGACCGTATT
AGCGCGTCTCACTTCATTTCGGCACGTCAGGCCGACCCTGCGTCTACCTCAACTTCTACGTCC
ACGAGTACGCTGACTCCAATGCCTACGGCCATTCCGACGCCAATGCCTGCGGTTGCAAGCGTA
ACGCTGCCAGTGGCAGAACAGGCACGTCATGAAGTGTTTGATGTAGCGTCGGTAAGCGCTGC
TGCCGCACCAGTCAACACTCTGCCAGTTACTACGCCGCAGAATCTGCAGACCGCAACTTATGG
TTCTACGTTGTCCGGCGACAATCATTCTCGTCTGATTGCAGGTTATGGTTCCAACGAGACCGC
TGGCAACCACAGTGATCTGATTGGGTCCTTTGGTACCATGGCGAACAAACAGGATCTGATTG
CGAAAGTGGCGGAAGCGACCGAACTGACCAAAAAGATAGCGCGGCGGCGGTGGATGCGGTG
TTTAGCGCGATTGAAAGTTTTCTGAGCGAAGGCGAAAAGTGCAGCTGATTGGCTTTGGCAA
CTTTGAAGTGCGCGAACGCGCGGCGCGCAAAGGCCGCAACCCGCAGACCGGCGCGGAAATTAA
AATTGCGGCGAGCAAAGTGCCGGCGTTTAAAGCGGGCAAAGCGCTGAAAGATGCGGTGAAAT
AAAAGCTTCCAGGCATCAAATAAAACGAAAGGCTCAGTCGAAAGACTGGGCCTTTCGTTTTA
*TCTGTTGTTTGTCGGTGAACGCTCTCTACTAGAGTCACACTGGCTCACCTTCGGGTGGGCCTT*
*TCTGCGTTTATA*AAAAACTGACAGCTAGCTCAGTCCTAGGTATAATGCTAGCAAAAAAA
AAGAGGAGAAAAAAA*ATGAAAAAAGAGGGGCGTTTTAGGGCTGTTGTTGGTTTCTGCCTG*
*CGCATCAGTTTTCGCTGCCAATAATGAAACCAGCAAGTCGGTCACTTTCCCAAAGTGTGAAGACC*
*TGGATGCTGCCGGAATTGCCGCGAGCGTAAAACGTGATTATCAACAAAATCGCGTGGCGCGTTGG*
*GCAGATGATCAAAAAATTGTCGGTCAGGCCGATCCCGTGGCTTGGGTCAGTTTGCAGGACATTCA*
*GGGTAAAGATGATAAATGGTCAGTACCGCTAACCGTGCGTGGTAAAAGTGCCGATATTCATTACC*
*AGGTCAGCGTGGACTGCAAAGCGGGAATGGCGGAATATCAGCGGCGT*CATATGATGAGCATCCC
AAAAGCTCATTACTCTCTGGCAATCCTGGCTGTACTGTTCGTGGTGTCTAACTCCCAGAACGT
ATGCAACCCGGCCTGCAAGGCGAAAGAACCATTCAACTGTGACAACACTCTGACCTTCAACCA
GACCGGCTTCCCGAAAAACTTTACGTTCGGCGCTGCAACCTCTGCTTACCAGATCGAGGGTGC
TGCTCACCGTGCGCTGAACGGTTGGGATTACTTTACCCATCGTTATCCGGAGAAAGTCCCGGA
CCGTAGCTCCGGTGACCTGGCTTGTGATTCCTATGACCTGTATAAAGATGACGTGAAACTGCT
GAAACGTATGAACGTCCAAGCATACCGTCTGTCTATCGCTTGGAGCCGTGTTCTGCCGAAAG
GCCGTCTGATCGGTGGTGTAGACGAAATGGTATTACCTATTACAACAACCTGATTAACGAA
CTGAAAGCCAACGGCATCGAACCGTACGTTACCATCTTCCACTGGGATGTCCCACAAACCCTG
GAAGACGAATATGGTGGCTTCCTGTCCCCGCGCATCGTTGAGGACTTCACGAACTTTGCAGA
ACTGCTGTTCCAGCGTTTTGGTGATCGTGTTAAGTTCTGGATCACCCTGAACCAGCCGTACTC
CCTGGCCACTAAAGGTTACGGTGACGGCAGCTATCCGCCTGGTCGTTGCACCGATTGTGAATT
CGGCGGCGATTCTGGTACCGAACCGTACATCGTAGCGCATCATCAGCTGCTGGCGCATGCTGA
AACGGTTTCTCTGTACCGTAAACGTTACCAAAAATTCCAAGGCGGTAAAATCGGTACTACCC

Figure 30b

TGATTGGTCGTTGGTTCCAGCCGCTGAACCAGACCTCCAATCTGGACAAAGCTGCAGCCAAAC
GTGCTTTTGATTTCTTCGTTGGTTGGTTCCTGGATCCGCTGGTATACGGTGAGTATCCGAAA
ATCATGAAAGAAATGGTGGGCGATCGCATGCCGAAGTTCACCCCGCAAGAATCTGATCTGGT
GAAAGGTTCTCTGGACTTCCTGGGCCTGAACTATTACGTCACCCAGTACGCGACCGATGCCCC
TCCGTCCATCCCGACCCAGCCGTCTGCTATCACGGACCCGCGCGTTACTCTGGGTTACTATCG
TAACGGCATCCCGATTGGTGTTCAGGCAGCTTCCTTCGTTTATTACCCGACTGGCTTTCGCCA
GATCCTGAATCATATCAAGGACAACTATAAAAACCCGCTGACCTATATTACTGAAAATGGTG
TGGCCGACTTCGGCAATCTGACCCTGGCGAACGCTCTGGCGGATATTGGCCGCATCCAAAACC
ATTGTTCCCATCTGTCTTGCCTGAAATGTGCGATTGCTGACGGCTGCAACGTTGGCGGTTATT
TCGCTTGGAGCTTTATGGATAATTATGAGTTTGGTAACGGCTATACCCTGCGTTTCGGTATG
AACTGGGTTAACTTTACCAACCCTGCAGACCGTAAGCAGAAAGACTCCGGCAAATGGTTTAG
CAAATTTCTGGCTAAATAA*CTCGAG**CCAGGCATCAAATAAAACGAAAGGCTCAGTCGAAAGA*
*CTGGGCCTTTCGTTTTATCTGTTGTTTGTCGGTGAACGCTCTCTACTAGAGTCACACTGGCTC*
*ACCTTCGGGTGGGCCTTTCTGCGTTTATA*

Protein Construct

INP-HlpA

```
1      ATGGCCGATCACTGCGGTCTTATCTGGCCAGCGTCCGGTACTGTGGAATCTCGTTACTGG
1       M  A  D  H  C  G  L  I  W  P  A  S  G  T  V  E  S  R  Y  W    ↑ INP

61     CAGTCTACCCGTCGCCATGAGAACGGTCTGGTAGGTTTACTGTGGGGTGCTGGCACCAGC
21      Q  S  T  R  R  H  E  N  G  L  V  G  L  L  W  G  A  G  T  S

121    GCATTCCTCAGCGTGCATGCAGATGCTCGTTGGATTGTCTGTGAAGTTGCCGTTGCAGAC
41      A  F  L  S  V  H  A  D  A  R  W  I  V  C  E  V  A  V  A  D

181    ATCATCAGTCTGGAAGAGCCGGGTATGGTGAAGTTTCCGCGTGCCGAAGTGGTTCATGTC
61      I  I  S  L  E  E  P  G  M  V  K  F  P  R  A  E  V  V  H  V

241    GGCGACCGTATTAGCGCGTCTCACTTCATTTCGGCACGTCAGGCCGACCCTGCGTCTACC
81      G  D  R  I  S  A  S  H  F  I  S  A  R  Q  A  D  P  A  S  T

301    TCAACTTCTACGTCCACGAGTACGCTGACTCCAATGCCTACGGCCATTCCGACGCCAATG
101     S  T  S  T  S  T  L  T  P  M  P  T  A  I  P  T  P  M

361    CCTGCGGTTGCAAGCGTAACGCTGCCAGTGGCAGAACAGGCACGTCATGAAGTGTTTGAT
121     P  A  V  A  S  V  T  L  P  V  A  E  Q  A  R  H  E  V  F  D

421    GTAGCGTCGGTAAGCGCTGCTGCCGCACCAGTCAACACTCTGCCAGTTACTACGCCGCAG
141     V  A  S  V  S  A  A  A  A  P  V  N  T  L  P  V  T  T  P  Q    | HlpA

481    AATCTGCAGACCGCAACTTATGGTTCTACGTTGTCCGGCGACAATCATTCTCGTCTGATT
161     N  L  Q  T  A  T  Y  G  S  T  L  S  G  D  N  H  S  R  L  I

541    GCAGGTTATGGTTCCAACGAGACCGCTGGCAACCACAGTGATCTGATTGGGTCCTTTGGT
181     A  G  Y  G  S  N  E  T  A  G  N  H  S  D  L  I  G  S  F  G  ↓ KpnI

601    ACCATGGCGAACAAACAGGATCTGATTGCGAAAGTGGCGGAAGCGACCGAACTGACCAAA  ▲
201     T  M  A  N  K  Q  D  L  I  A  K  V  A  E  A  T  E  L  T  K  |

661    AAAGATAGCGCGGCGGCGGTGGATGCGGTGTTTAGCGCGATTGAAAGTTTTCTGAGCGAA
221     K  D  S  A  A  A  V  D  A  V  F  S  A  I  E  S  F  L  S  E

721    GGCGAAAAAGTGCAGCTGATTGGCTTTGGCAACTTTGAAGTGCGCGAACGCGCGGCGCGC
241     G  E  K  V  Q  L  I  G  F  G  N  F  E  V  R  E  R  A  A  R

781    AAAGGCCGCAACCCGCAGACCGGCGCGGAAATTAAAATTGCGGCGAGCAAAGTGCCGGCG
261     K  G  R  N  P  Q  T  G  A  E  I  K  I  A  A  S  K  V  P  A

841    TTTAAAGCGGGCAAAGCGCTGAAAGATGCGGTGAAATAA
281     F  K  A  G  K  A  L  K  D  A  V  K  *                           ▼
```

Figure 32a

YebF-I1

```
1    ATGAAAAAAGAGGGGCGTTTTTAGGGCTGTTGTTGGTTTCTGCCTGCGCATCAGTTTTC
1     M  K  K  R  G  A  F  L  G  L  L  L  V  S  A  C  A  S  V  F

61   GCTGCCAATAATGAAACCAGCAAGTCGGTCACTTTCCCAAAGTGTGAAGACCTGGATGCT
21    A  A  N  N  E  T  S  K  S  V  T  F  P  K  C  E  D  L  D  A

121  GCCGGAATTGCCGCGAGCGTAAAACGTGATTATCAACAAAATCGCGTGGCGCGTTGGGCA
41    A  G  I  A  A  S  V  K  R  D  Y  Q  Q  N  R  V  A  R  W  A

181  GATGATCAAAAAATTGTCGGTCAGGCCGATCCCGTGGCTTGGGTCAGTTTGCAGGACATT
61    D  D  Q  K  I  V  G  Q  A  D  P  V  A  W  V  S  L  Q  D  I

241  CAGGGTAAAGATGATAAATGGTCAGTACCGCTAACCGTGCGTGGTAAAAGTGCCGATATT
81    Q  G  K  D  D  K  W  S  V  P  L  T  V  R  G  K  S  A  D  I

301  CATTACCAGGTCAGCGTGGACTGCAAAGCGGGAATGGCGGAATATCAGCGGCGTCATATG
101   H  Y  Q  V  S  V  D  C  K  A  G  M  A  E  Y  Q  R  R  H  M

361  ATGAGCATCCCAAAAGCTCATTACTCTCTGGCAATCCTGGCTGTACTGTTCGTGGTGTCT
121   M  S  I  P  K  A  H  Y  S  L  A  I  L  A  V  L  F  V  V  S

421  AACTCCCAGAACGTATGCAACCCGGCCTGCAAGGCGAAAGAACCATTCAACTGTGACAAC
141   N  S  Q  N  V  C  N  P  A  C  K  A  K  E  P  F  N  C  D  N

481  ACTCTGACCTTCAACCAGACCGGCTTCCCGAAAAACTTTACGTTCGGCGCTGCAACCTCT
161   T  L  T  F  N  Q  T  G  F  P  K  N  F  T  F  G  A  A  T  S

541  GCTTACCAGATCGAGGGTGCTGCTCACCGTGCGCTGAACGGTTGGGATTACTTTACCCAT
181   A  Y  Q  I  E  G  A  A  H  R  A  L  N  G  W  D  Y  F  T  H

601  CGTTATCCGGAGAAAGTCCCCGGACCGTAGCTCCGGTGACCTGGCTTGTGATTCCTATGAC
201   R  Y  P  E  K  V  P  D  R  S  S  G  D  L  A  C  D  S  Y  D

661  CTGTATAAAGATGACGTGAAACTGCTGAAACGTATGAACGTCCAAGCATACCGTCTGTCT
221   L  Y  K  D  D  V  K  L  L  K  R  M  N  V  Q  A  Y  R  L  S

721  ATCGCTTGGAGCCGTGTTCTGCCGAAAGGCCGTCTGATCGGTGGTGTAGACGAAAATGGT
241   I  A  W  S  R  V  L  P  K  G  R  L  I  G  G  V  D  E  N  G

781  ATTACCTATTACAACAACCTGATTAACGAACTGAAAGCCAACGGCATCGAACCGTACGTT
261   I  T  Y  Y  N  N  L  I  N  E  L  K  A  N  G  I  E  P  Y  V

841  ACCATCTTCCACTGGGATGTCCCACAAACCCTGGAAGACGAATATGGTGGCTTCCTGTCC
281   T  I  F  H  W  D  V  P  Q  T  L  E  D  E  Y  G  G  F  L  S

901  CCGCGCATCGTTGAGGACTTCACGAACTTTGCAGAACTGCTGTTCCAGCGTTTTGGTGAT
301   P  R  I  V  E  D  F  T  N  F  A  E  L  L  F  Q  R  F  G  D

961  CGTGTTAAGTTCTGGATCACCCTGAACCAGCCGTACTCCCTGGCCACTAAAGGTTACGGT
321   R  V  K  F  W  I  T  L  N  Q  P  Y  S  L  A  T  K  G  Y  G

1021 GACGGCAGCTATCCGCCTGGTCGTTGCACCGATTGTGAATTCGGCGGCGATTCTGGTACC
341   D  G  S  Y  P  P  G  R  C  T  D  C  E  F  G  G  D  S  G  T
```

YebF → (spans residues 1–~110), NdeI site at CATATG / H M, I1 → (spans from M121 onward)

Figure 32b

```
1081   GAACCGTACATCGTAGCGCATCATCAGCTGCTGGCGCATGCTGAAACGGTTTCTCTGTAC
 361    E  P  Y  I  V  A  H  H  Q  L  L  A  H  A  E  T  V  S  L  Y

1141   CGTAAACGTTACCAAAAATTCCAAGGCGGTAAAATCGGTACTACCCTGATTGGTCGTTGG
 381    R  K  R  Y  Q  K  F  Q  G  G  K  I  G  T  T  L  I  G  R  W

1201   TTCCAGCCGCTGAACCAGACCTCCAATCTGGACAAAGCTGCAGCCAAACGTGCTTTTGAT
 401    F  Q  P  L  N  Q  T  S  N  L  D  K  A  A  A  K  R  A  F  D

1261   TTCTTCGTTGGTTGGTTCCTGGATCCGCTGGTATACGGTGAGTATCCGAAAATCATGAAA
 421    F  F  V  G  W  F  L  D  P  L  V  Y  G  E  Y  P  K  I  M  K

1321   GAAATGGTGGGCGATCGCATGCCGAAGTTCACCCCGCAAGAATCTGATCTGGTGAAAGGT
 441    E  M  V  G  D  R  M  P  K  F  T  P  Q  E  S  D  L  V  K  G

1381   TCTCTGGACTTCCTGGGCCTGAACTATTACGTCACCCAGTACGCGACCGATGCCCCTCCG
 461    S  L  D  F  L  G  L  N  Y  Y  V  T  Q  Y  A  T  D  A  P  P

1441   TCCATCCCGACCCAGCCGTCTGCTATCACGGACCCGCGCGTTACTCTGGGTTACTATCGT
 481    S  I  P  T  Q  P  S  A  I  T  D  P  R  V  T  L  G  Y  Y  R

1501   AACGGCATCCCGATTGGTGTTCAGGCAGCTTCCTTCGTTTATTACCCGACTGGCTTTCGC
 501    N  G  I  P  I  G  V  Q  A  A  S  F  V  Y  Y  P  T  G  F  R

1561   CAGATCCTGAATCATATCAAGGACAACTATAAAAACCCGCTGACCTATATTACTGAAAAT
 521    Q  I  L  N  H  I  K  D  N  Y  K  N  P  L  T  Y  I  T  E  N

1621   GGTGTGGCCGACTTCGGCAATCTGACCCTGGCGAACGCTCTGGCGGATATTGGCCGCATC
 541    G  V  A  D  F  G  N  L  T  L  A  N  A  L  A  D  I  G  R  I

1681   CAAAACCATTGTTCCCATCTGTCTTGCCTGAAATGTGCGATTGCTGACGGCTGCAACGTT
 561    Q  N  H  C  S  H  L  S  C  L  K  C  A  I  A  D  G  C  N  V

1741   GGCGGTTATTTCGCTTGGAGCTTTATGGATAATTATGAGTTTGGTAACGGCTATACCCTG
 581    G  G  Y  F  A  W  S  F  M  D  N  Y  E  F  G  N  G  Y  T  L

1801   CGTTTCGGTATGAACTGGGTTAACTTTACCAACCCTGCAGACCGTAAGCAGAAAGACTCC
 601    R  F  G  M  N  W  V  N  F  T  N  P  A  D  R  K  Q  K  D  S

1861   GGCAAATGGTTTAGCAAATTTCTGGCTAAATAA
 621    G  K  W  F  S  K  F  L  A  K  *

3201
```

ENGINEERED THERAPEUTIC PROBIOTIC SYSTEM AND METHOD

This patent application claims priority under 35 U.S.C. 119(e) to Provisional U.S. Patent Application 62/615,392 filed Jan. 9, 2018 to Matthew Wook Chang entitled "Engineered Therapeutic Probiotic System and Method".

TECHNICAL FIELD

The claimed invention relates to biomedical administration of engineered probiotic organisms. With greater particularity, the claimed invention addresses prophylactic and therapeutic administration of engineered gut bacteria organisms for prevention, mitigation and eradication of colorectal cancer cells in the gastrointestinal tract.

BACKGROUND ART

Colorectal cancer (CRC) is one of the world's most prevalent forms of cancer that mainly manifests in elderly patients. Due to the invasive nature of colorectal fiber-optic examination procedure, diagnosis is often unduly delayed resulting in an avoidable and unduly high percentage of late stage colorectal cancer diagnosis. Over 60% of the patients are initially diagnosed with advanced colorectal carcinomas (stage II or above), exhibiting increasingly worse prognosis compared with early stage colorectal cancer which is much easier to eradicate using surgery.

Chemoprevention is the use of pharmacologic or natural agents to treat the pre-cancerous condition and to inhibit the initiation of tumorigenesis. Common chemo-preventive agents used to date include non-steroidal anti-inflammatory drugs, folic acid, calcium, vitamin D, and antioxidants, but the effects of these agents are often variable based upon age and genetic composition. Alternatively, chemoprevention can be augmented by the consumption of produce enriched with natural metabolites, such as indoles, quinones, alkaloids, and phenolics.

Naturally occurring chemopreventive metabolites often have low bioavailability and poor host-absorption and as a result require a very high consumption of a particular food class to begin to approach eliciting an effective chemoprevention strategy.

SUMMARY OF INVENTION

Technical Problem

Naturally occurring gut bacteria such as *Escherichia coli* do not adequately guard against or therapeutically mitigate the effects of colorectal cancer. Moreover, many chemopreventive metabolites have to undergo enzymatic conversion from a latent state to a bioactive form. One such class of metabolites is glucosinolate, an isothiocyanate present in cruciferous plants such as broccoli and Brussels sprout. Mammals do not express myrosinase, and the conversion of glucosinolate by the naturally occurring gut microbiota shows a catalytic turnover which is inadequate to elicit anticancer effects. While microbes have been redesigned to eradicate pathogens, alleviate metabolic disorders and detect ailments, in cancer applications the therapeutic efficacy of microbial synthesis of anticancer compounds for drug delivery suffers from the cell density-dependent, undefined dosage of the cell-synthesized drug and the cellular metabolic state. Put simply, cruciferous vegetables on their own are inadequate to therapeutically manage colorectal cancer and naturally occurring gut bacteria neither localize to colorectal cancer locations nor do they therapeutically modify or enhance cruciferous vegetables to aid in the fight against colorectal cancer cells.

Solution to Problem

By engineering gut bacteria to optimize the latent therapeutic potential within cruciferous plants, a new system and method for therapeutically mitigating and preventing colorectal cancer is hereby claimed and disclosed. In the novel system and related method, cruciferous plants provide the cancer killing therapeutic which is unlocked and optimized by the engineered gut bacteria. Unlike traditional pharmaceuticals, therapeutic safety is optimized owing to the healthful benefits of cruciferous plants which do not have overdose considerations during administration. As a mechanism of action, sulforaphane inhibits cancer cells through cellular arrest (G2/M), the upregulation of pro-apoptotic factors (such as caspase 8, p21 p53 and Bax) and the downregulation of anti-apoptotic factors (such as Bcl-2 and Hsp90). The conversion of glucosinolate to sulforaphane requires hydrolysis by the myrosinase enzyme (EC3.2.3.1). The cruciferous vegetable diet leads to prominent chemopreventive efficacy if sufficient myrosinase is supplied and localized to target cancer cells in the gastrointestinal tract.

Towards this objective, a bioengineering strategy of reprogramming commensal microbes to target colorectal cancer cells and to deploy myrosinase to yield sulforaphane obtained from a cruciferous vegetable diet is hereby disclosed and claimed.

Advantageous Effects of Invention

Cancer treatments are often highly invasive, often toxic and extract a high toll upon physical, mental and financial wellbeing.

The claimed invention capitalizes on a normal lifestyle including a cruciferous vegetable diet; the key components of the strategy, such as the precursor and the microbial chassis, are already naturally in place in the gastrointestinal tract, demonstrating the potential to turn a regular diet into a cost-effective and sustainable colorectal cancer chemoprevention and mitigation strategy.

Of greatest importance is the ability to therapeutically mitigate and proactively prevent a highly common form of cancer with minimal side effects with low intrusiveness and ideally greatly reduced patient burdens.

BRIEF DESCRIPTION OF DRAWINGS

The accompanying drawings are included to better illustrate exemplary embodiments of the claimed invention.

FIG. 1(*b*) is a schematic illustration of a gut bacteria modified being therapeutically deployed in the gastrointestinal tract according to the claimed invention.

FIG. 2(*b*) is a functional illustration of myrosinase catalysis of glucosinolate.

FIG. 2(*c*) and FIG. 2(*d*) are graphical illustrations of catalytic efficiency of the claimed invention.

FIG. 30 is an Illustrative Representation of DNA construct Seq. ID No 1.

FIG. 31 Illustrative Representation of Genetic Sequence of Protein Construct INP-HlpA Seq. ID No 2.

FIG. 32 Illustrative Representation of Genetic Sequence of Construct YebF-I1 Seq. ID No 3.

DESCRIPTION OF EMBODIMENTS

Examples

Example 1

Figure 1A:
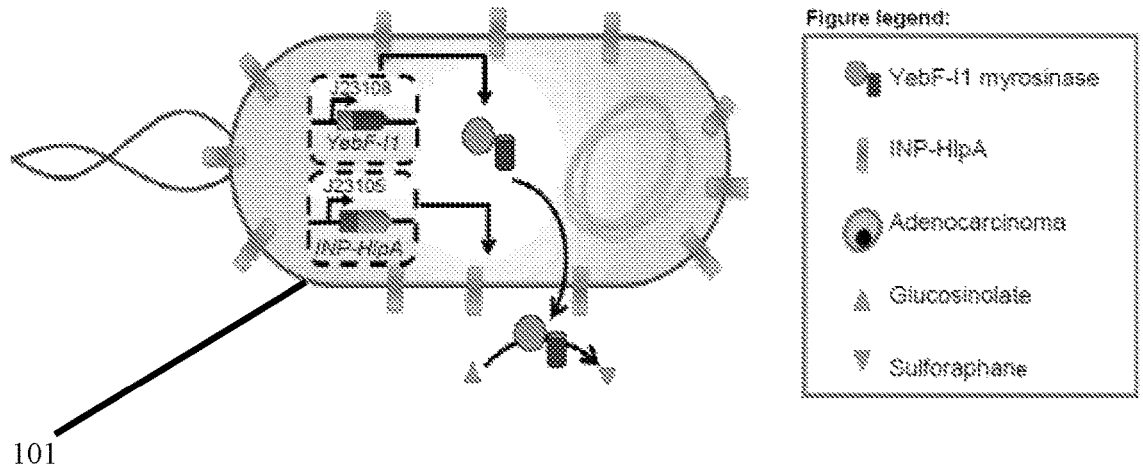
FIG. 1(*a*) is a schematic illustration of a gut bacteria modified according to the claimed invention.
Figure 1B:
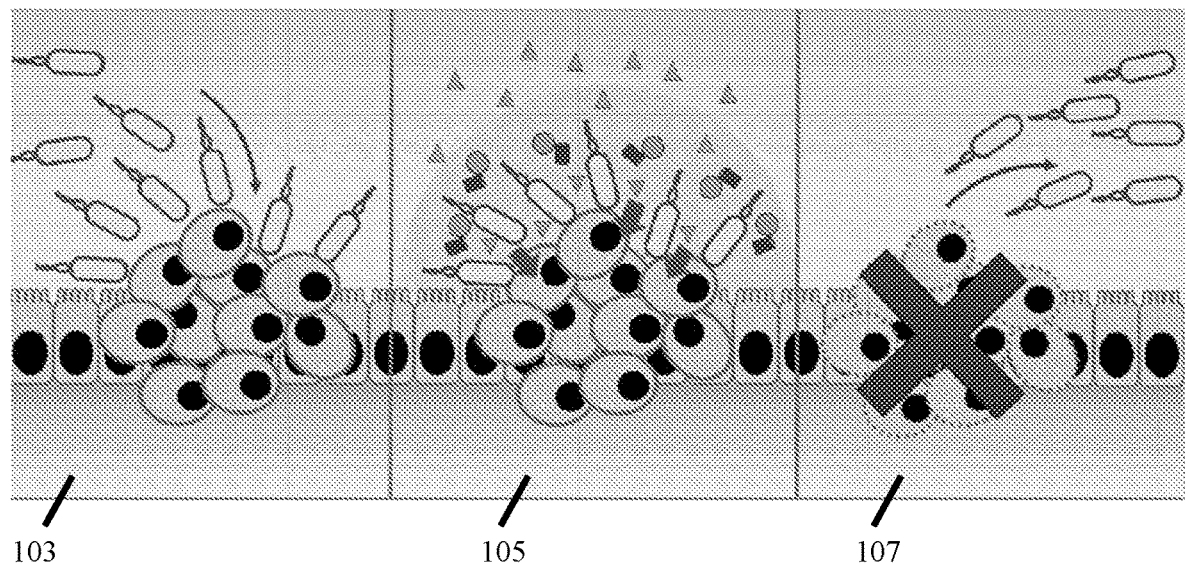

In the illustrative examples contained herein, the aims of the claimed invention are achieved by reprogramming commensal *Escherichia coli* Nissle 1917 (EcN) (101) to bind to the heparan sulfate proteoglycan (HSPG) on the cancer cell surface and to secrete myrosinase for conversion of dietary-glucosinolate to sulforaphane (FIG. 1a). The produced sulforaphane inhibits growth and promotes apoptosis in cancer cells, resulting in colorectal tumor clearance. Upon clearance, the reprogrammed microbes detach from the colorectal tissue and are passed out in the fecal matter (FIG. 1b). This combinatorial approach resulted in almost complete cancer cell inhibition in vitro. In a murine colorectal cancer model, we observed smaller tumors and a 7-fold reduction in tumor occurrence compared to treatments with the engineered microbes or dietary glucosinolate alone.

With greater particularity, FIG. 1 depicts Eda-I1-HlpA for adenocarcinoma clearance. FIG. 1a illustrates an embodiment of the Eda-I1-HlpA construct (101). Secreted YebF-I1 myrosinase catalyzes the glucosinolate hydrolysis to sulforaphane, and INP-HlpA facilitates colorectal cancer cell binding. b. Eda-I1-HlpA mode of action. Orally introduced engineered microbes bind to the surfaces of CRC cells (103), allowing Eda-I1-HlpA to secrete myrosinase to convert ingested dietary glucosinolate (105). Upon cancer cell clearance, the Eda-I1-HlpA is released from the surface of the intestinal mucosa layer (107).

Example 2

Selection of the genetic chassis is illustrated in FIG. 2, screening for glucosinolate-converting myrosinase enzymes. FIG. 2a depicts the phylogeny (201) of the selected myrosinases based on protein sequences. FIG. 2b illustrates myrosinase catalysis of glucosinolate 203. FIGS. 2c and 2d are graphical illustrations 205, 207 of catalytic efficiency of the template enzymes BMY1 and TGG1 against candidate enzymes A6 and I1 in various c. pH and d. temperature conditions (n=3 independent experiments, each measurement performed in triplicates; mean±s.d.).

Figure 3A:
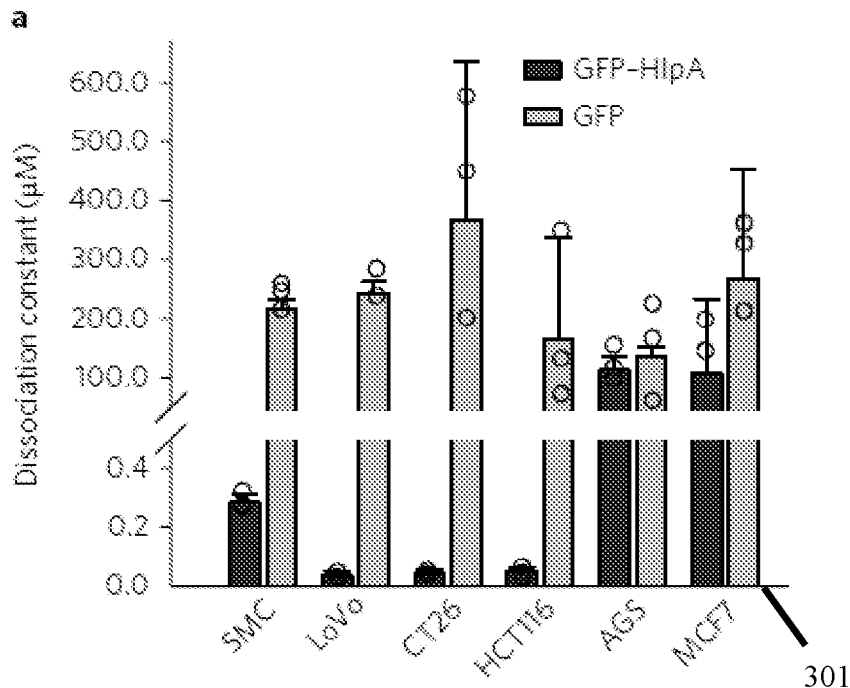
FIG. 3(*a*) is a graphical illustration of GFP tagged HlpA cells against various cancer cell lines.
FIG. 3(b) is a pictorial representation of HlpA binding to various cancer cell lines.
FIG. 3(c) is a pictorial representation of E. coli Nissle 1917 expressing RFP and surface tagged iNP-HlpA protein.
Figure 3B:
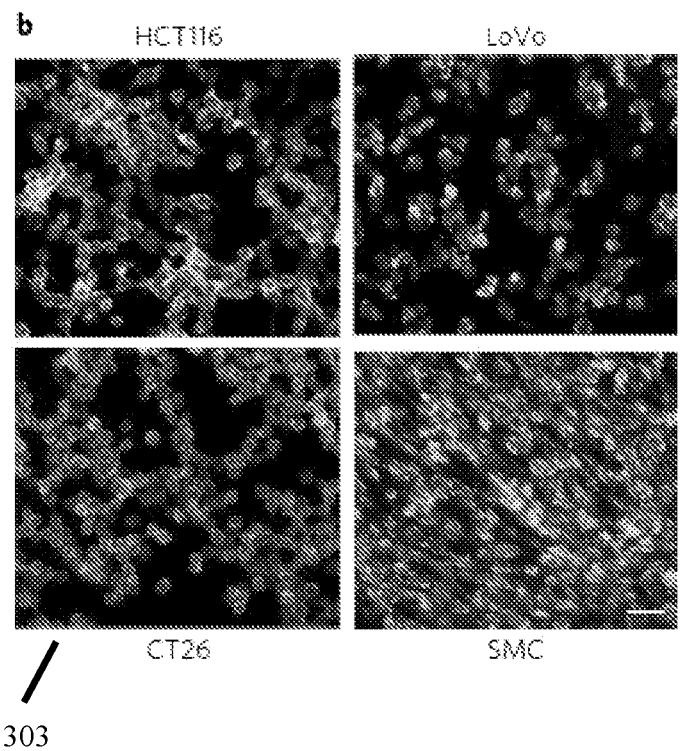
Figure 3C:
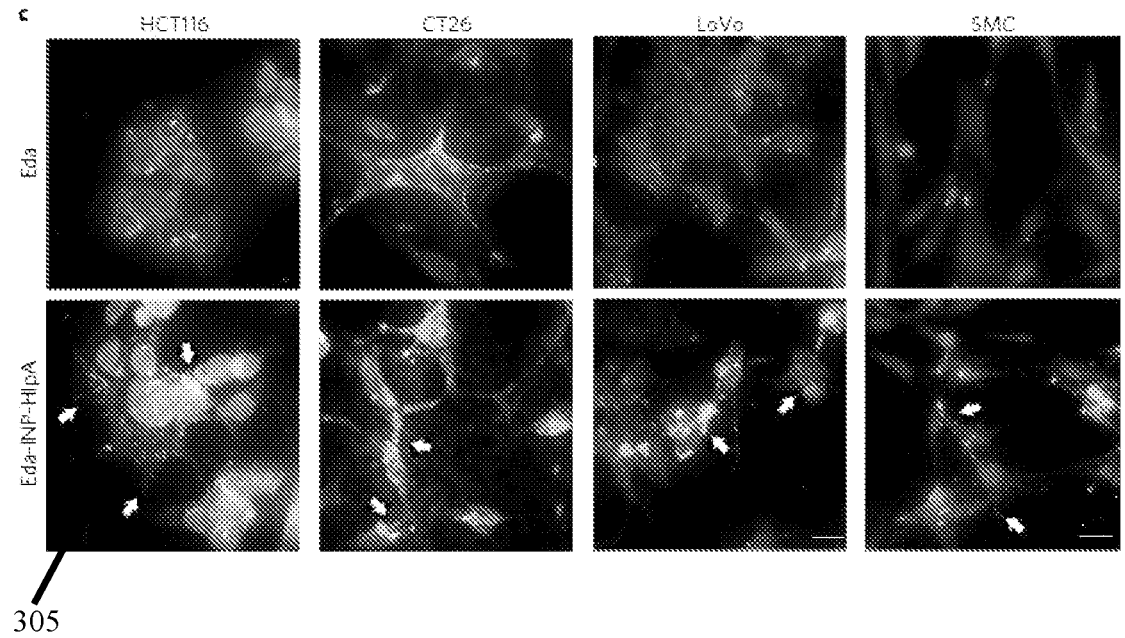

FIGS. 3a, 3b and 3c detail in vitro screening for HlpA binding specificity. FIG. 3a is a graphical illustration (301) of dissociation constant (Kd) of GFP653 tagged HlpA against various cancer cell lines (n=3 independent experiments, each measurement performed in triplicates; mean±s.d.). FIG. 3b illustrates microscopic images (303) of GFP-tagged HlpA (green) binding on various cancer cell lines with nucleus stained with DAPI (blue) (bar: 20 µm). FIG. 3c is a pictorial representation (305) of localization of E. coli Nissle 1917 expressing RFP (red) and surfaced-tagged INP-HlpA protein (indicated by white arrows) on the surfaces of various cancer cell lines with nucleus stained with DAPI (blue) and surface HSPG stained with anti-HSPG conjugated with Alexaflour 488 (green) (bar: 10 µm).

Figure 4A:
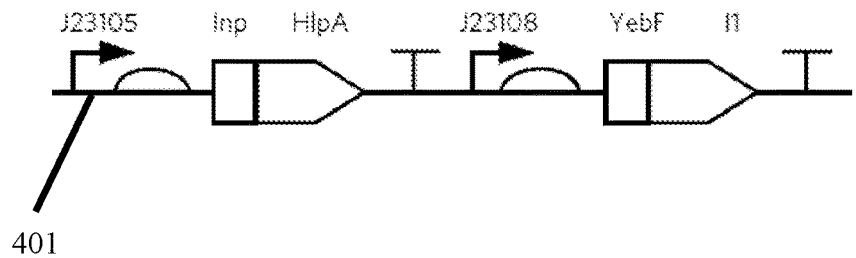
FIG. 4(a) is a top level schematic illustration of genetic circuitry according to the claimed invention.
Figure 4B:
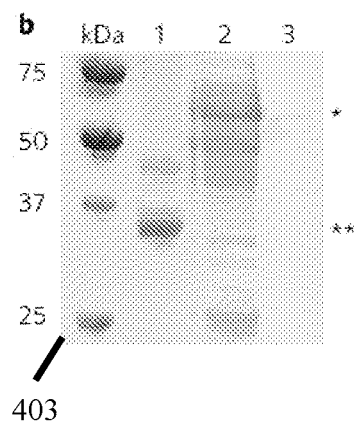
FIG. 4(b) is a pictorial representation of an SDS-Page Gel indicating purified protein.
Figure 4C:
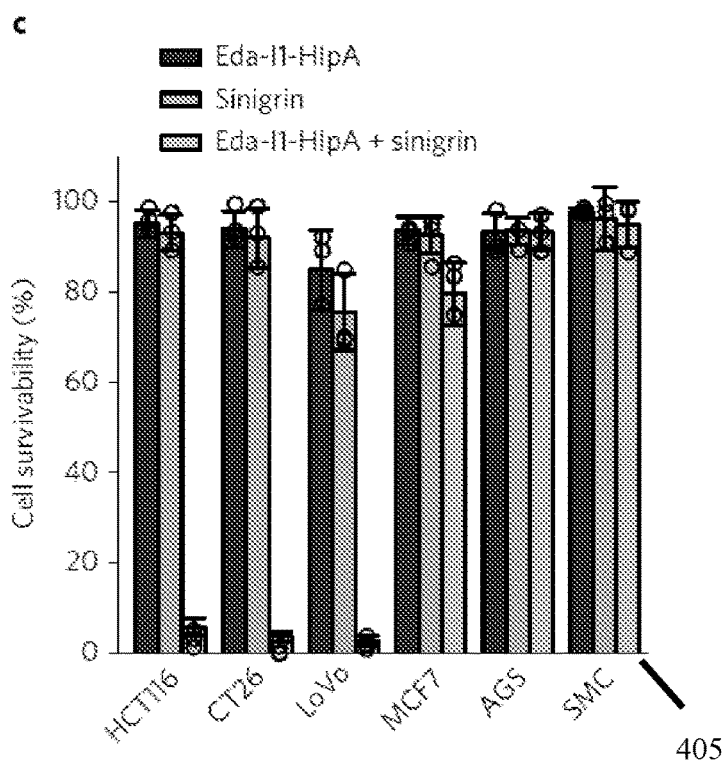
FIG. 4(c) is a graphical illustration of therapeutic efficiency.
Figure 4D:
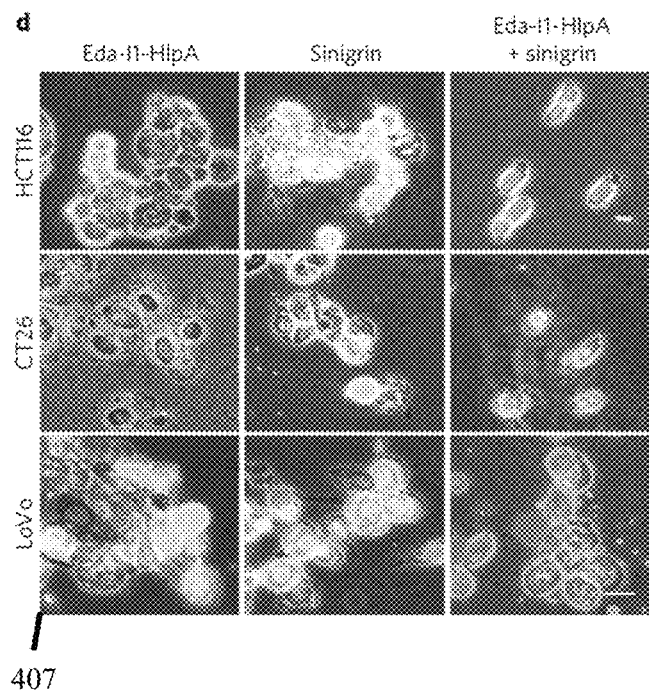
FIG. 4(d) is a pictorial representation of genetically reengineered microbial therapeutic efficiency.

FIGS. 4a, 4b, 4c and 4d illustrate in vitro anticancer activity of engineered microbes in a preferred illustrative embodiment. FIG. 4a depicts a schematic illustration (401) of preferred embodiment gene construct incorporating the binding module gene and the myrosinase secretion gene according to the claimed invention. FIG. 4b illustrates SDS-PAGE gel (403) indicating pulled down purified protein from the expression of secreted myrosinase (*) and surface presenting INP-HlpA (**); Lane 1 is from the inclusion body, Lane 2 is from the intracellular lysate, and Lane 3 is from the extracellular medium. FIG. 4c is a graphical illustration (405) of killing efficiency of engineered microbes in vitro (n=3 independent experiments, mean±s.d.). FIG. 4d is a graphical illustration (407) of various CRC cell lines treated with Eda-I1-HlpA stained with a LIVE/DEAD kit. Live cells are stained in green while dead cells are stained in red (bar: 15 µm).

Figure 5A:
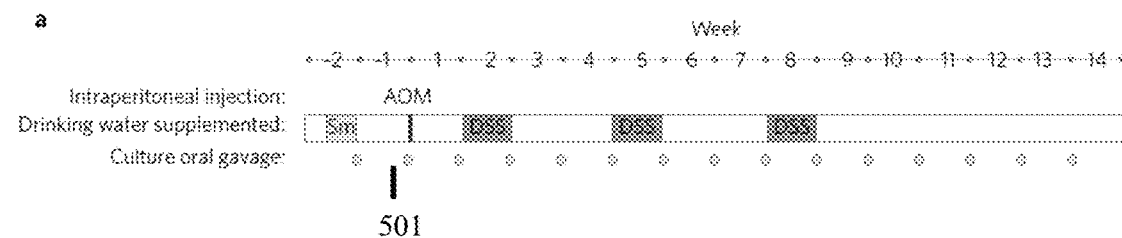
FIG. 5(a) is a graphical illustration of therapeutic treatment schedule intervals.
Figure 5B:
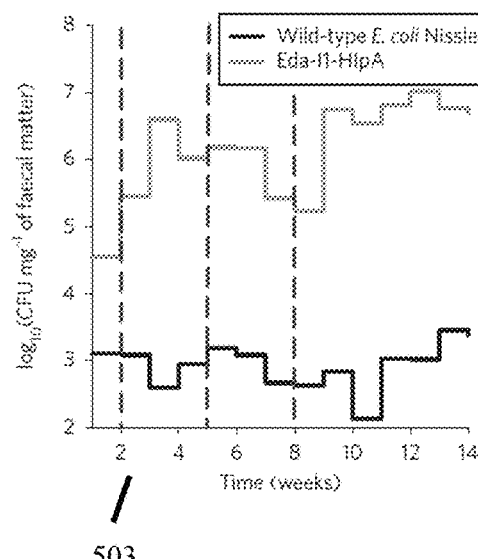
FIG. 5(b) is a graphical illustration of therapeutic treatment characteristics.
Figure 5B:
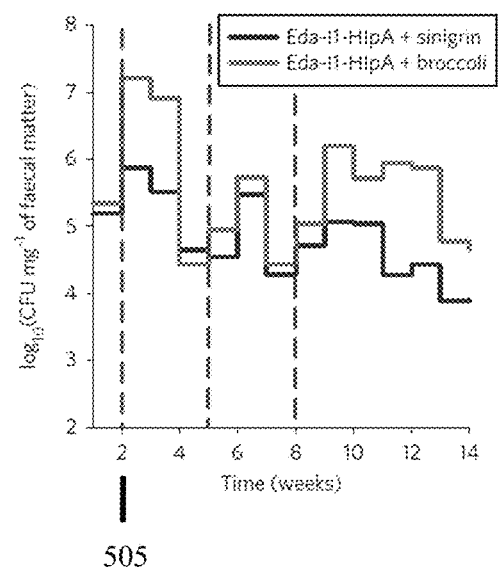
Figure 5C:
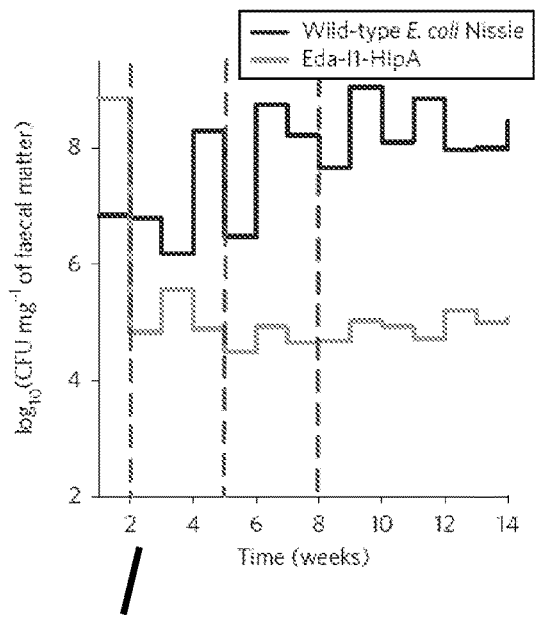
FIG. 5(c) is a graphical illustration of therapeutic treatment characteristics.
Figure 5C:
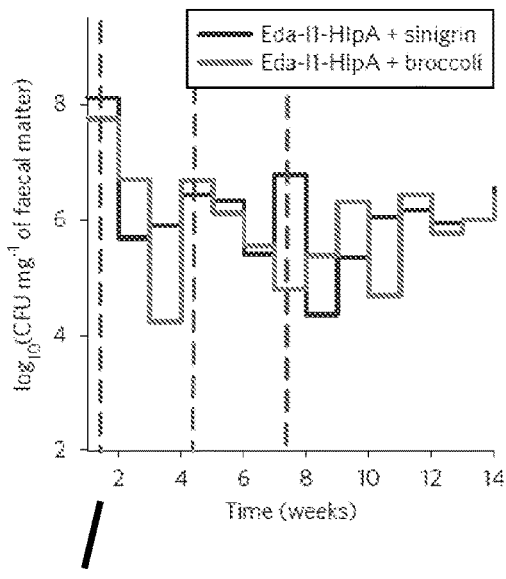
Figure 5D:
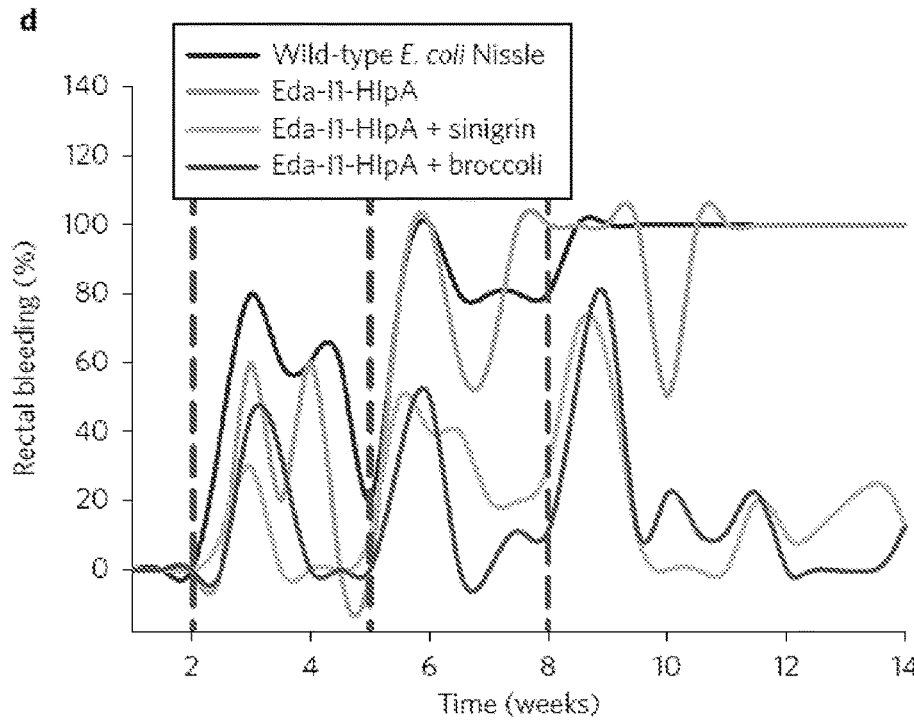
FIG. 5(d) is a graphical illustration of therapeutic treatment characteristics.

FIGS. 5a-d detail treatment of induced CRC in a murine model. FIG. 5a is a timeline (501) illustration of a schedule of animal treatment according to the claimed invention. FIG. 5b is a graphical illustration of washed off Eda-I1-HlpA recovered from 3 hours post-gavage and treated mice in the presence of (505) and absence of (503) therapeutic supplements. FIG. 5c is a graphical illustration of localized Eda-I1-HlpA recovered from fecal matter 4 days post-gavage in the presence of (507) and absence of (509) therapeutic supplements. FIG. 5d is a graphical illustration (511) of rectal bleeding incidences during the duration of treatment (dashed line indicates a one-week DSS treatment in the drinking water).

FIGS. 6a-g depict post-treatment colorectal tissue analysis. a. H&E-stained colorectal tissue (bar: 2.5 mm) (inset: i. Proximal end of the colorectal tissue ii. Distal end of the colorectal tissue (bar: 0.5 mm)). b. Tumor sizes and counts from mice with different treatments, where NS represents nonsignificant, $*p \leq 0.0083$ after Bonferroni correction (n=3~10 mice per group, each group performed in duplicates; mean±s.d.). c. Eda-I1-HlpA recovered from 1 cm of distal colorectal tissue, where NS represents non-significant, $*p \leq 0.05$, $p \leq 0.01$, $*p \leq 0.001$ (n=3~10 mice per group, each group performed in duplicates; mean±s.d.). d. The concentration of NAC-AITC from blood serum isolated from mice from different treatments, where $*p \leq 0.05$ $p \leq 0.01$ $*p \leq 0.001$ (n=3~10 mice per group, each group performed in duplicates; mean±s.d.). e. The staining of colorectal tissue with Alexa Fluor 488 conjugated anti-E. coli, anti-Syndecan 1 and anti-Syndecan 2 antibodies (green) with nucleus counterstained with DAPI (blue) (bar: 100 µm). f. The staining of colorectal tissue with GFP-HlpA and GFP (green) with nucleus counterstained with DAPI (blue) (bar: 100 684 µm). g. The adherence of E. coli Nissle expressing RFP and INP-HlpA (red) to colorectal tissue stained with Alexa Fluor 488 conjugated anti-Syndecan 1 and anti-Syndecan 2 antibodies (green) with nucleus counterstained with DAPI (blue) (bar: 100 µm).

Figure 7:
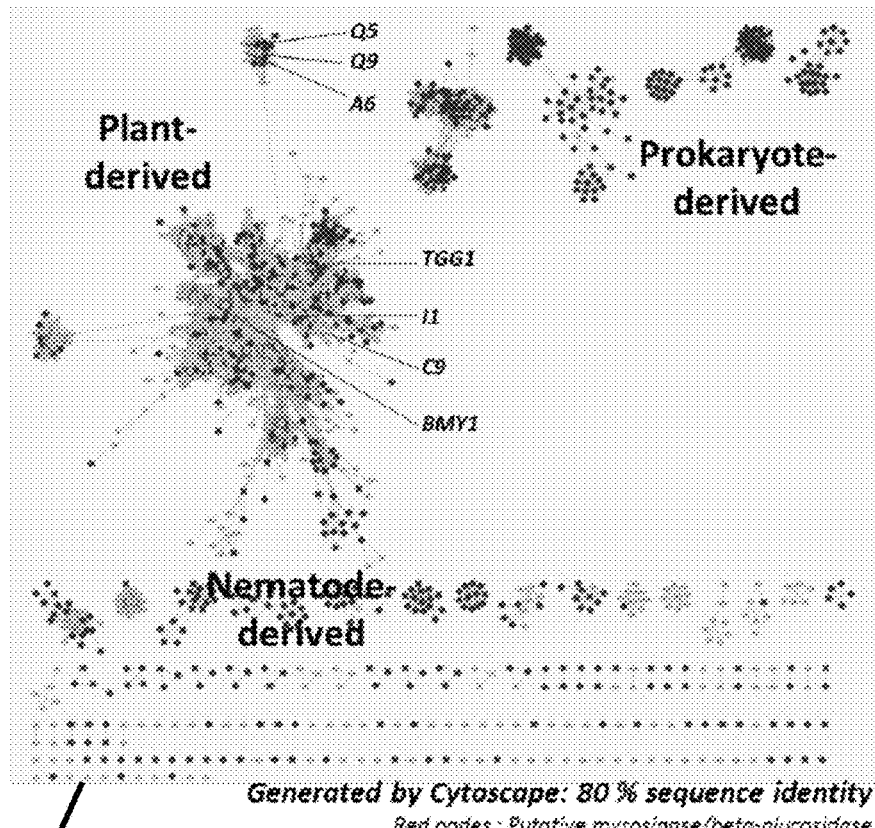
FIG. 7 is a graphical illustration of a cytoscape-generated distribution of putative myrosinase/beta-glucosidase.

FIG. 7 illustrates cytoscape-generated distribution (701) of putative myrosinase/beta-glucosidase.

Figure 8:
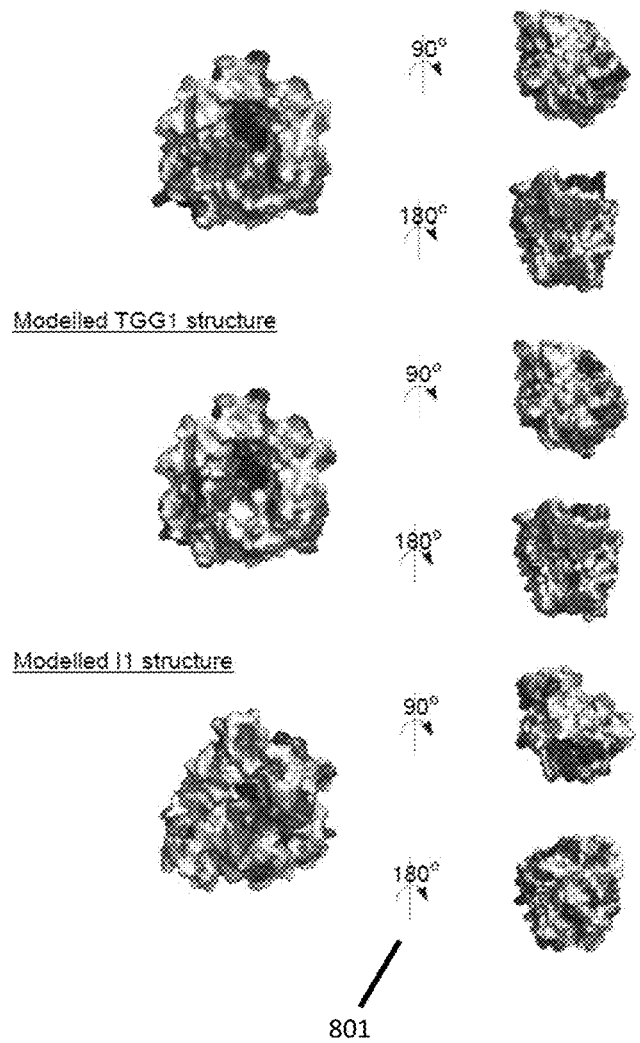
FIG. 8 is a graphical illustration of surface charges of modelled structures of various myrosinases.

FIG. 8 is a pictorial illustration (801) of surface charges of modelled structures of various myrosinases.

Figure 9A:
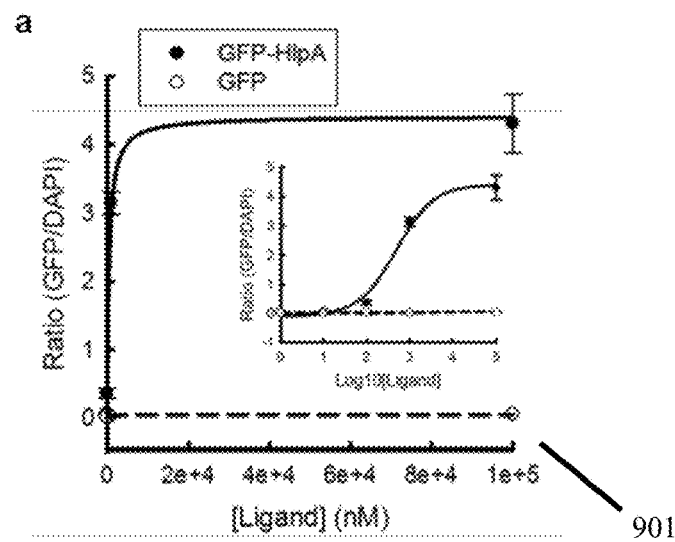
FIG. 9(a)-(f) are graphical illustrations of disassociation constant determination of GFP-HlpA and GFP against various cancer cell lines.
Figure 9B:
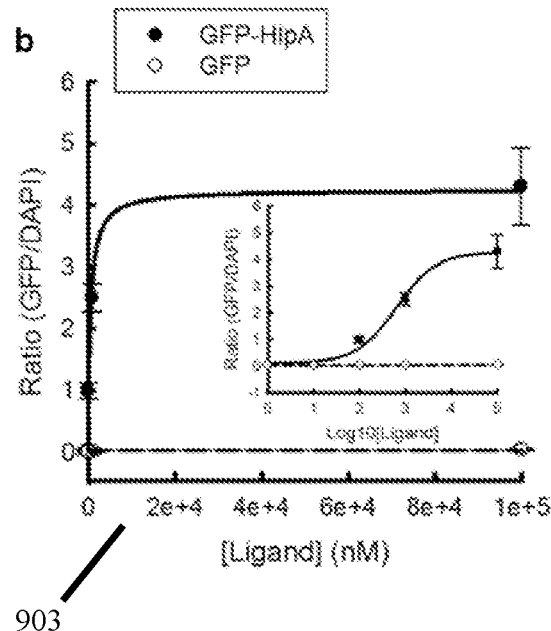
Figure 9C:
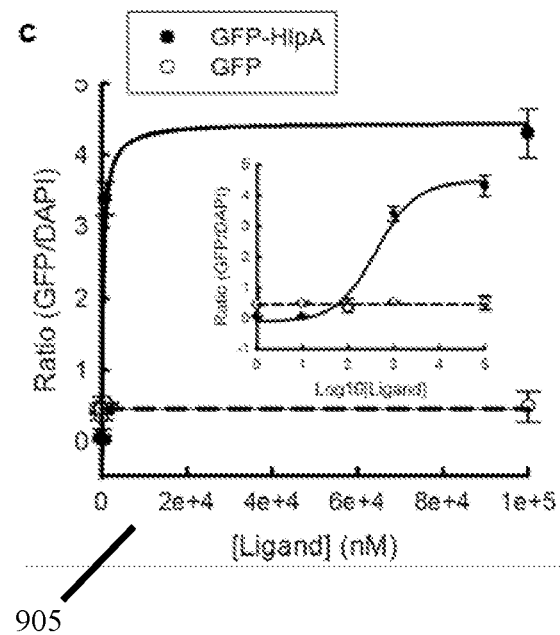
Figure 9D:
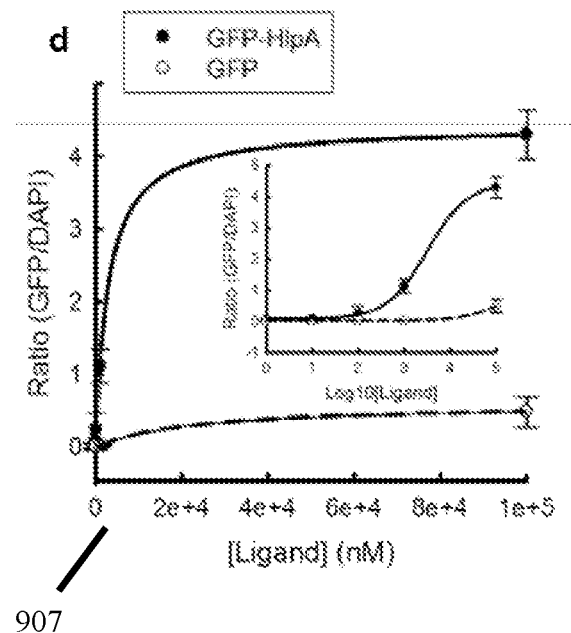
Figure 9E:
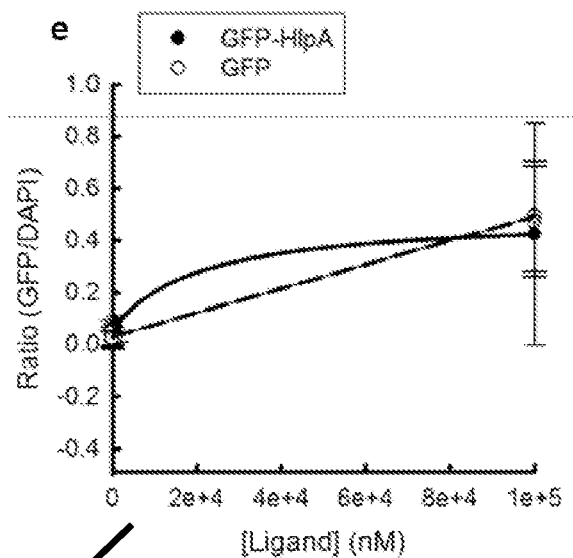
Figure 9F:
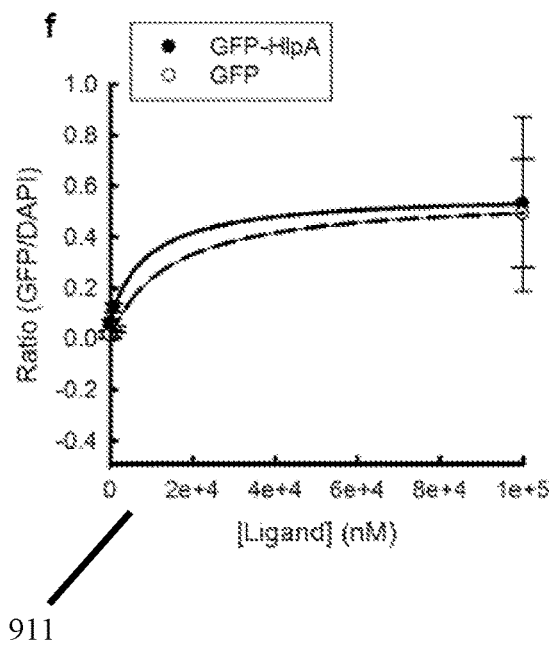

FIG. 9a-f illustrates disassociation constant determination of GFP-HlpA and GFP against various cancer cell lines. FIG. 9a is a graphical illustration (901) of HCT116. FIG. 9b is a graphical illustration (903) of CT26. FIG. 9c is a graphical illustration (905) of LoVo. FIG. 9d is a graphical illustration (907) of SMC. FIG. 9e is a graphical illustration (909) of MCF7. FIG. 9f is a graphical illustration (911) of AGS (n=3 independent experiments, each measurement performed in triplicates; mean±s.d.).

Figure 10:
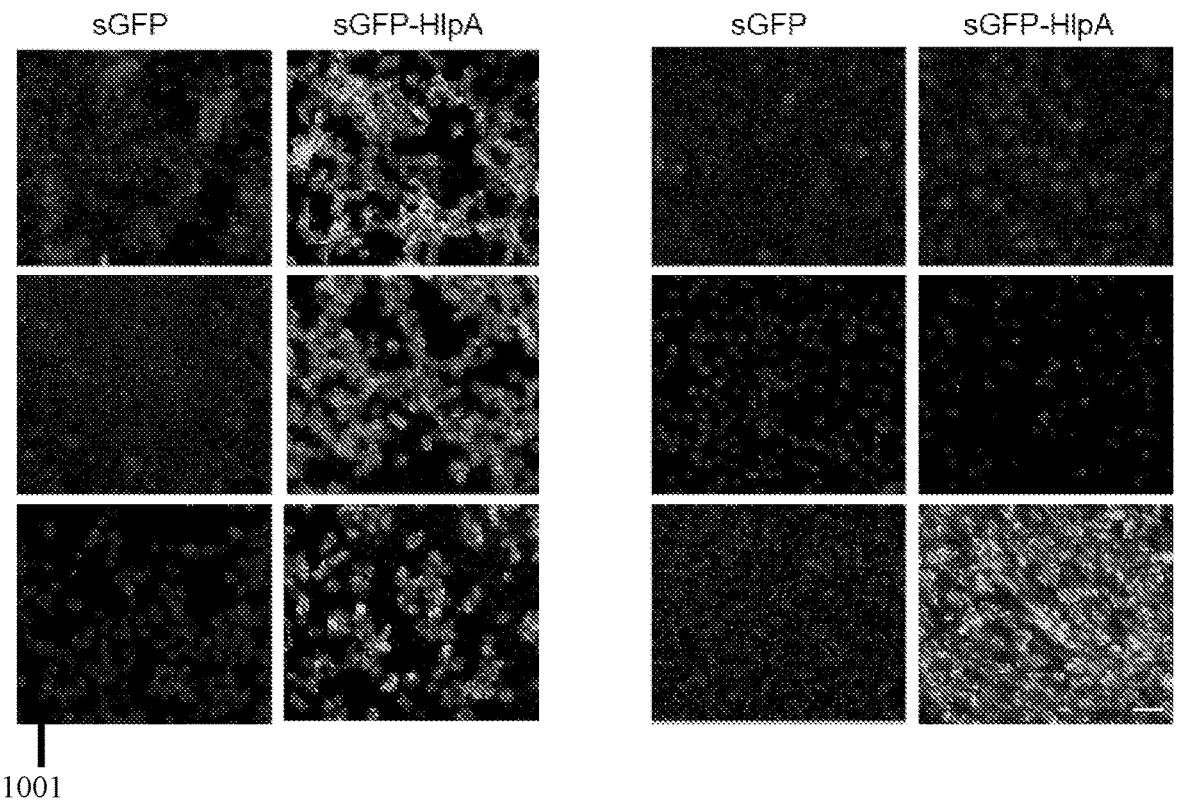
FIG. 10 is a pictorial representation of GFP-tagged HlpA binding on various cancer cell lines.

FIG. 10 is a pictorial microscopic image (1001) of GFP-tagged HlpA binding to various cancer cell lines inclusive of control groups. GFP-tagged HlpA or GFP (green); DAPI stained nucleus (blue) (Bar: 20 µm).

Figure 11:
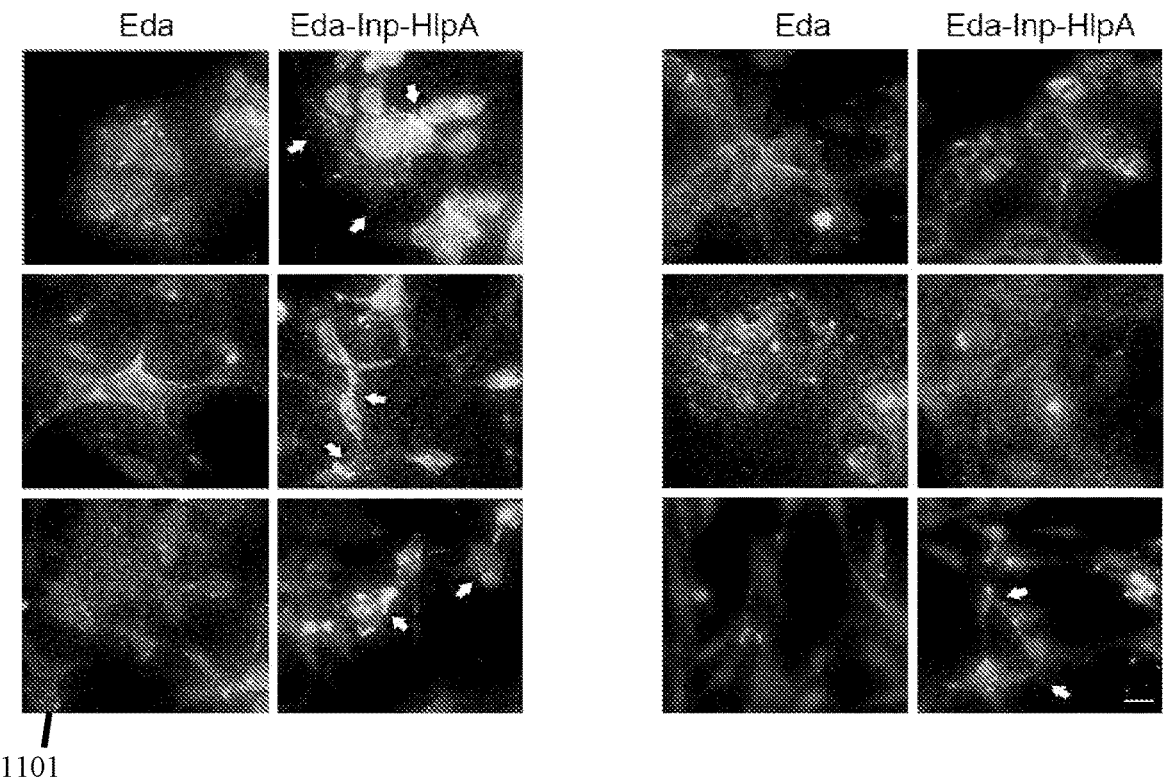
FIG. 11 is a pictorial representation of localization of E. coli Nissle 1917 (EcN) expressing RFP and surfaced tagged INP-HlpA protein on the surface of various cancer cell lines.

FIG. 11 is a pictorial illustration (1101) of the localization of E. coli Nissle 1917 (EcN) expressing RFP and surfaced tagged INP-HlpA protein (indicated by white arrows) on the surfaces of various cancer cell lines inclusive of control groups. EcN expressing RFP (red); Alexa Fluor 488 conjugated anti-HSPG antibody (green); DAPI stained nucleus (blue) (Bar: 10 µm).

Figure 12:
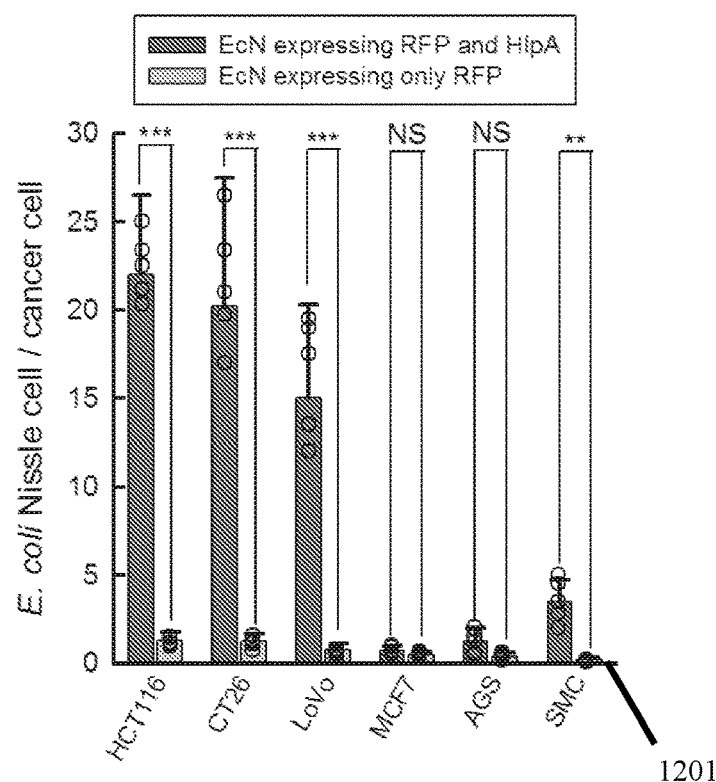
FIG. 12 is a graphical illustration of the ratio of localization of E. coli Nissle 1917 (EcN) expressing RFP and surfaced tagged INP-HlpA protein in each cancer cell.

FIG. 12 is a graphical illustration (1201) of the ratio of localization of E. coli Nissle 1917 (EcN) expressing RFP and surfaced tagged INP-HlpA protein in each cancer cell inclusive of control groups. Ratios were established using fluorescence emission of RFP and DAPI converted into cell count based on pre-established standard curves, where $*p \leq 0.05$, $p \leq 0.01$, $*p \leq 0.001$ (n=5 independent experiments, each measurement performed in triplicates; mean±s.d.).

Figure 13:
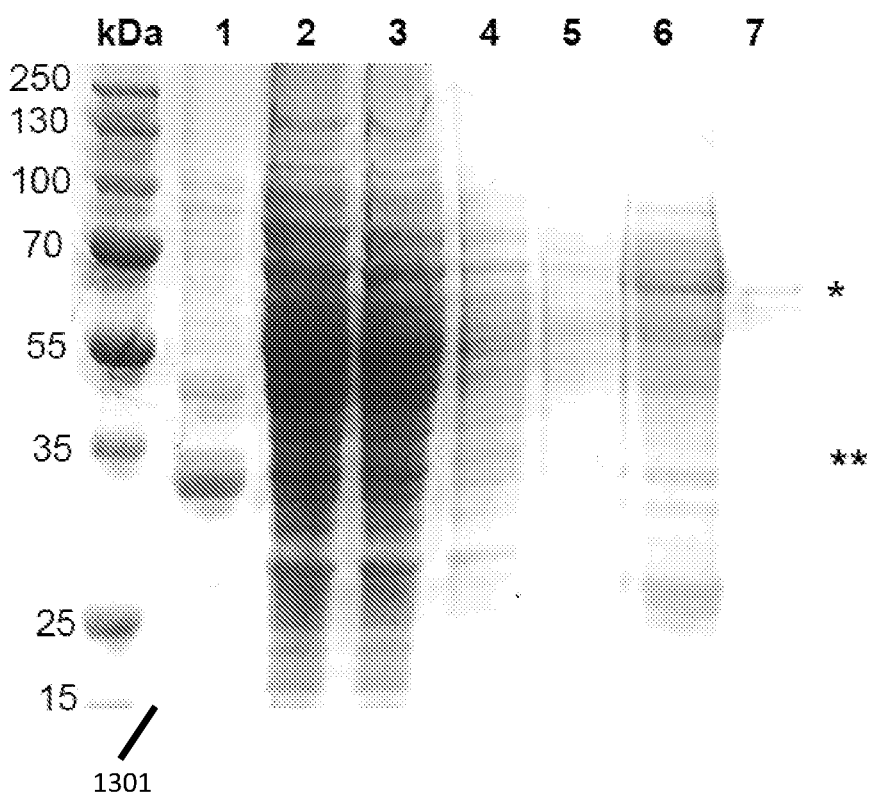
FIG. 13 is a pictorial representation of SDS-PAGE gel indicating expression of secreted myrosinase and surface presenting INP-HlpA.

FIG. 13 is a pictorial illustration (1301) of SDS-PAGE gel indicating expression of secreted myrosinase (*) and surface presenting INP-HlpA(**). Lane 1 is the pulled down purified protein from solubilized inclusion body, Lane 2 and 3 the crude solubilized inclusion body, Lane 4 the crude intracellular lysate, Lane 5 the crude extracellular medium, Lane 6 the pulled down purified protein from the intracellular lysate and Lane 7 the pulled down purified protein from the extracellular medium.

Figure 14:
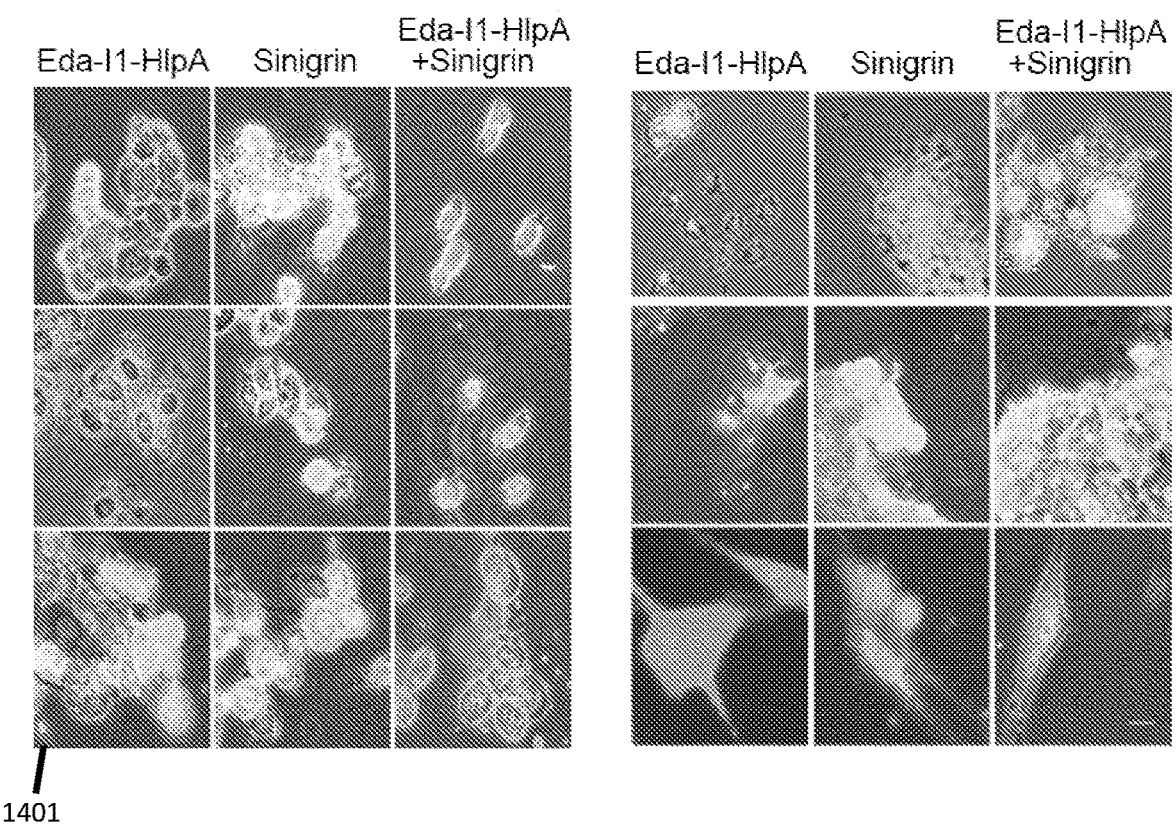
FIG. 14 is a pictorial representation of colorectal cancer cell lines treated with Eda-I1-HlpA and/or sinigrin stained.

FIG. 14 is a pictorial illustration (1401) of various CRC cell lines treated with Eda-I1-HlpA and/or sinigrin stained with a LIVE/DEAD kit. Live cells are stained green and dead cells in red (Bar: 15 µm).

Figure 15:
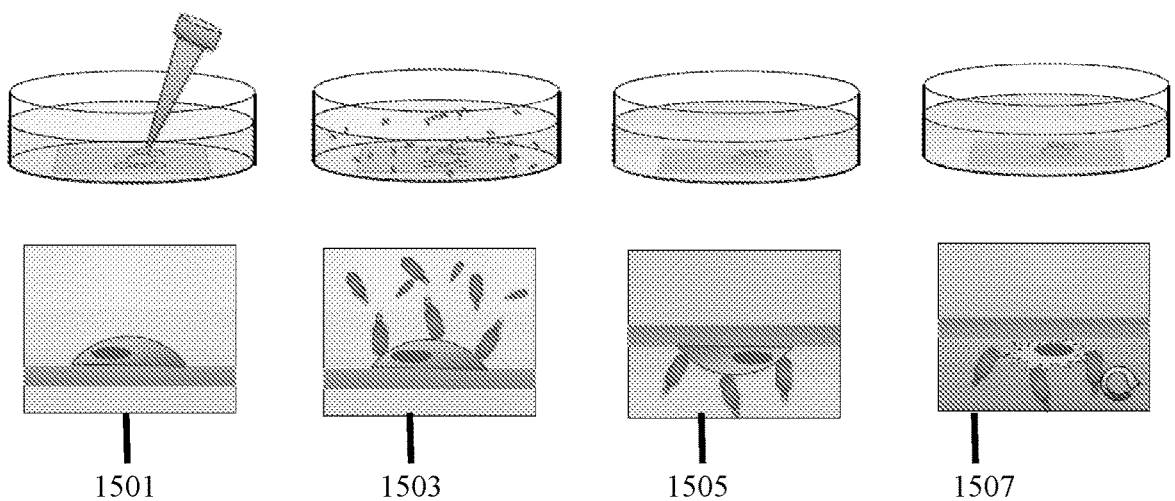
FIG. 15 is a schematic illustration of preparation of cancer cells and Eda-I1-HlpA co-cultured slides.

FIG. 15 is a schematic illustration of preparation of cancer cells and Eda-I1-HlpA co-cultured slides. In the illustration, cells are grown on the surfaces of glass slides until 80% confluent (1501). Eda-I1-HlpA is introduced to the medium for 30 minutes before being washed twice with 1× PBS (1503). Slides (1505) are inverted face down in antibiotic-free culture media containing sinigrin. Slides (1507) are incubated for 24 hours prior to staining with a LIVE/DEAD kit and viewed under a fluorescence microscope.

Figure 16A:
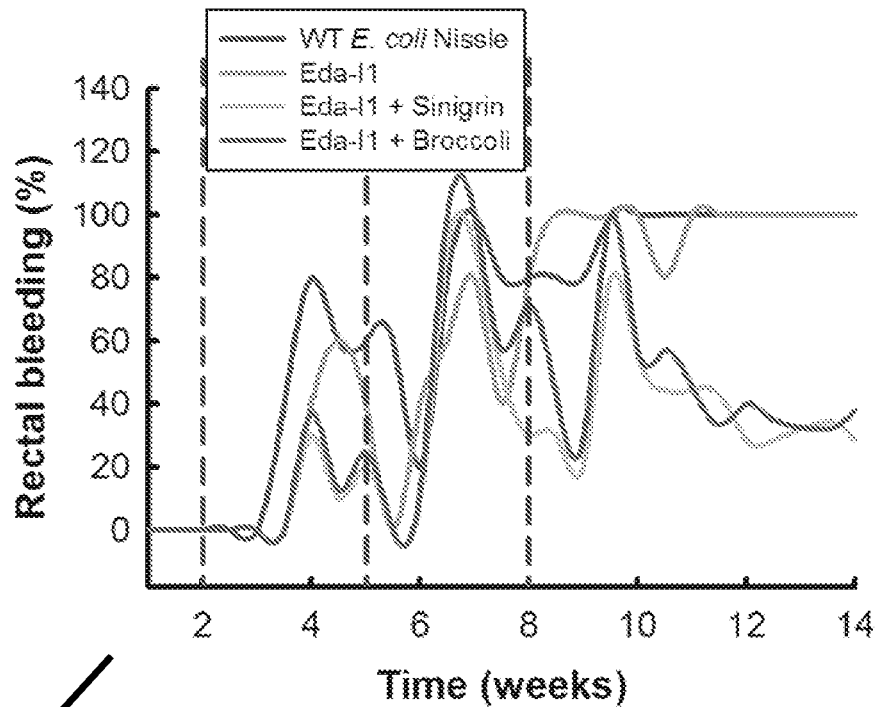
FIGS. 16(a) and (b) are graphical illustrations of percentage of Rectal Bleeding incidences in Eda-I1-fed mice and Eda-I1-HlpA-fed mice.
Figure 16B:
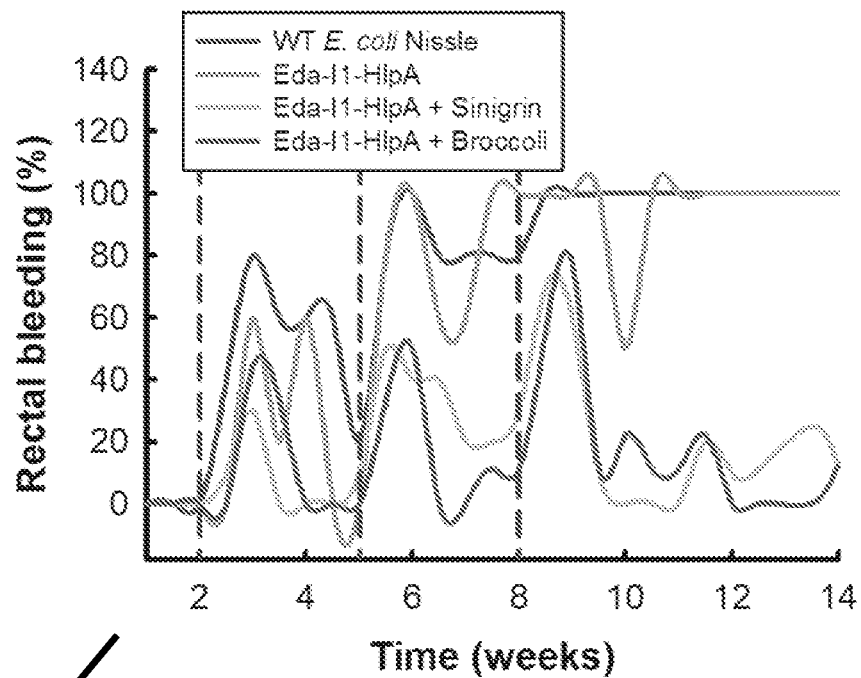

FIGS. 16a and 16b are graphical illustrations (1601), (1603) of percentage of rectal bleeding incidences in Eda-I1-fed mice (1601) and Eda-I1-HlpA-fed mice (1603).

Figure 17A:
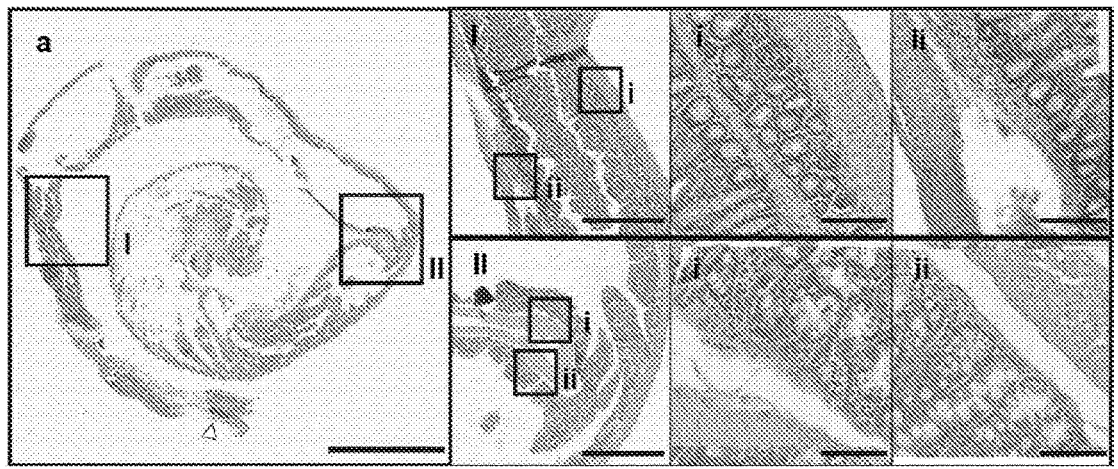
FIGS. 17(a) and (b) are pictorial representations of histology of colorectal tissue from AOM/DSS treated and untreated mice.
Figure 17B:
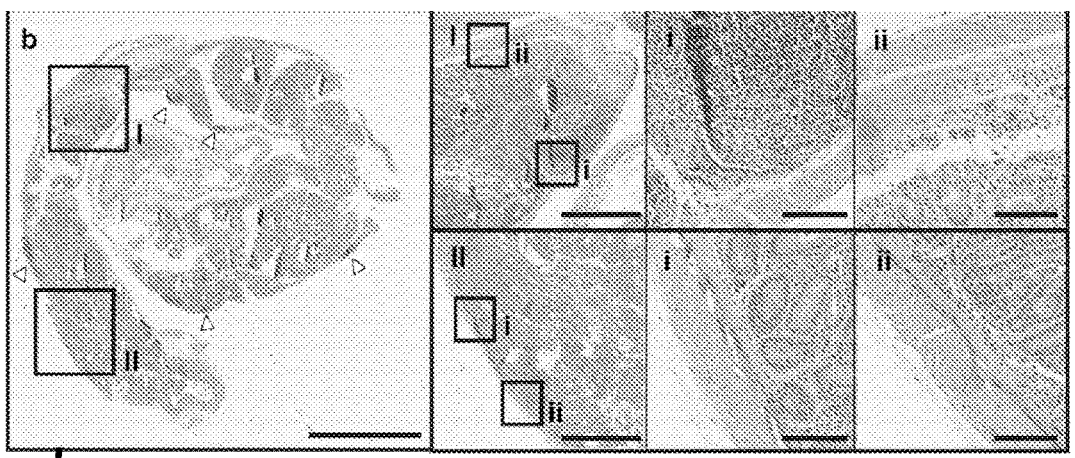

FIGS. 17a and 17b are pictorial representations (1701), (1703) of histology of colorectal tissue from AOM/DSS treated and untreated mice. FIG. 17a illustrates tissue section from mouse not treated with AOM/DSS, scale bar: 5 mm. FIG. 71b represents tissue section from mouse treated with AOM/DSS, scale bar: 5 mm (inset: boxes indicated with capital roman numerals indicate 2× magnification, scale bar: 500 µm. Boxes indicated with small roman numerals indicate 20× magnification, scale bar: 50 µm) (white arrows indicate GALT).

Figure 18A:
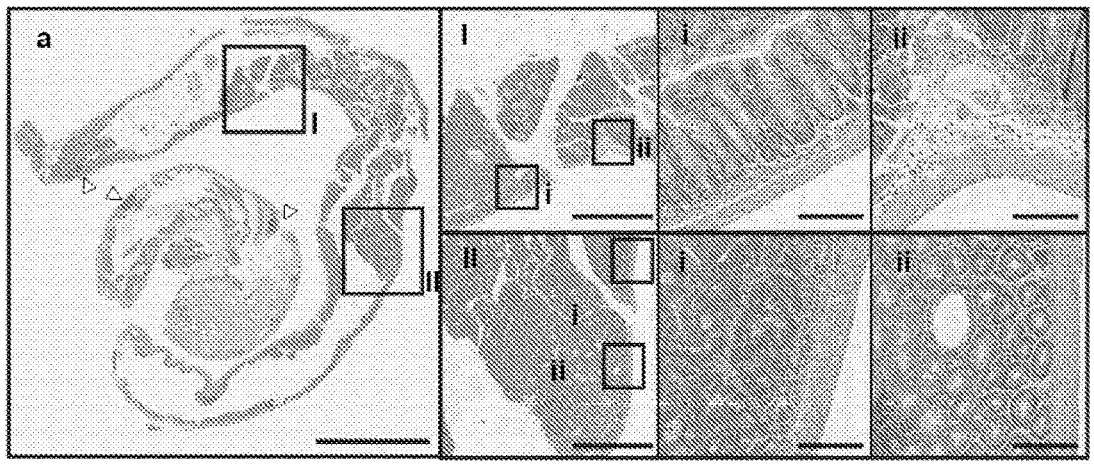
FIGS. 18(a) and (b) are pictorial representations of histology of colorectal tissue from AOM/DSS treated mice fed with Eda-I1.
Figure 18B:
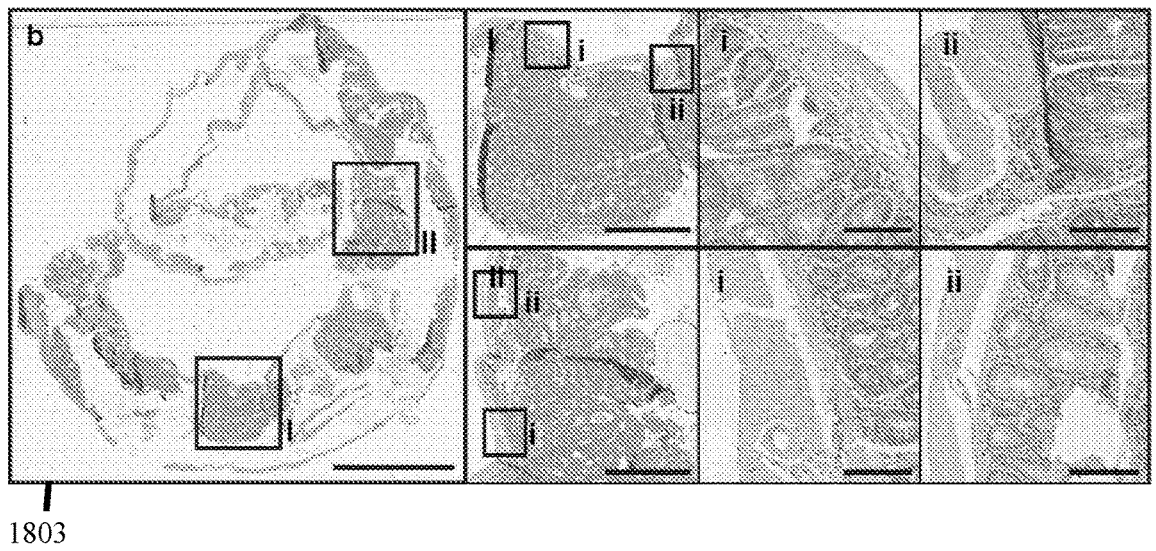

FIGS. 18a and 18b are pictorial representations (1801), (1803) of histology of colorectal tissue from AOM/DSS treated mice fed with Eda-I1. FIG. 18a illustrates tissue section from mouse treated with AOM/DSS and fed with Eda-I1 and sinigrin, scale bar: 5 mm. FIG. 18b illustrates tissue section from mouse treated with AOM/DSS and fed with Eda-I1 and broccoli, scale bar: 5 mm (inset: boxes I-II indicate 2× magnification, scale bar: 500 µm. Boxes i-ii indicate 20× magnification, scale bar: 50 µm) (white arrows indicate GALT).

Figure 19A:
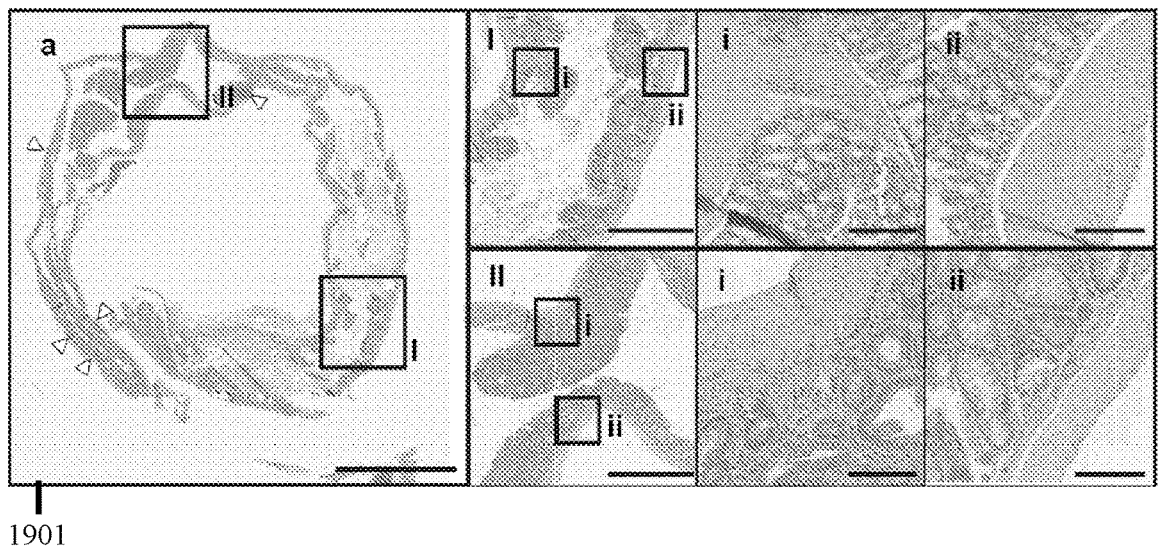
FIGS. 19(a) and (b) are pictorial representations of histology of colorectal tissue from AOM/DSS treated mice fed with Eda-I1-HlpA.
Figure 19B:
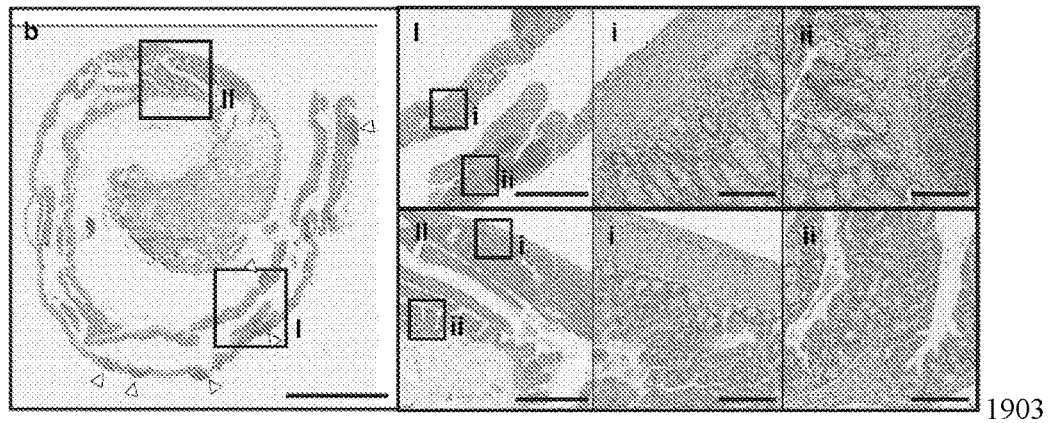

FIGS. 19a and 19b are pictorial representations (1901), (1903) of histology of colorectal tissue from AOM/DSS treated mice fed with Eda-I1-HlpA. FIG. 19a illustrates tissue section from mouse treated with AOM/DSS and fed with Eda-I1-HlpA and sinigrin, scale bar: 5 mm. FIG. 19b illustrates tissue section from mouse treated with AOM/DSS and fed with Eda-I1-HlpA and broccoli, scale bar: 5 mm (inset: boxes I-II indicate 2× magnification, scale bar: 500 µm. Boxes i-ii indicate 20× magnification, scale bar: 50 µm) (white arrows indicate GALT).

Figure 20:
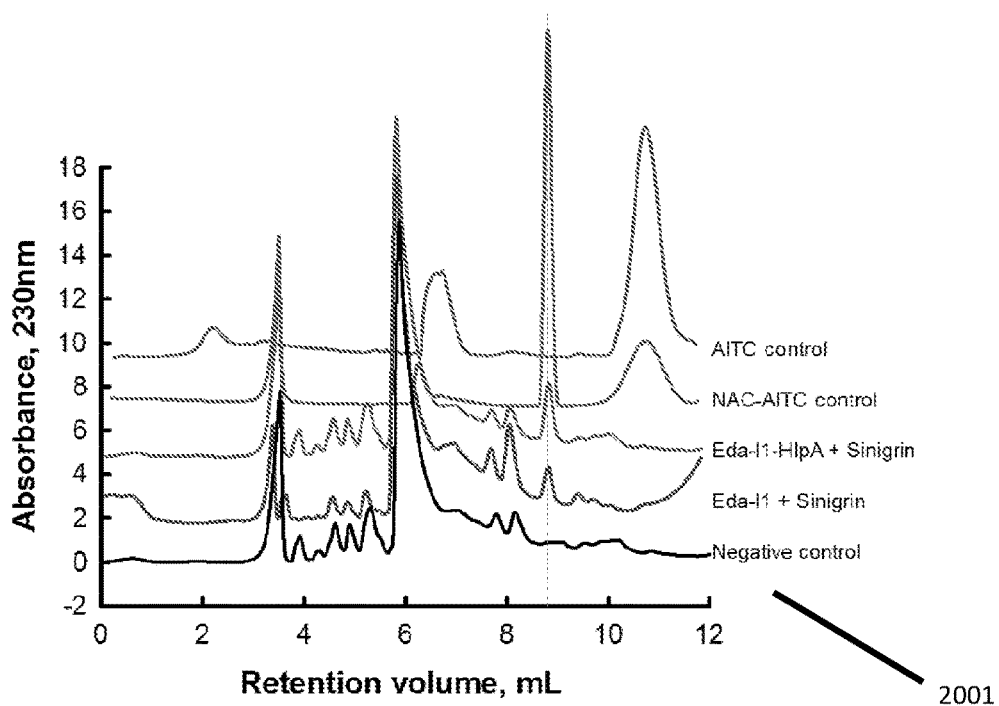
FIG. 20 is a graphical illustration of separation of mice blood serum and detection of N-115 acetyl-cysteine AITC using High Performance Liquid Chromatography.
Figure 21:
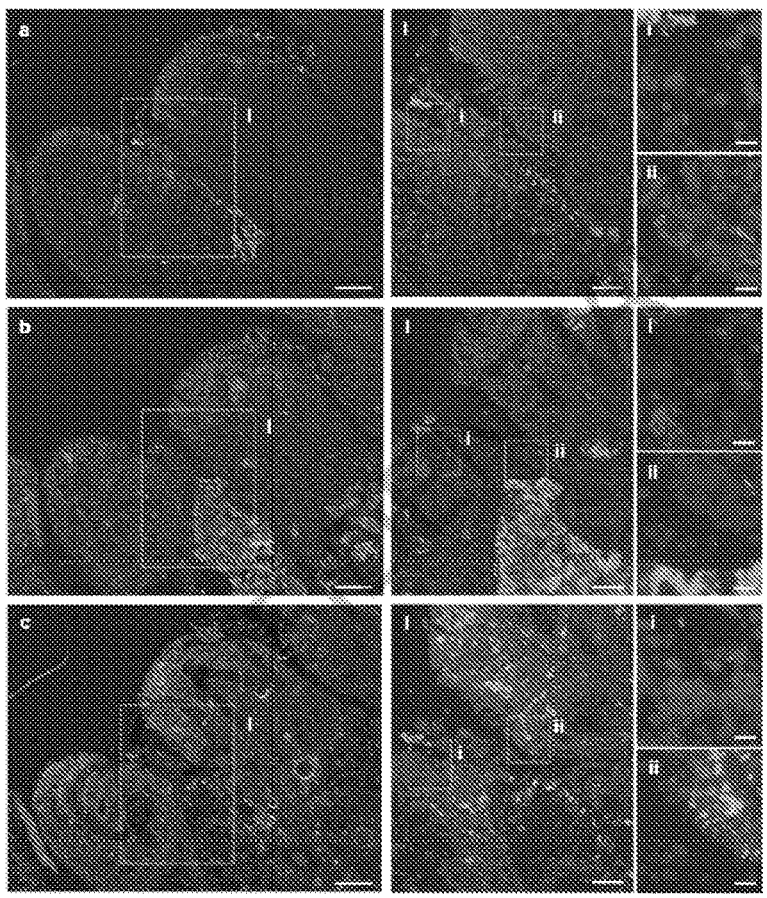
FIG. 21 is a pictorial representation of histology of colorectal tissue from AOM/DSS treated mice fed with Eda-I1-HlpA, stained with Alexa Fluor 488 conjugated anti-E. coli, anti-Syndecan 1 or anti-Syndecan 2 antibody.

FIG. 20 is a graphical illustration (2001) of separation of mice blood serum and detection of N-115 acetyl-cysteine AITC using High Performance Liquid Chromatography. NAC-AITC maxima retention volume is 8.8 mL, AITC maxima retention volume is 10.9 mL FIG. 21 is a pictorial representation (2101) of histology of colorectal tissue from AOM/DSS treated mice fed with Eda-I1-HlpA, stained with Alexa Fluor 488 conjugated anti-E. coli, anti-Syndecan 1 or anti-Syndecan 2 antibody. a. Tissue section with DAPI-stained nucleus (blue) from AOM/DSS treated mouse fed with Eda-I1-HlpA stained with Alexa Fluor 488 conjugated anti-E. coli (green), scale bar: 10 mm. b. Tissue section with DAPI-stained nucleus (blue) from AOM/DSS treated mouse fed with Eda-I1-HlpA stained with Alexa Fluor 488 conjugated anti-Syndecan 1 (green), scale bar: 10 mm. c. Tissue section with DAPI-stained nucleus (blue) from AOM/DSS treated mouse fed with Eda-I1-HlpA stained with Alexa Fluor 488 conjugated anti-Syndecan 2 (green), scale bar: 10 mm. (inset: boxes I-II indicate 20× objective magnification, scale bar: 20 µm. Boxes i-ii indicate 100× objective magnification, scale bar: 100 µm). Fluorescence image analysis is shown in FIG. 24.

Figure 22:
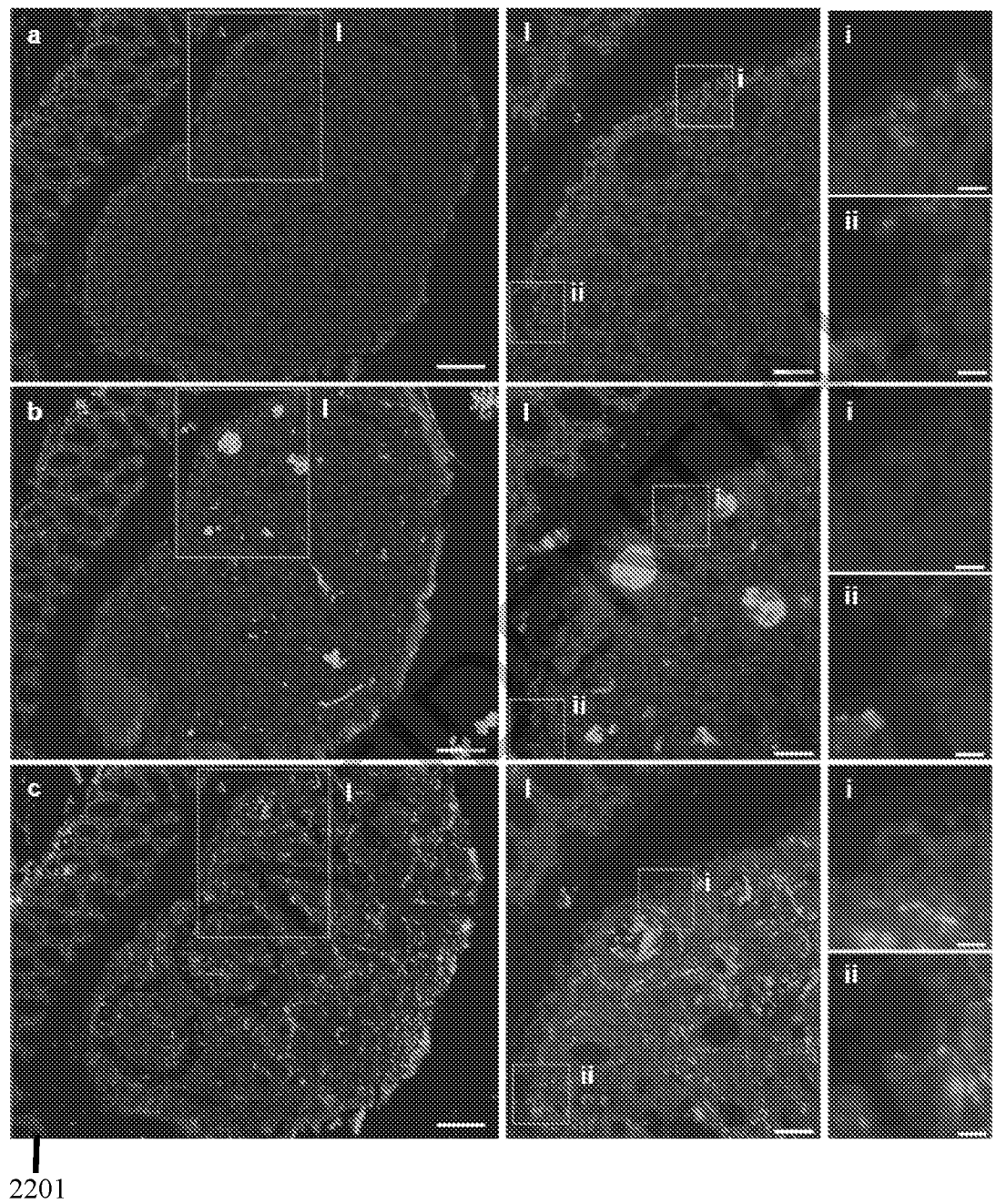
FIG. 22 is a pictorial representation of histology of colorectal tissue from AOM/DSS treated mice fed with Eda-I1, stained with Alexa Fluor 488 conjugated anti-E. coli, anti-Syndecan 1 or anti-Syndecan 2 antibody.

FIG. 22 is a pictorial representation (2201) of histology of colorectal tissue from AOM/DSS treated mice fed with Eda-I1, stained with Alexa Fluor 488 conjugated anti-E. coli, anti-Syndecan 1 or anti-Syndecan 2 antibody. Panel a illustrates issue section with DAPI-stained nucleus (blue) from AOM/DSS treated mouse fed with Eda-I1 stained with Alexa Fluor 488 conjugated anti-E. coli (green), scale bar: 10 mm. Frame b illustrates tissue section with DAPI-stained nucleus (blue) from AOM/DSS treated mouse fed with Eda-I1 stained with Alexa Fluor 488 conjugated anti-Syndecan 1 (green), scale bar: 10 mm. Section c details tissue section with DAPI-stained nucleus (blue) from AOM/DSS treated mouse fed with Eda-I1 stained with Alexa Fluor 488 conjugated anti-Syndecan 2 (green), scale bar: 10 mm. (inset: boxes I-II indicate 20× objective magnification, scale bar: 20 µm. Boxes i-ii indicate 100× objective magnification, scale bar: 100 µm). Fluorescence image analysis is shown in FIG. 24.

Figure 23:
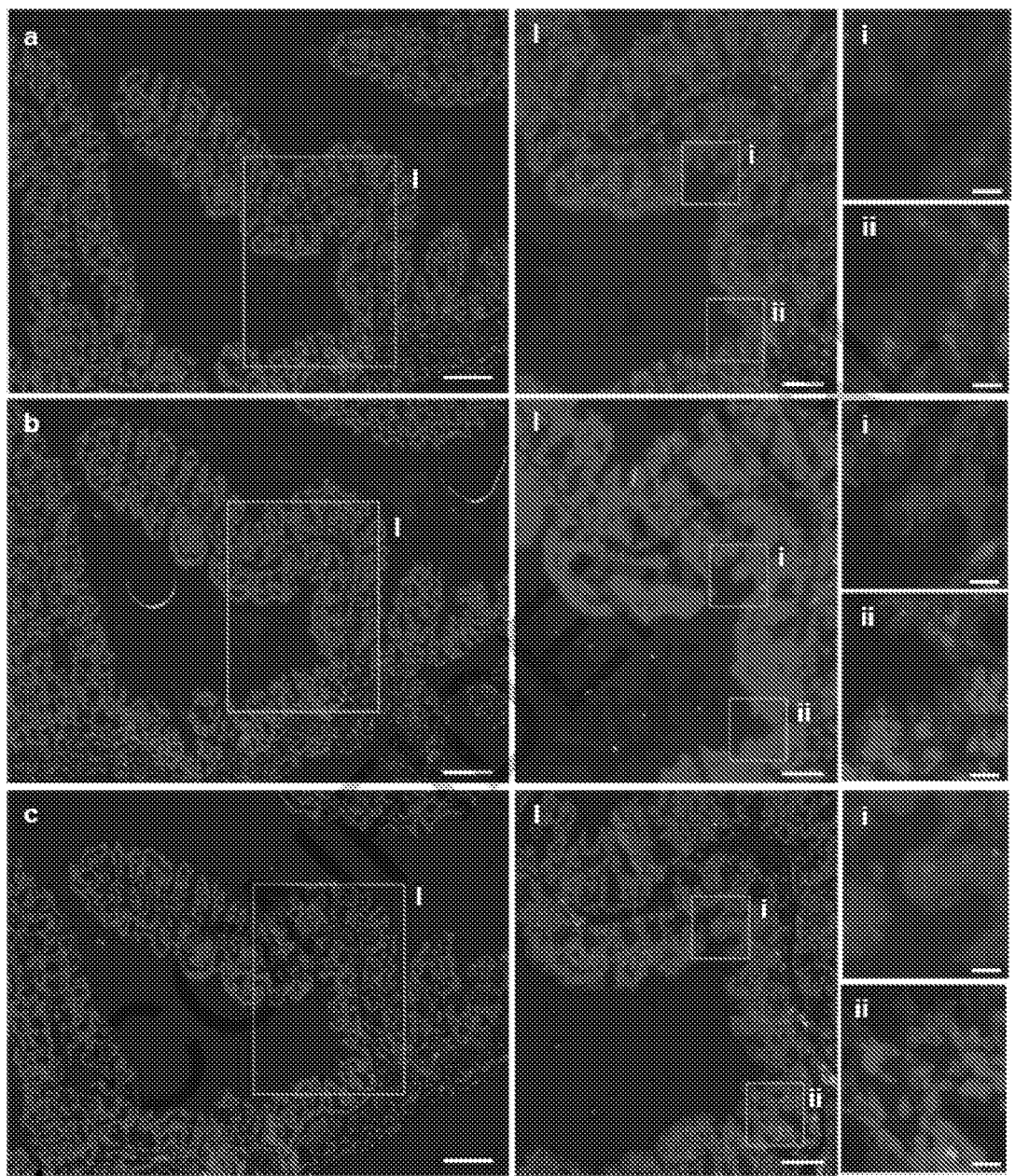
FIG. 23 is a pictorial representation of histology of colorectal tissue from untreated mouse stained with Alexa Fluor 488 conjugated anti-E. coli, anti-Syndecan 1 or anti-Syndecan 2 antibody.

FIG. 23 is a pictorial representation (2301) of histology of colorectal tissue from untreated mouse stained with Alexa Fluor 488 conjugated anti-E. coli, anti-Syndecan 1 or anti-Syndecan 2 antibody. Panel a details tissue section with DAPI-stained nucleus (blue) from untreated mouse stained with Alexa Fluor 488 conjugated anti-E. coli (green), scale bar: 10 mm. Section b details tissue section with DAPI-stained nucleus (blue) from untreated mouse stained with Alexa Fluor 488 conjugated anti-Syndecan 1 (green), scale bar: 10 mm. Section c shows tissue section with DAPI-stained nucleus (blue) from untreated mouse stained with Alexa Fluor 488 conjugated anti-Syndecan 2 (green), scale bar: 10 mm. (inset: boxes I-II indicate 20× objective magnification, scale bar: 20 Boxes i-ii indicate 100× objective magnification, scale bar: 100 µm). Fluorescence image analysis is shown in FIG. 24.

Figure 24:
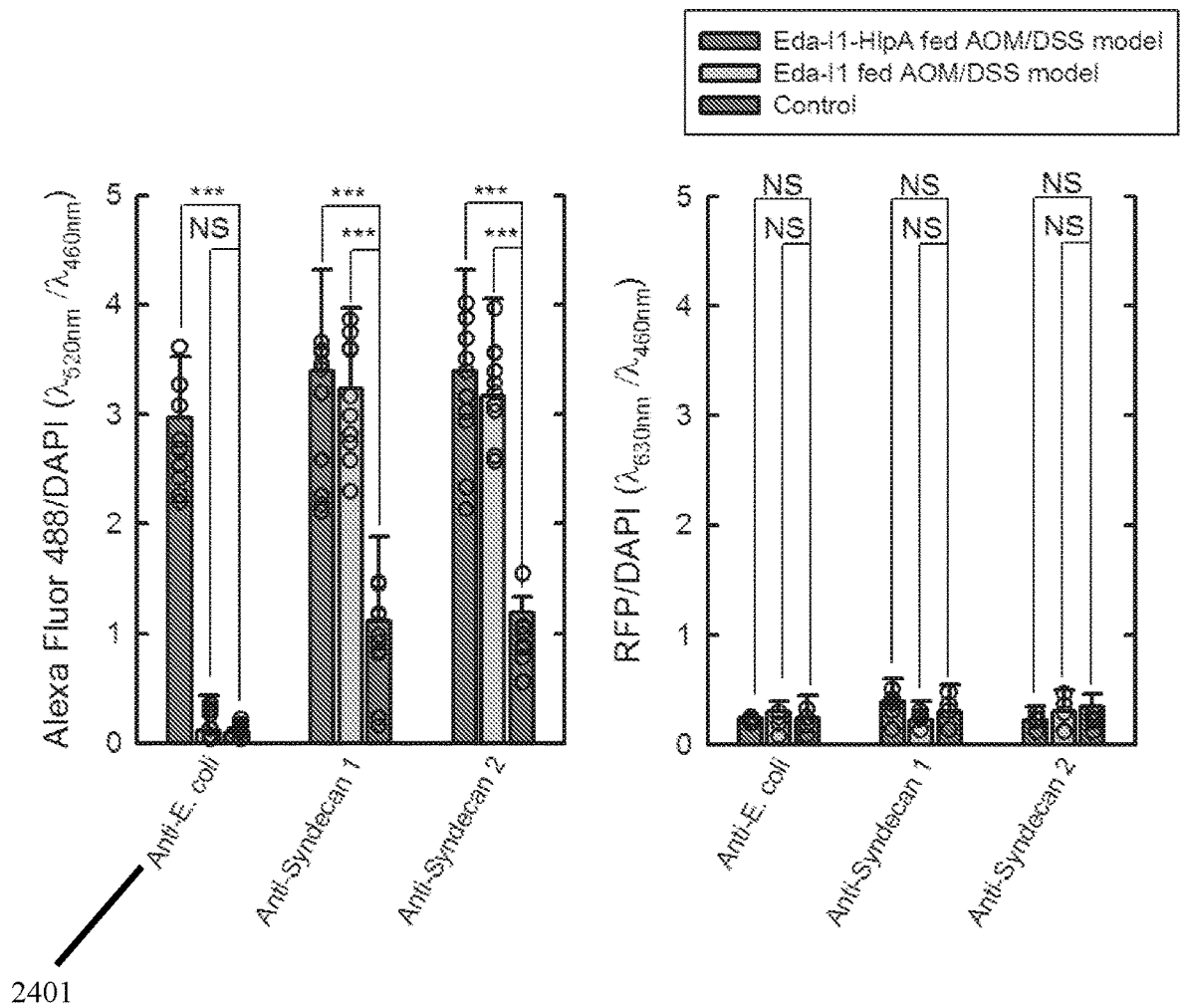
FIG. 24 is a graphical illustration of fluorescence image analysis of murine colorectal tissue stained with Alexa Fluor 488 conjugated anti-E. coli, anti-Syndecan 1 or anti-Syndecan 2 antibody.

FIG. 24 is a graphical illustration (2401) of fluorescence image analysis of murine colorectal tissue stained with Alexa Fluor 488 conjugated anti-E. coli, anti-Syndecan 1 or anti-Syndecan 2 antibody. Fluorescence images were evaluated by measuring the corrected total fluorescence for DAPI, GFP and RFP. The values are expressed as GFP or RFP emission per unit DAPI, where $*p \leq 0.05$, $p \leq 0.01$, $*p \leq 0.001$, NS represents non-significant (n=10 independent experiments, each measurement performed in triplicates; mean s.d.).

Figure 25A:
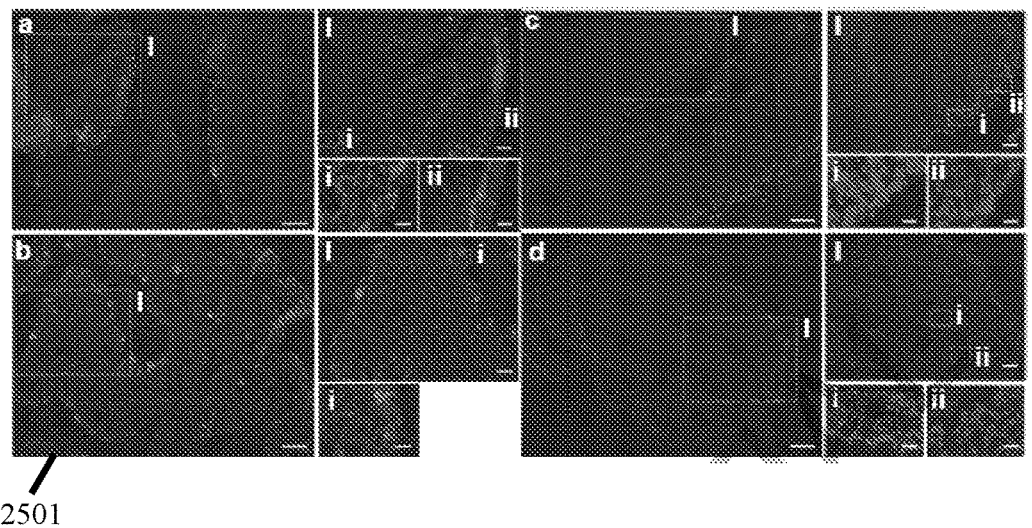
FIG. 25(a) show pictorial representation of histology of colorectal tissue from AOM/DSS treated and untreated mice stained with GFP-HlpA or GFP.

FIG. 25a is a pictorial illustration (2501) of histology of colorectal tissue from AOM/DSS treated and untreated mice stained with GFP-HlpA or GFP. Section a illustrates issue section with DAPI-stained nucleus(blue) from mouse treated with AOM/DSS stained with GFP-HlpA (green), scale bar: 10 mm. Section b illustrates tissue section with DAPI-stained nucleus(blue) from mouse not treated with AOM/DSS stained with GFP-HlpA (green), scale bar: 10 mm. Area c details tissue section with DAPI-stained nucleus (blue) from mouse treated with AOM/DSS stained with GFP (green), scale bar: 10 mm. Panel d details tissue section with DAPI-stained nucleus (blue) from mouse not treated with AOM/DSS stained with GFP (green), scale bar: 10 mm (inset: boxes I-II indicate 20× objective magnification, scale bar: 20 Boxes i-ii indicate 100× objective magnification, scale bar: 100 μm) (red dotted lines annotates the tumor tissue).

Figure 25B:
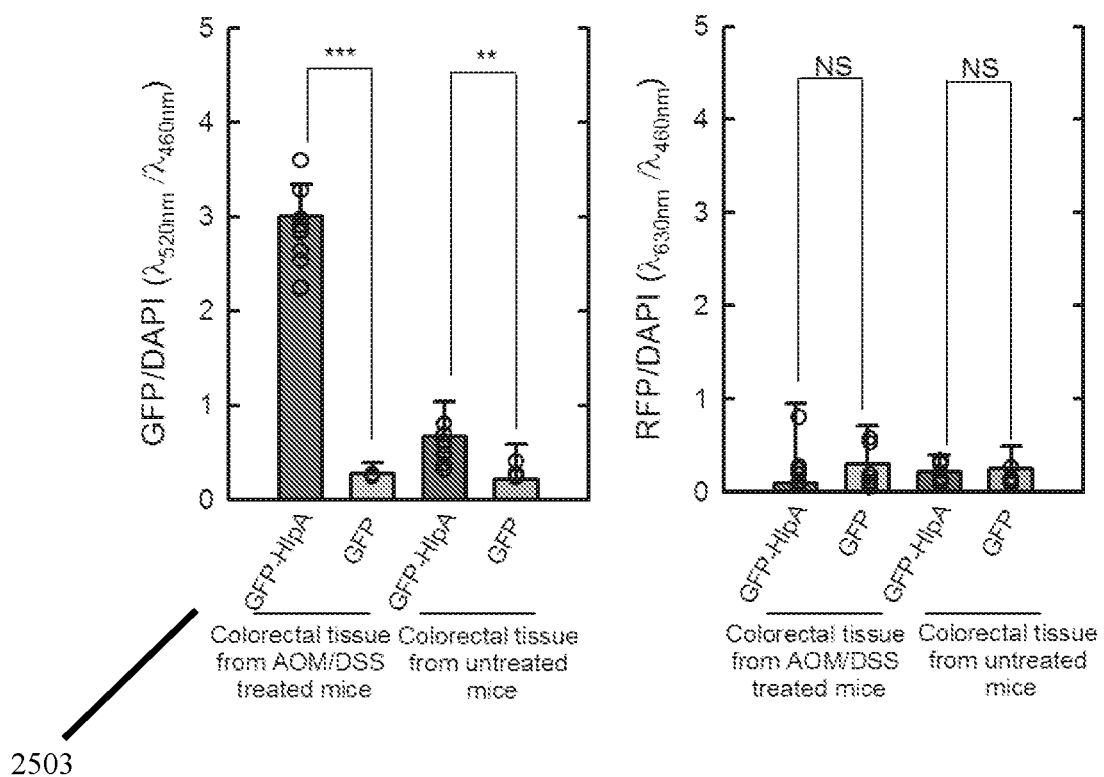
FIG. 25(b) show graphical illustrations of corrected total fluorescence for DAPI, GFP and RFP.

FIG. 25b is a graphical illustration (2503) wherein fluorescence images are evaluated by measuring the corrected total fluorescence for DAPI, GFP and RFP. The values are expressed as GFP or RFP emission per unit DAPI, where *p ≤ 0.05, p ≤ 0.01, *p ≤ 0.001, NS represents non-significant (n=10 independent experiments, each measurement performed in triplicates; mean±s.d.).

Figure 26:
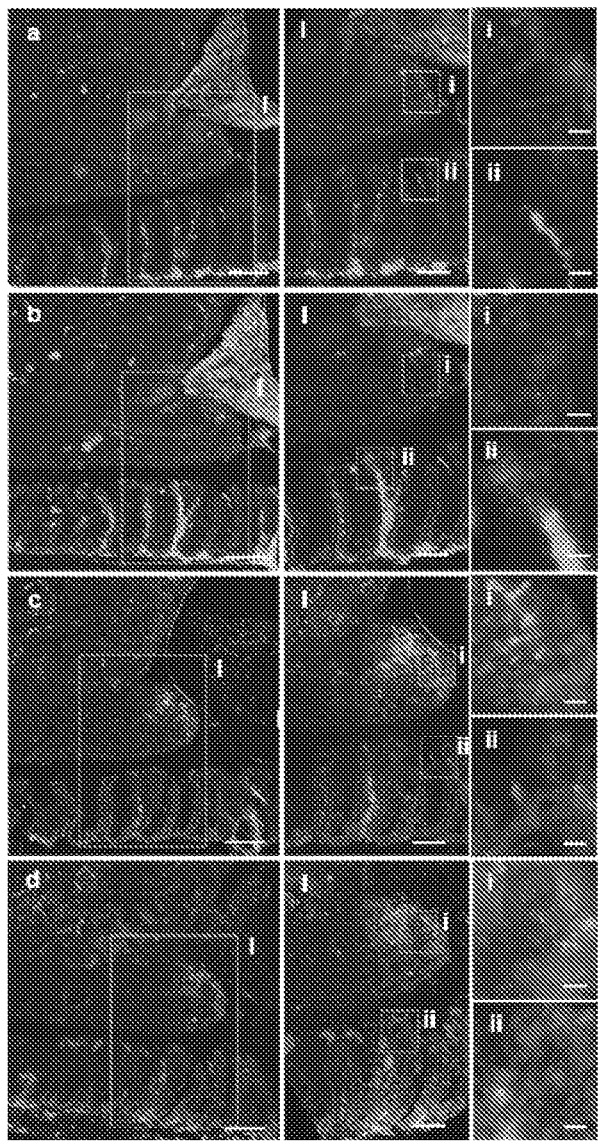
FIG. 26 is a pictorial representation of histology of colorectal tissue from AOM/DSS treated mouse incubated with E. coli Nissle (EcN) expressing RFP with or without INP-HlpA, co-stained with Alexa Fluor 488 conjugated anti-Syndecan 1 or anti-Syndecan 2 antibody.

FIG. 26 is a pictorial representation (2601) of histology of colorectal tissue from AOM/DSS treated mouse incubated with *E. coli* Nissle (EcN) expressing RFP with or without INP-HlpA, co-stained with Alexa Fluor 488 conjugated anti-Syndecan 1 or anti-Syndecan 2 antibody. Alexa Fluor 488 conjugated anti-Syndecan 1 (green) stained tissue sections from mouse treated with AOM/184 DSS incubated with a. RFP expressing EcN (red) and b. INP-HlpA expressing EcN (red). Alexa Fluor 488 conjugated anti-Syndecan 2 (green) stained tissue sections from mouse treated with AOM/DSS incubated with c. RFP expressing EcN (red) and d. INP-HlpA expressing EcN (red). All nucleus in tissue sections were stained with DAPI (blue). scale bar: 10 mm (inset: boxes I-II indicate 20× objective magnification, scale bar: 20 Boxes i-ii indicate 100× objective magnification, scale bar: 100 μm). Fluorescence image analysis is shown in FIG. 28.

Figure 27:
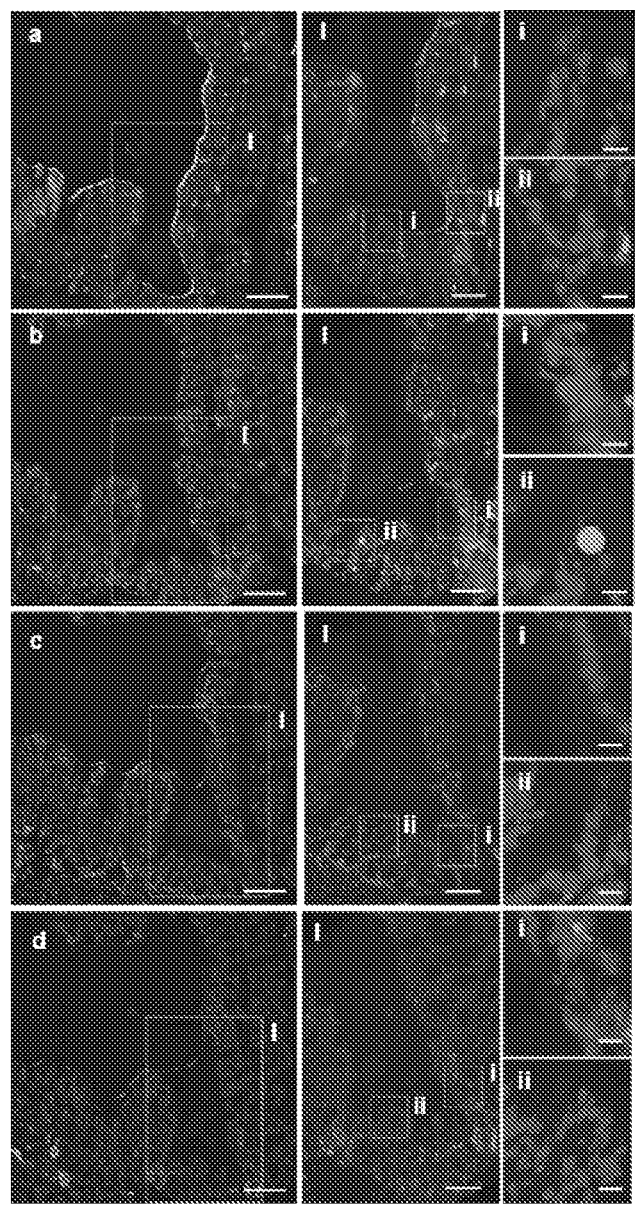
FIG. 27 is a pictorial representation of histology of colorectal tissue from untreated mouse incubated with E. coli Nissle (EcN) expressing RFP with or without INP-HlpA, co-stained with Alexa Fluor 488 conjugated anti-Syndecan 1 or anti-Syndecan 2 antibody.

FIG. 27 is a pictorial representation (2701) of histology of colorectal tissue from untreated mouse incubated with *E. coli* Nissle (EcN) expressing RFP with or without INP-HlpA, co-stained with Alexa Fluor 488 conjugated anti-Syndecan 1 or anti-Syndecan 2 antibody. Alexa Fluor 488 conjugated anti-Syndecan 1 (green) stained tissue sections from untreated mouse incubated with a. RFP expressing 196 EcN (red) and b. INP-HlpA expressing EcN (red). Alexa Fluor 488 conjugated anti-Syndecan 2 (green) stained tissue sections from untreated mouse incubated with c. RFP expressing EcN (red) and d. INP-HlpA expressing EcN (red). All nucleus in tissue sections were stained with DAPI (blue). scale bar: 10 mm (inset: boxes I-II indicate 20× objective magnification, scale bar: 20 μm. Boxes i-ii indicate 100× objective magnification, scale bar: 100 μm). Fluorescence image analysis is shown in FIG. 28.

Figure 28:
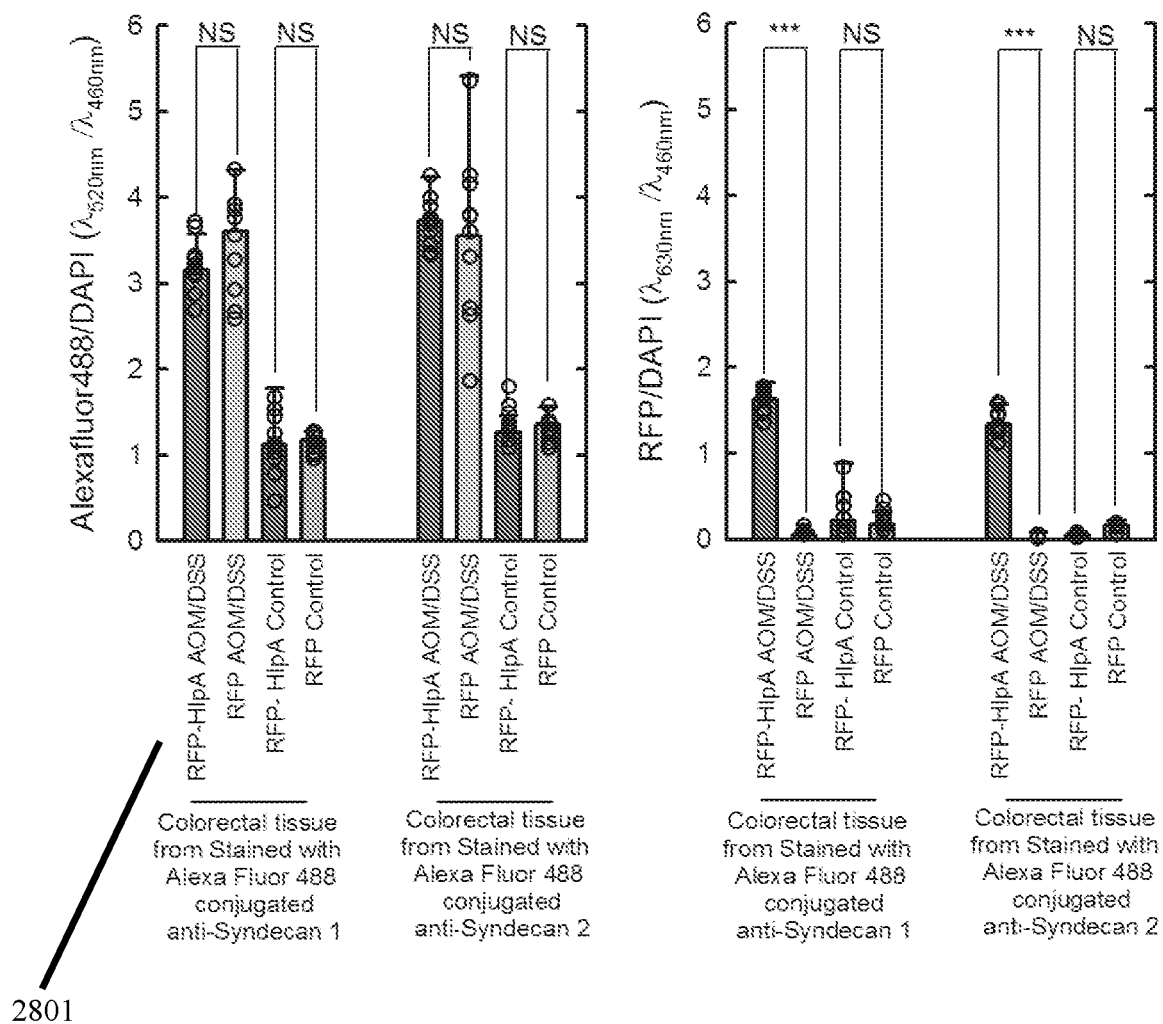
FIG. 28 is a pictorial representation of fluorescence image analysis of murine colorectal tissue incubated with E. coli Nissle (EcN) expressing RFP with or without INP-HlpA, co-stained with Alexa Fluor 488 conjugated anti-Syndecan 1 or anti-Syndecan 2 antibody.

FIG. 28 is a graphical illustration (2803) of fluorescence image analysis of murine colorectal tissue incubated with *E. coli* Nissle (EcN) expressing RFP with or without INP-HlpA, co-stained with Alexa Fluor 488 conjugated anti-Syndecan 1 or anti-Syndecan 2 antibody. Fluorescence images were evaluated by measuring the corrected total fluorescence for DAPI, GFP and RFP. The values are expressed as GFP or RFP emission per unit DAPI, where *p ≤ 0.05, p ≤ 0.01, *p ≤ 0.001, NS represents non-significant (n=10 independent experiments, each measurement performed in triplicates; mean±s.d.).

Example 3

Figure 29:
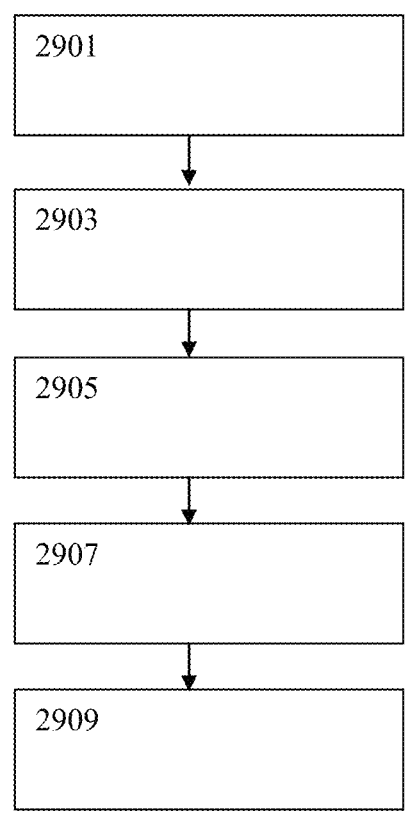
FIG. 29 is a flowchart illustrating a preferred embodiment of the claimed invention.

FIG. 29 depicts a method for colorectal cancer prevention comprising the steps of: Administering (2901) *Escherichia coli* Nissle 1917 (EcN) reengineered to bind to the heparan sulfate proteoglycan (HSPG) on cancer cell surface and reengineered to secrete myrosinase for conversion of dietary-glucosinolate to sulforaphane and Ingesting (2903) cruciferous vegetables adequate to initiate a therapeutic response against colorectal cancer.

FIG. 30 is an Illustrative Representation of DNA construct Seq. ID No 1. FIG. 30 Sequence guide key: Myrosinase I1 (underline), Ice-nucleating protein leader sequence (double underline), Promoter region (bold), YebF secretion tag (italics), Restriction sites (grey background) Histone-like protein A (dashed underline), Double terminator (bold italics), Ribosomal Binding site (dotted underline bold).

FIG. 31 Illustrative Representation of Genetic Sequence of Protein Construct INP-HlpA Seq. ID No 2.

FIG. 32 Illustrative Representation of Genetic Sequence of Construct YebF-I1 Seq. ID No 3.

Example 4

Results

Figure 2A:
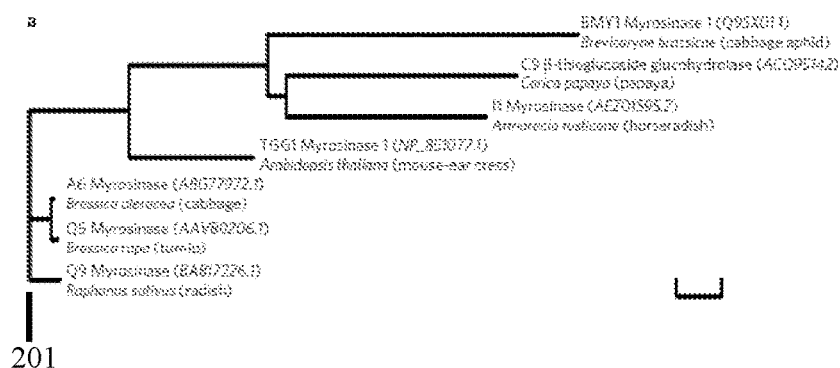
FIG. 2(*a*) is a top level schematic illustration of selected myrosinases.
Figure 2B:
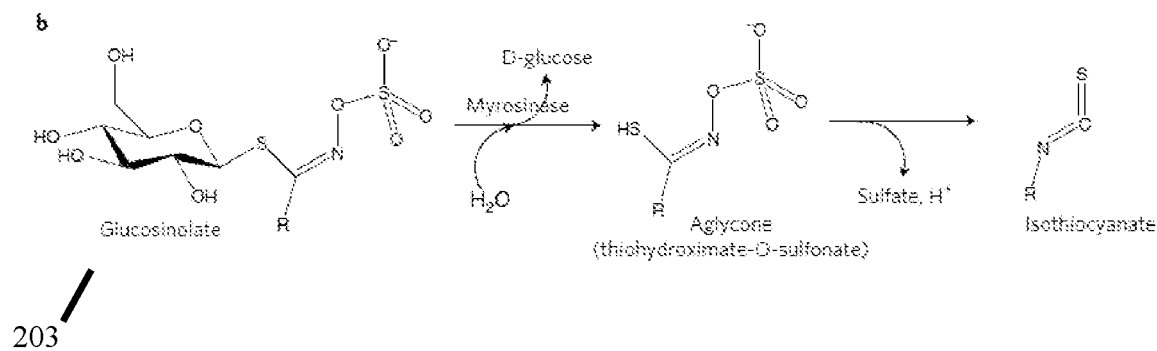

Screening for improved β-thioglucosidase. The activity and stability of myrosinase, a β-thioglucosidase that hydrolyzes glucosinolate to sulforaphane, varies at differing pH and temperature; in a preferred embodiment the selected enzyme needs to function under physiological colorectal conditions. The healthy colon pH averages 6.6, while it is 7.0 and 6.7 in patients with adenoma and carcinoma, respectively. In addition, the temperature of the human intestinal tract ranges from 36° C. to 40° C. depending on the individual's metabolic state. In the illustrative example five plant-derived myrosinase orthologues with minimal glycosylation sites and the absence of the co-factor-binding sites using the BLAST search and the Enzyme Function Initiative—Enzyme Similarity Tool (EFI-EST), are compared to the well-characterized myrosinases from Brevicoryne brassicae (BMY1) and Arabidopsis thaliana (TGG1) (FIG. 2a and FIG. 7).

Figure 2C:
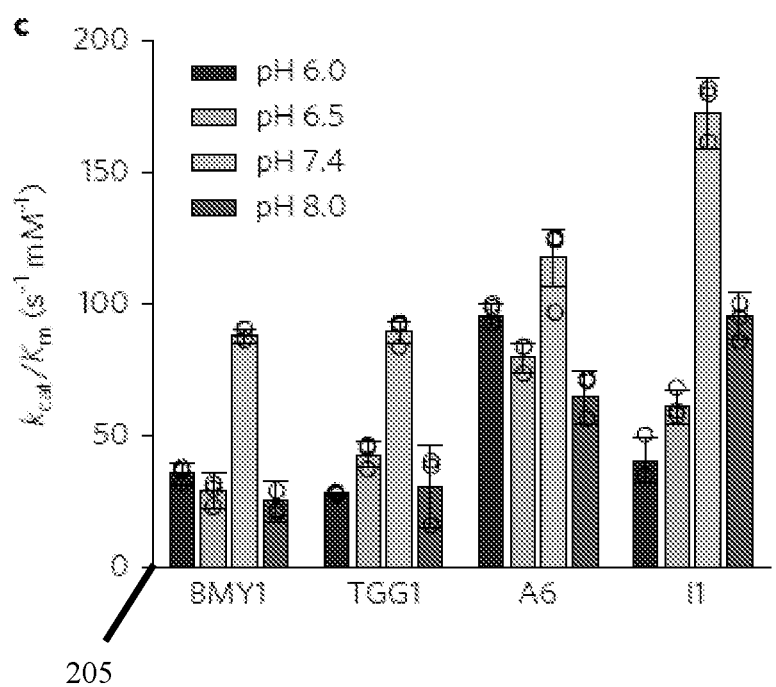
Figure 2D:
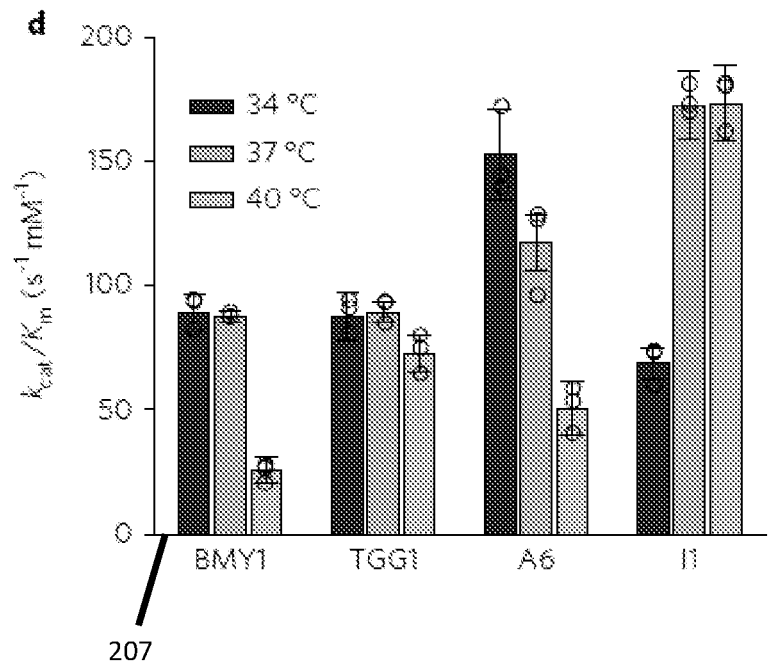

In a preferred embodiment, the myrosinases derived from Armoracia rusticana (I1) and Brassica oleacea (A6) have a better stability and catalytic efficiency in various temperatures and pH values when compared with those derived from BMY1 and TGG1 (Table 1). In a preferred illustrative embodiment I1 myrosinase is selected owing to its Km value and improved kcat at the colorectal ambient temperature and pH (FIG. 2c, 2d and Table 1). By comparing the modeled-I1 myrosinase protein structure against that of the BMY1 myrosinase, the critical side chain residues involved in glucose-ring recognition and the glutamic acid that served as a nucleophile during catalysis are conserved. According to the claimed invention the improved catalytic efficiency of the I1 myrosinase is correlated to its pI value (pI=7.90) and the overall positively charged surface (FIG. 8) that contributes to better structural stability.

Growth-inhibitory activity of L-sulforaphane and allyl isothiocyanate (AITC). To understand the efficiency of I1 myrosinase in facilitating cancer cell inhibition the illustrative example validates the anticancer activity of L-sulforaphane and AITC. Growth inhibition is observed in various colorectal, gastric and breast cancer cell lines within 24 hours upon adding L-sulforaphane, with 50% growth inhibition (GI50) values below 100 μM (Table 2a). AITC, another isothiocyanate produced from sinigrin (horseradish glucosinolate) hydrolysis, additionally inhibits cancer cell growth at a poorer efficacy compared with L-sulforaphane due to its hydrophobic nature. Sinigrin is used as substrate for the myrosinase activity assay as it is commercially available and the resulting product AITC presents similar biochemical properties to sulforaphane. AITC yields GI50 values of approximately 100 μM, exhibiting a full inhibitory effect within 24 hours (Table 2b). L-Sulforaphane and AITC does not inhibit primary smooth muscle cells. In the final construct according to a preferred embodiment, the myrosinase is secreted into the extracellular milieu using a YebF-secretion tag. Cancer cell lines are incubated with the purified YebF-I1 fusion protein and sinigrin to evaluate the anticancer activity of catalyzed-AITC. The YebF-I1 myrosinase was able to convert the supplemented sinigrin to AITC, achieving complete inhibition within 24 hours in all cancer cell lines tested, while showing no inhibition against the tested primary smooth muscle cell line (Table 2c).

Development of the surface-binding module for CRC cell adhesion. In a preferred embodiment, commensal microbes are designed to bind to the upregulated tumor surface HSPG, rendered accessible following the loss of apico-basal polarity in the colorectal epithelial cells and changes in syndecan (1&2) expression during carcinogenesis. The increase in surface HSPG is linked to the dysregulation of the human-derived sulfatases, Sulf-1 and Sulf-2, promoting an increase in sulfation status of HSPG during carcinogenesis.

Histone-like protein A (HlpA) from Streptococcus gallolyticus is responsible for the microbial infiltration into the tumor mass by binding to HSPG, particularly syndecan 1 on the tumor surface. The binding efficiency of EcN purified N-terminal GFP-HlpA is determined for cancer cells based on the emission ratio of GFP against the 4',6-diamidino-2-phenylindole (DAPI)-stained nucleus. The HlpA fusion protein is bound to both human (LoVo and HCT116) and murine (CT26) colorectal cell lines at sub-micromolar affinity (FIG. 3a, 3b, FIG. 9, 10). GFP-HlpA is also bound to smooth muscle cells, though at a 6-fold weaker binding affinity. No binding to gastric (AGS) or breast (MCF7) cancer cell lines is found. An ice nuclease protein (INP) tag is used to export the HlpA binding protein to the EcN surface to facilitate cancer cell adhesion. The HSPG-rich surface regions on the cancer cells is mapped with Alexafluor-488-conjugated anti-HSPG antibodies. The EcN cells expressing INP-HlpA did bind to the HSPG-dense regions on colorectal adenocarcinoma cells and smooth muscle cells (FIG. 3C, FIG. 11). Cancer cells interacted with the engineered EcN at ratios of 1:10 to 1:20 based on the fluorescence assay (FIG. 12). Bacterial cell-expressed surface-presenting INP-HlpA is bound to CRC cells, validating its functionality.

Development of the functional engineered commensal microbe. INP-HlpA and YebF-I1 expression is controlled in the engineered microbes (Eda-I1-HlpA) using the J23105 and J23108 constitutive promoters, respectively (FIG. 4a), with an alanine auxotrophic marker and by cloning into an alanine-deficient E. coli Nissle strain (Eda). These microbes bind specifically to CRC cells and convert the surrounding glucosinolate to sulforaphane. The constitutive expression of the binding module and the secretion of the YebF-I1 myrosinase in the cellular lysate and the extracellular milieu (FIG. 4b, FIG. 13) is validated. The adherence of Eda-I1-HlpA on cancer cells coupled with YebF-I1 secretion facilitates the local catalysis of glucosinolate to sulforaphane, improving sulforaphane delivery to the cancer cells. When the Eda-I1-HlpA microbes are introduced to cancer cells in the presence of sinigrin, there is a clearance of greater than 95% of the CRC cells, with no inhibition in breast, stomach, or primary cell lines (FIG. 4c, 4d and FIG. 14). According to the claimed invention, Eda-I1-HlpA coupled with glucosinolate is a potent and selective inhibitor against CRC cells.

Testing of Eda-I1-HlpA in murine CRC models. To validate the efficacy of the engineered microbes in vivo, Eda-I1-HlpA is administered to Balb/C mice induced with a combination of carcinogenic azoxymethane (AOM) and colitis-inducing dextran sodium sulfate salt (DSS) over a period of 14 weeks (FIG. 5a). To determine Eda-I1-HlpA localization in the bowel, in an illustrative embodiment fecal matter is collected on a weekly basis at three hours post-gavage and four days post-gavage. The colony forming units (CFU)/g of Eda-I1-HlpA in the fecal matter collected from three hours post-gavage are inversely proportional to the number of Eda-I1-HlpA that adhered to the afflicted colorectal region of the mice (FIG. 5b), while the CFU/g from four days post-gavage represent the amount of Eda-I1-HlpA colonized in the colorectal region (FIG. 5c).

Upon each DSS challenge (FIG. 5b, 5c, annotated with the dashed lines), increases in the localization and colonization of Eda-I1-HlpA in mice fed with or without a supplemented diet (broccoli feed or sinigrin supplemented water) is observed. Eda-I1-HlpA-fed mice with the supplemented diet had reduced Eda-I1-HlpA localization and colonization in the colorectal region, indicating tumor regression. The observation is based on the increasing CFU/g of Eda-I1-HlpA fecal matter isolates from three hours post gavage from mice fed with the supplemented diet, indicating fewer colorectal surfaces for Eda-I1-HlpA cell binding (FIG. 5b). Similarly, the decrease in Eda-I1-HlpA isolated from fecal matter collected four days post-gavage (FIG. 5c) indicates lesser Eda-I1-HlpA colonization in the colorectal tract. Non-adherent I1-secreting Eda cells (Eda-I1) maintained an average CFU/g of 103 to 104, consistent with the basal number of EcN that can colonize the colorectal tract of a mouse. The Eda-I1-HlpA profile coincides with the rectal bleeding occurrence observed in Eda-I1-HlpA-treated mice fed with the supplemented diet (FIG. 5d). Eda-I1-HlpA-fed mice show rectal bleeding recovery within 14 days post-DSS treatment, while the Eda-I1-fed mice required a longer recovery period (FIG. 16). The control groups demonstrate persistent occurrence of blood in the fecal matter. No significant changes in weight loss from all test groups is observed according to the claimed invention. The rectal bleeding is indicative of colitis and tumor mass formation in the colorectal tissue caused by damaged colorectal epithelial lining resulting from bowel movement. The reduced incidences of rectal bleeding suggest the recovery of epithelial tissue and reduced tumor size in the colorectal tissue.

Figure 6A:
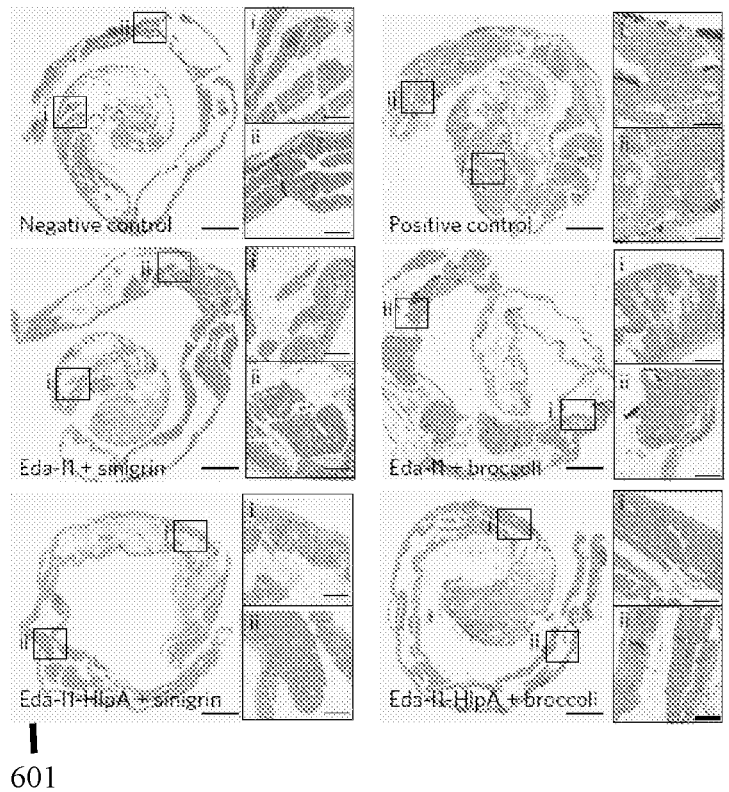
FIG. 6(a) is a pictorial representation of colorectal tissue.
Figure 6B:
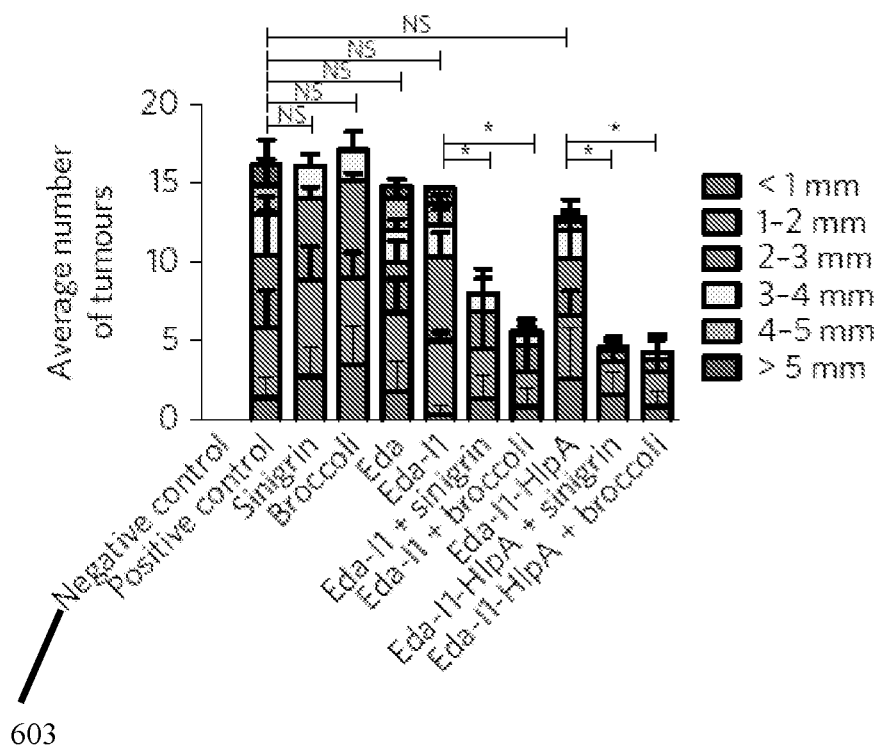
FIG. 6(b) is a graphical illustration of tumor sizes.
Figure 6C:
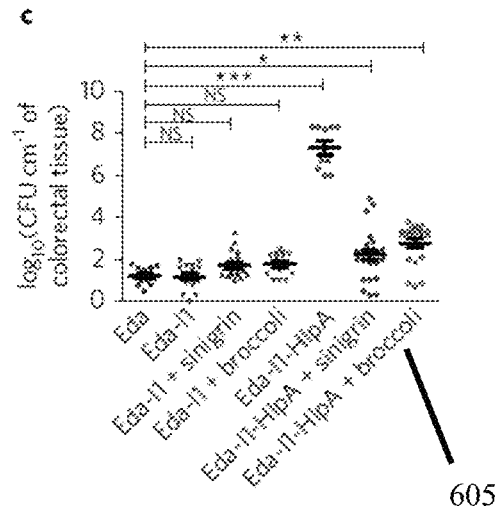
FIG. 6(c) is a graphical illustration of colorectal tissue characteristics.
Figure 6D:
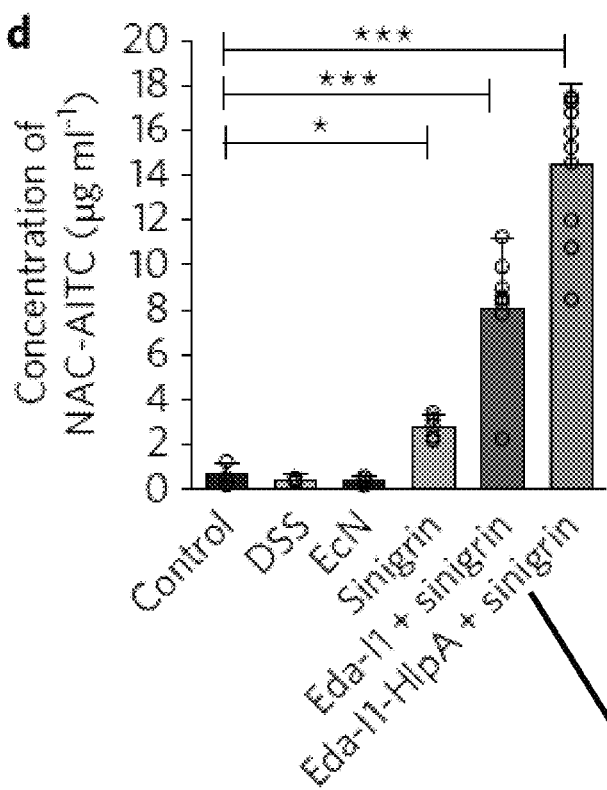
FIG. 6(d) is a graphical illustration of blood serum concentration.
Figure 6E:
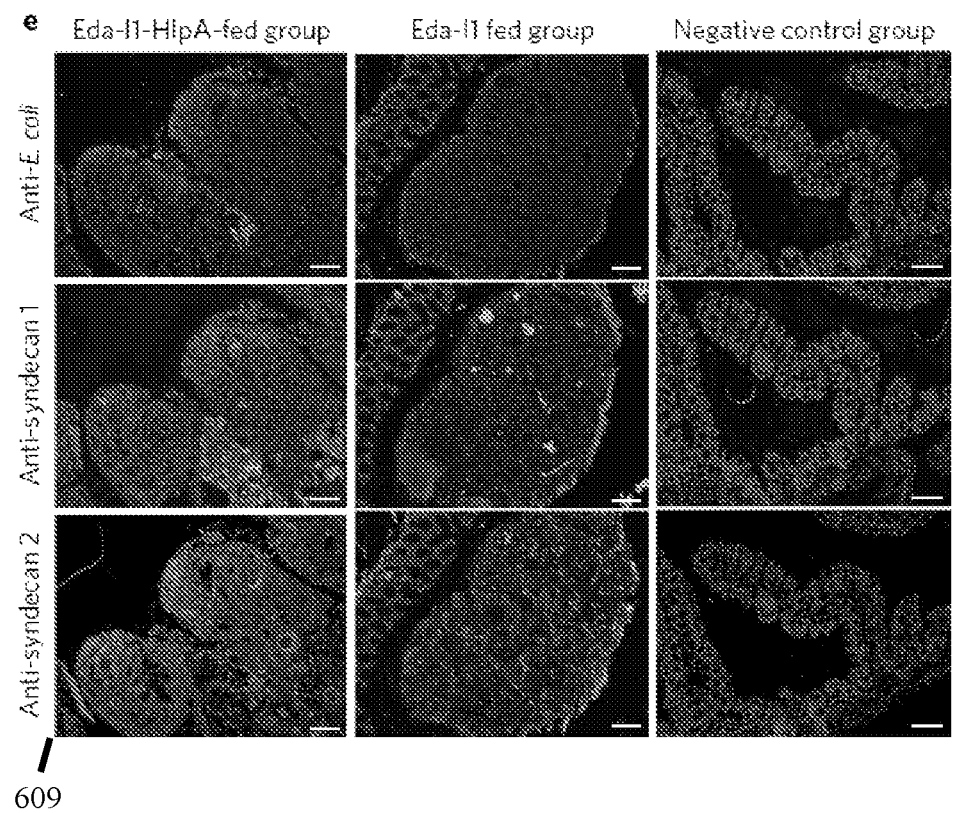
FIG. 6(e) is a pictorial representation of colorectal tissue.
Figure 6F:
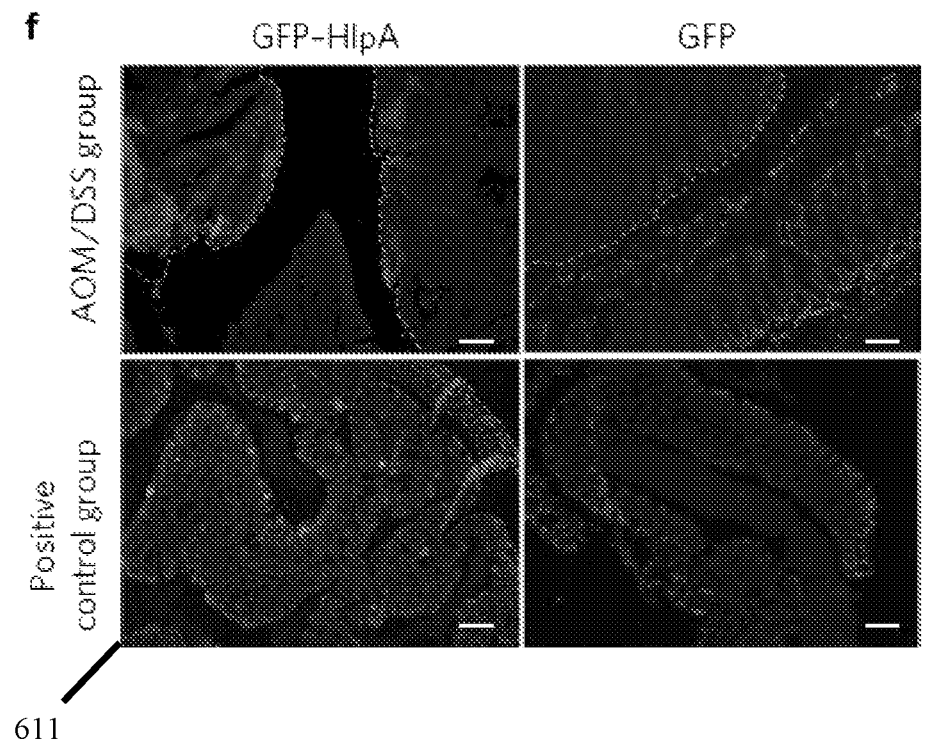
FIG. 6(f) is a pictorial representation of colorectal tissue.
Figure 6G:
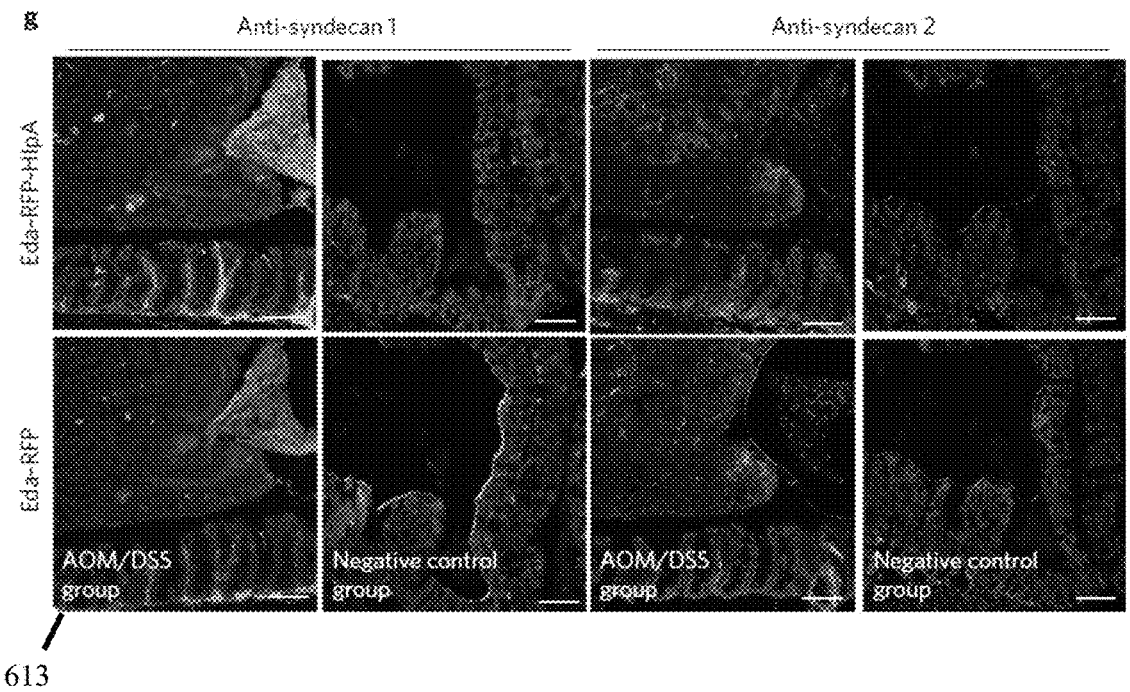
FIG. 6(g) is a pictorial representation of colorectal tissue.

In an illustrative embodiment, the colorectal tissue and blood serum is collected at the 180 end of the 14th week for histological studies and adhesion analysis. The mice are sacrificed a week after the last oral gavage and six weeks from the last DSS treatment. Histological analysis of the colorectal tissue using hematoxylin and eosin (H&E) staining showed fewer and smaller tumors in mice fed with Eda-I1-HlpA and broccoli/sinigrin. Approximately 75% fewer tumors than in the positive controls are observed, with an average tumor diameter of 2 mm (FIG. 6a, 6b). Upon closer inspection, the colorectal tissue of mice fed with Eda-I1-HlpA and the supplemented diet show colonic mucosal hyperplasia or mild dysplasia with no visible colorectal tract obstruction compared to the controls. These colorectal tissues had increased gut associated lymphoid tissue (GALT) that might result from a sulforaphane-mediated immune response (FIG. 17). In contrast with the Eda-I1-HlpA and dietary supplemented group, the mice not fed the Eda-I1-HlpA or supplemented diet show severe dysplasia with differentiated glandular tumor masses that formed outwards towards the lumen. No tumor invasion into the mucosa, submucosa or the muscularis propria is observed, consistent with the established AOM/DSS protocols (FIG. 18). Furthermore, approximately 107~108 CFU of Eda-I1-HlpA per cm of colorectal tissue homogenate from mice with the normal diet is found, while mice with the supplement diet have approximately 103~104 cells bound, indicating reduced Eda-I1-HlpA binding surface resulting from sulforaphane inhibition (FIG. 6c). Mice treated with Eda-I1 show a reduced count by up to 60%, with a mean tumor diameter of 3 mm; however, these results are not as significant as those from the Eda-I1-HlpA treatment (FIG. 6a, 6b, FIG. 19). Multiple incidences of mild to moderate dysplasia is observed, mainly with tumors developing at the distal end of the colorectal tissue. The presence of Eda-I1-HlpA cells bound on tumor surfaces is demonstrated using immunofluorescence staining. An increased number of surface bound E. coli cells in mice fed with Eda-I1-HlpA is observed as compared to those fed with Eda-I1. Increased levels of Syndecan 1 and 2 is noted at Eda-I1-HlpA adhered regions (FIG. 6e, FIG. 21-24). The binding function of Eda-I1-HlpA is hereby confirmed though interaction of the microbes to colorectal cancer tissues. The binding of GFP-HlpA to sectioned tissues is tested and observed that HlpA specifically interacts with HSPG-rich areas (FIG. 6e, 6f, FIGS. 21 and 25). As shown in FIG. 6e and FIG. 21, an increase of non-localized Syndecan 1 and 2 on tumor surfaces is observed. The Syndecan 1 and 2 localization profile is compared to GFP HlpA-stained colorectal tissues and an increased localization of GFP-HlpA in colorectal tissue from the AOM/DSS group compared to the untreated group that showed similar localization profile to Syndecan 1 and 2 (FIG. 6f and FIG. 25) is found. The tumor surface HSPG is sufficient for cancer cell adherence by ex-vivo microbial adherence and is hereby demonstrated.

According to the claimed invention, an accumulation of E. coli Nissle (expressing RFP and surface presenting HlpA) specifically localizes on the HSPG-rich tumor surface when the tissue sections were incubated with Eda-I1-HlpA (FIG. 6g and FIG. 26-28). To demonstrate the increased conversion of dietary glucosinolates, the serum profile of mice fed with sinigrin in drinking water is analyzed.

The unused AITC converted by the myrosinase I1 is absorbed into the blood stream, conjugating to glutathione, before finally converting to N-acetyl-cysteine conjugated AITC (NAC-AITC), which is eliminated through the kidneys. Through liquid chromatography tandem mass spectrometry and high performance liquid chromatography, the presence of NAC-AITC in the mice serum (FIG. 6d and FIG. 20) is detected. The concentration of NAC-AITC is twofold higher when mice are fed with the adherent Eda-I1-HlpA compared to Eda-I1. This finding indicates that Eda-I1-HlpA microbes are able to adhere on to the tumor surface and this adherence facilitates the increased conversion of glucosinolates to sulforaphane.

In summary, according to the claimed invention Eda-I1-HlpA coupled with dietary glucosinolate significantly reduces the risk of tumor development. The specific recognition of the surface HlpA enables the engineered microbes to bind on the tumor surfaces, while the secreted myrosinase leads to increased conversion of glucosinolate to sulforaphane for active uptake into the cancer cells. This leads to over 75% tumor reduction in the colorectal region in induced-CRC mice. According to the claimed invention, Eda-I1-HlpA treatment inhibits cancer cell development using glucosinolates originating from supplemented drinking water or cruciferous vegetables.

Discussion

The occurrence of CRC, particularly in older patients, often results from the weakening of host immunity, changes in lifestyle and the cumulative effect of dietary patterns. Changes in diet and lifestyle can reduce the risk of developing colorectal-related illnesses (e.g., inflammatory bowel disease [IBD], Crohn's disease, etc.). Natural dietary metabolites are targeted for the claimed invention CRC chemopreventive strategy because they could form the basis of a sustainable long-term therapeutic regimen. While E. coli Nissle 1917 is utilized as the microbial chassis due to its cellular capacity to prevent inflammatory bowel disease and its ability to colonize the colon region, it is a direct and intended consequence of the claimed invention that additional embodiments include additional genetic chassis variants. While the concept of microbial synthesis and secretion of anticancer compounds is an attractive option for targeted drug delivery, it has its limitations. Such limitations include the cell count-dependent and undefined dosage of the cell-synthesized drug in the colorectal tract, the cellular metabolic state, and the precursor bioavailability for anticancer compound synthesis. The undefined dosage of the anticancer compound might be ineffective against cancer cells below the effective concentration, while overdosing might result in host cell toxicity. To overcome these limitations, myrosinase and cruciferous plant-derived glucosinolates is utilized for cancer cell cycle inhibition and induction of apoptosis. This choice is due to the nature of glucosinolates from ingested plants, which is poorly absorbed by cancer cells because of the sugar moiety that improves its solubility. While the host microbiota facilitates glucosinolate conversion, the catalytic turnover when unaided by the claimed invention is inadequate to elicit anticancer effects. Furthermore, sulforaphane does not affect primary stem cells or other non-cancer cell lines, and mammalian cells do not have the capacity to convert these compounds, which makes this myrosinase-glucosinolate combination a potential tool for the targeting of cancer cells.

Further illustrations of the claimed targeted delivery of sulforaphane centers on cellular adherence to the CRC cell surface: although various genera of bacteria are known to have cancer cell adhesion, such as Faecalibacterium, Dorea and Ruminococcus, little effort has been made to mimic this behavior for directed targeting. The microbes target various CRC biomarkers, such as HSPG, insulin like growth factor-I, mucin, and vascular endothelial growth factor (VEGF). HSPG is upregulated from the time of initial carcinogenesis in dysplastic and neoplastic cells to fully developed tumors, making HSPG an ideal target for preventive therapy. The claimed Eda-I1-HlpA microbes express the Staphylococcus gallolyticus-derived HlpA to bind discriminatively to the HSPG-rich regions of colorectal adenocarcinoma cells both in vitro and in vivo. The tumor-binding is surface-dependent, resulting in the detachment of Eda-I1-HlpA from the colorectum as the tumor regresses. According to embodiments of the claimed invention, cancer targeting by surface biomarker recognition and binding for targeted therapy is demonstrated using engineered commensal microbes. Utilizing an auxotrophic marker system, the binding module is constitutively expressed and the secretion of the I1 myrosinase in alanine-deficient E. coli Nissle (Eda) is demonstrated. According to the claimed invention, Eda-I1-HlpA induces greater than 95% CRC cell death in the presence of a glucosinolate precursor in vitro. Eda-I1-HlpA fed to mice in a CRC model with a cruciferous diet results in smaller and fewer tumors compared to the positive controls (mice fed with broccoli only, the engineered microbes only or standard feed without engineered microbes). Eda-I1-HlpA-fed mice with cruciferous vegetables show the strongest tumor reduction, twofold higher than in Eda-I1-fed mice with cruciferous vegetables. This result is concomitant with the twofold increase in NAC-AITC levels in the serum of mice fed with Eda-I1-HlpA than that of mice fed with Eda-I1.

In some cases there is a slight tumor count reduction in mice fed with any form of *E. coli* Nissle, possibly attributable to the bacterium's innate capacity to suppress colitis. Additionally, the use of Eda-I1-HlpA facilitates rapid rectal bleeding recovery, suggesting the suppression of the tumor formation and the recovery of damaged epithelial tissues. Based on the colorectal tissue immunofluorescence staining, retrieval of engineered microbes from tissue samples and harvested serum derived-AITC; it is demonstrated that Eda-I1-HlpA adheres to the tumor surface, facilitating the conversion of ingested glucosinolates to supply a higher localized sulforaphane concentration for tumor absorption, inhibiting tumor cell proliferation and aiding in colorectal tumor regression. The low levels of surface HSPG that are present in healthy epithelial tissues in the GI tract might be weak binding sites for Eda-I1-HlpA to result in off-target conversion of glucosinolates.

Given that the average intake of glucosinolates is two order of magnitude lower than the lethal dosage of isothiocyanatesl 1 (LD50=339 mg/kg body weight in murine models) any off-target conversion is unlikely to result in deleterious effects to the host. When utilizing traditional therapeutic strategies, significant but variable clinical outcome is observed in patients with advanced-stage cancers following targeted therapies, including anti-angiogenic antibodies, small molecular weight kinase inhibitors and checkpoint inhibitor-based immunotherapy. While stage 1 CRC patients benefit from surgery, more advanced CRCs are offered neo-adjuvant or adjuvant chemotherapy that yields a variable degree of curative effects. Similarly, targeted therapies and immunotherapies remain ineffective, resulting in the need for new approaches for colorectal cancer treatment which make the claimed invention highly relevant and desirable. Microbial engineering is an alternative strategy to treat cancer via the secretion of prodrug-cleaving enzymes, α-hemolysin, immunomodulatory proteins, cytokines, and toxins; however, these drugs could result in undesirable effects on the host at high concentrations. Other efforts use attenuated pathogens, such as *Salmonella typhimurium*, to infiltrate cancerous tissue, which might elicit undesired immune response in immune-compromised patients. The Eda-I1-HlpA capacity to bind to cancer cells specifically ensures recognition and clearance of tumor cells at the initial stages of carcinogenesis. According to embodiments of the claimed invention, clearance of non-invasive tumor masses induced by AOM/DSS treatment is observed, which is suited for pre-tumor masses to stage 1 CRC chemoprevention or complementary therapy used in tandem with conventional chemotherapy or immunotherapy for improved remission of cancers more severe than stage 1. In conclusion, the use of Eda-I1-HlpA is intended as a dietary supplement coupled with a regular cruciferous diet to prevent CRC initiation and development or as a post-operative care supplement to improve patient recovery. The anticancer effect is regulated by adjusting the cruciferous vegetable portion consumed by the host, translating to improved biosafety for patient consumption.

Example 3

Methods

Gene cloning, protein expression and purification. Myrosinase genes are optimized for *E. coli* expression and cloned into the pET28b expression vector. The plasmids are transformed into *E. coli* BL21 (DE3) cultured in lysogeny broth (LB) (BD, Le Pont de Claix, France) at 37° C., 225 rpm to OD600 0.6 followed by 0.5 mM isopropyl β-D-1-thiogalactopyranoside (IPTG) induction at 16° C., 180 rpm for 16 hours. Cells are harvested, resuspended in lysis buffer (50 mM Tris-Cl, 300 mM NaCl, 10% glycerol, 1 mM dithiothreitol [DTT], pH 8.0) and lysed using Emulsiflex C-3 (Avestin). Expressed myrosinases are purified by IMAC Ni-NTA purification followed by Hi-Load Superdex 200 size exclusion column chromatography (GE, Uppsala, Sweden). The purified protein is concentrated and stored at −80° C. Pilot scale protein purification and enzymatic assay is conducted.

Myrosinase screening assay. The enzymatic reaction is measured for the release of glucose resulting from sinigrin hydrolysis. The reaction is conducted in sodium phosphate-buffered solution supplied in the Amplex® Red Glucose/Glucose Oxidase Assay Kit (Thermo Fisher Scientific, Geel, Belgium). The reaction buffer is prepared at different pH values (6.0, 6.5, 7.4 and 8.0) and at different reaction temperatures (34° C., 37° C., and 40° C.). The reaction is prepared using 0.1 μM purified myrosinase added to 1× Amplex® Red Glucose Assay reaction mixture and was kick-started with the corresponding concentration of sinigrin. The reaction can be measured at 560 nm absorbance and fluorescence (kex=540 nm, kem=590 nm) using a Synergy H1 Multi-Mode microtiter plate reader (BioTek®, Winooski, USA). The reaction initial velocity (V0) is determined and fitted into a Michaelis-Menten curve. Vmax and KM are determined by fitting into the Michaelis-Menten equation (Eq. 1) using GraphPad Prism Software.

$$\upsilon = V\text{max}*[\text{Sinigrin}]/(K_M+[\text{Sinigrin}]) \quad \text{(Eq. 1)}$$

Cell culture and toxicity assay. While HCT116 human colorectal carcinoma cells (ATCC, Manassas, USA), LoVo human colorectal adenocarcinoma cells (ATCC), AGS human gastric adenocarcinoma cells (ATCC), MCF7 human breast adenocarcinoma cells (ATCC), human esophageal smooth muscle primary cells (SMCs) (Cell Biologics, Chicago, USA) and CT26 mouse colorectal carcinoma cells (ATCC) are used according to the claimed invention, other illustrative cell lines may similarly be utilized. Cells are cleared of mycoplasma contamination prior to use using Mycoalert™ PLUS mycoplasma detection kit (Lonza). HCT116 cells are cultured in McCoy's 5A medium, LoVo and AGS cells in Ham's F12 medium, MCF7 cells in DMEM medium, CT26 cells in RPMI medium, and SMCs in the specific medium kit purchased from Cell Biologics. In this illustrative embodiment, unless otherwise stated all cell culture media are purchased from Lonza (Walkersville, USA) and are supplemented with antibiotics (penicillin/streptomycin) and 5% fetal bovine serum (FBS, v/v). SMCs are prepared according to the manufacturer's protocol. All cell cultures are maintained at 37° C. and 5% CO2. Cells are seeded in 96-well plates or on glass coverslips in 6-well plates at a density of 5×105/well and are cultured at 37° C. and 5% CO2 a day before protein-binding studies or co-culturing with transformed Nissle cells.

The inhibitory assay of L-sulforaphane and AITC is performed by incubating cancer cells grown to 60% confluence with L-sulforaphane or AITC at various concentrations (0.01~5000 μM) in the respective culture medium at 37° C. and 5% CO2. Cellular viability is measured at 3 hours, 24 hours and 72 hours post-treatment using the MTT assay (Sigma, St. Louis, USA). The inhibitory activity of myrosinase-converted AITC is performed by incubating cancer cells grown to 60% confluency with 0.1 μM of purified secreted I1 myrosinase with 0~10 mM sinigrin at 37° C. and 5% CO2 and was sampled at 3 hours, 24 hours and 72 hours post-treatment. The MTT readout is fitted to a dose-response curve to determine the GI50 value (Eq. 2).

$$\text{Absorbance (570 nm)} = \text{Bottom} + (\text{Top}-\text{Bottom})/(1+10^{(([\text{Inhibitor}]-\text{Log 10 GI50})))} \quad \text{(Eq. 2)}$$

HlpA binding assay. The HlpA gene sequence is optimized for *E. coli* expression, and the gene is cloned into a pET28b vector with an N-terminal GFP. GFP-HlpA and GFP are expressed using similar purification protocols, described above. Cell lines grown to 60% confluence in 96-well formats are incubated with the purified N-terminal GFP-tagged HlpA or GFP proteins at varying concentrations (0~10 µM) for 30 minutes at 37° C. and 5% CO2. Treated and adherent cells are washed with sterile PBS twice before staining with DAPI. The GFP/DAPI ratio is used to evaluate the binding ratio of protein binding per cell (Eq. 3).

$$\text{Ratio (GFP/DAPI)} = \text{Bottom} + (\text{Top}-\text{Bottom})/(1+10^{(([\text{Ligand}]-\text{Log 10 KD})))} \quad \text{(Eq. 3)}$$

Similarly, N-terminal INP tagged to HlpA are cloned into the pBbE8K vector and co390 transformed with pBbE8a-RFP into *E. coli* Nissle. *E. coli* cells are cultured in LB supplemented with 50 mg/L ampicillin and 25 mg/L kanamycin and are induced with 1% arabinose. The cells are washed twice with 1×PBS and prepared to a concentration of 109 cells/mL. Cancer cells grown to 60% confluence in 96-well plates are stained with DAPI before incubating with 108 *E. coli* Nissle from the previous step for 30 minutes in 37° C., 5% CO2. The cancer 394 cells are washed twice with 1×PBS and measured for DAPI and RFP emission. The fluorescence emission is compared on the linear standard curve of stained cells against the average fluorescence emission to determine the binding ratio of *E. coli* to cancer cells.

Immunofluorescence microscopy. For the protein binding studies, 200 µM of either purified GFP protein or N-terminal GFP-tagged HlpA protein, or an equal volume of buffer used to dissolve the proteins, is added to the cell culture for 2 h. The culture is then stained with DAPI and washed briefly with 1× PBS before visualization with a fluorescence microscope (Olympus IX81).

For the co-culture studies, Nissle cells expressing either RFP only or both RFP and INP-HlpA are induced with 1% arabinose (w/v) and cultured at 16° C. in a shaking incubator overnight. The cells are then washed twice with 1× PBS, and an OD600 reading was taken to calculate density.

The mammalian cells are briefly washed with 1× PBS before being fixed in chilled methanol for 5 minutes. The cells are then washed with a wash buffer (1× PBS supplemented with 1% Tween 20 and 1% bovine serum albumin [BSA]) and blocked with 1% BSA for 20 minutes. Next, 1×108 *E. coli* Nissle cells are co-cultured with the mammalian cells for 2 h at 37° C. and 5% CO2. The cells are briefly washed thrice with wash buffer and incubated with anti-HSPG antibodies [ab2501] (Abcam, Cambridge, UK) at a dilution of 1/300 at 4° C. overnight on a rotator. The cells are again washed thrice with wash buffer and subsequently incubated with Alexafluor-488-conjugated anti-rat antibodies [ab150157] (Abcam) at a dilution of 1/500 for 1 h at room temperature on a rotator. The cells are briefly washed again before being stained with DAPI and subsequently viewed with a fluorescence microscope.

In vitro assay of functional *E. coli* Nissle 1917. The YebF-I1 myrosinase-expressing gene and the INP-HlpA gene were cloned into a peAlrt plasmid regulated by J23105 and J23108 constitutive promoters, respectively. The gene construct is transformed into an alanine-deficient *E. coli* Nissle (Eda) host. Cancer cells are grown on the top of coverslips in 6-well plates to 80% confluence before adding 107 cells per well for 30 minutes. Coverslips are washed three times with 1× PBS and were returned to the wells inverted. Fresh medium with 1 mM sinigrin was added, and the cells are incubated for 24 hours at 37° C., 5% CO2. Coverslips were washed three times with 1× PBS before being stained with a LIVE/DEAD kit (Life Technologies, Carlsbad, Calif.) and viewed under a fluorescence microscope. For the survival assay, the cells are treated similarly in 96-well plate format and assayed using the MTT assay kit (FIG. 15).

Functional commensal microbial assay in a murine CRC model. In this illustrative embodiment, a total of 10 mice per treatment group and five mice per control group are used. Non-randomized male Balb/c mice (aged 5-6 weeks, weight 18-22 g, InVivos Pte. Ltd, Singapore) used are allowed to acclimatize for three days in animal holding conditions before inclusion in the illustrative embodiment. The selection criteria for the animals are pre-established in advance. For the illustrative example, the mice are divided into various groups, namely negative controls (n=3), AOM only (n=3), DSS only (n=4), AOM/DSS (n=5), AOM/DSS+sinigrin (n=5), AOM/DSS+broccoli (n=5), AOM/DSS+Wild-type EcN 1917 (n=5), AOM/DSS+Eda-I1 (n=5), AOM/DSS+Eda-I1+sinigrin (n=10), AOM/DSS+Eda-I1+broccoli (n=10), AOM/DSS+Eda-I1-HlpA (n=5), AOM/DSS+Eda-I1-HlpA+sinigrin (n=10) and AOM/DSS+Eda-I1-HlpA+broccoli (n=10), totaling 80 mice per experiment. Two biological replicates of the non-blinded animal experiments are conducted with a duration of 16 weeks each. The number of animals per group is chosen as the minimum number required for conclusions of biological significance in consultation with the SingHealth Institutional Animal Care and Use Committee. All animal experiments are conducted in accordance with the guidelines and approval of the SingHealth Institutional Animal Care and Use Committee (2014/SHS/916). The mice are given 0.5% streptomycin sulfate in their drinking water at 10 days prior to azoxymethane injection for 24 hours. Food is denied at 8 days prior to the injection for 18 hours. Food and drinking water are restored at 7 days prior to the injection. On day 0, azoxymethane (10 mg/kg) is administered intraperitoneally to mice in the AOM treatment groups. Mice from the appropriate treatment groups are put on a lyophilized-Australian broccoli/food pellet mixed diet (50%:50%) or are given sinigrin (1 mM) in their drinking water. Mice from the appropriate treatment groups are also orally gavaged with 109 cells of Eda-I1-HlpA or Eda-I1 every seven days from day 7 onwards until the end of the study. On day 7, mice from the appropriate treatment groups are given 2% dextran sodium sulfate (DSS) in their drinking water for seven days, followed by 14 days of drinking water. This DSS cycle is repeated twice for a total of 3 cycles. Fecal matter is collected three hours post-gavage and four days post-gavage. Rectal bleeding and blood on fecal matter is noted. The fecal matter is weighed, and 10 µL of 20% sucrose solution was added for each 1 mg of weight. The fecal matter is vortexed until homogeneous and spun down at 1,000 g for 30 minutes. The supernatant is serially diluted before being spotted on LB plates for CFU counting.

At the end of week 14, the mice are sacrificed, and their colon tissue harvested. One centimeter of distal colorectal tissue is removed and homogenized using a Dounce homogenizer in 1 mL of 20% sucrose. The homogenate is spun down at 1,000 g for 30 minutes before 458 being serially diluted for CFU count. For microscopic examination of colon tissue, the harvested colon tissue is fixed in 10% buffered formalin for 48 hours. The tissue samples are then processed and embedded in paraffin. Sections are cut to a 5-μm thickness using a rotary microtome, mounted on glass slides and stained with H&E. The diameter of tumors and their numbers are calculated before the values are plotted for analysis. For data analysis, the correlation of tumor size to tumor count is determined using ANOVA with Bonferroni correction (overall a level: 0.0083; number of hypotheses: 6). Student's t-test is used in the statistical analysis of microbial cfu /cm of colorectal tissue.

Immunohistochemistry staining and Eda-I1-HlpA binding to mice colorectal tissue. Sectioned tissues mounted on slides are de-paraffinized using Xylene twice for 3 minutes and once with Xylene:Ethanol (1:1) for 3 minutes. Samples are rehydrated by multiple washes using a decreasing concentration of ethanol (100%-50%). Epitope retrieval is accomplished by incubation in sodium citrate buffer (10 mM sodium citrate, 0.05% Tween 20, pH 6.0) for 20 minutes at 95° C. in a pressure cooker. Tissues used for immunohistochemistry staining are incubated with 10 μM GFP-HlpA, 10 μM GFP or primary antibodies targeting various HSPG (Mouse monoclonal to syndecan1 [ab34164]; Rabbit polyclonal to syndecan2 [ab191062]) and Anti-E. coli (Goat polyclonal to E. coli [ab13627]) at 4° C. overnight in a moisture chamber. The slides with primary antibodies are briefly rinsed with distilled water and incubated with the corresponding secondary antibodies conjugated with Alexfluor488 (Goat anti-mouse IgG Alexa Fluor [ab150113]; Goat anti-rabbit IgG AlexaFluor488 [ab150077]; Donkey anti-goat IgG H&L Alexa Fluor 488 [ab150129]) for an hour at room temperature. All slides are briefly rinsed with distilled water and were stained with DAPI prior to viewing under a fluorescence microscope (Olympus IX81). The resulting images are processed and analyzed using ImageJ, in which maximum projections and total fluorescence measurements were performed. Eda-I1-HlpA binding is achieved using the E. coli Nissle strain expressing RFP and Inp-HlpA as described above. The microbial inoculum is prepared as mentioned earlier and the antigen retrieved tissue samples are incubated with the inoculum at 1×106 cells for 30 minutes at 4° C. The slides are rinsed vigorously twice with distilled water and stained with DAPI prior to viewing under a fluorescence microscope.

Analysis of mice serum N-acetyl-cysteine conjugated AITC (NAC-AITC) Mice serum (100 μL) is extracted using 400 μL methanol containing 0.5% formic acid and vortexed for 10 minutes. After centrifugation at 13,000 rpm for 5 minutes, the supernatant was transferred into a clean tube for drying using Vacfuge Centrifugal Vacuum Concentrator (Eppendorf, 491 UK) heated to room temperature. Samples are then reconstituted in 20 μL Acetonitrile 50% and filtered using 0.2 μm cartridge filter (Sartorius). Samples are separated using 1260 Infinity High Performance Liquid Chromatography (Agilent) equipped with Inertsil® ODS-3 5 μm (4.6×250 mm) C-18 column (GL Sciences Inc., Japan). Briefly, 50 μL of samples are injected and separated using an isocratic gradient of 30% Acetonitrile with 0.1% TFA for 25 minutes and detected at 230 nm with reference wavelength of 350 nm. Samples are further analyzed using liquid chromatography tandem mass spectrometry 6550 iFunnel QTOF LC/MS (Agilent) equipped with Eclipse Plus C18 RRHD 1.8 μm (2.1×100 mm) column (Agilent), using the Dual AJS ESI ion source, scanning for positive ion polarity. Briefly, 10 μL of sample is injected into the column and separated using an isocratic run of 5% Acetonitrile with 0.1% formic acid for 2 minutes followed by a gradient increase to 90% Acetonitrile with 0.1% formic acid for a duration of 6 minutes and maintained at 90% for 2 minutes. Ionization profile is detected for mass m/z 407.1056 [M+H+]. The ionization profile correlates the standard NAC-AITC profile. NAC-AITC standards at varying concentrations are used as a reference to quantify the NAC-AITC isolated from the mice serum. Student's t-test is used in the statistical analysis.

TABLE 1

Table S1 | Myrosinase activity assay screening under various pH and temperature conditions (n = 3 independent experiments, each measurement performed in triplicates; mean ± 23 s.d.).

| Myrosinase | Condition | $k_{cat}$ (1/s) | $K_m$ (μM) | $K_{cat}/K_m$ (1/s) |
|---|---|---|---|---|
| BMY1 | pH 7.4, 34° C. | 6.9 ± 0.4 | 76 ± 6 | 89.7 ± 7.4 |
| | pH 7.4, 37° C. | 6.0 ± 0.7 | 67 ± 1 | 88.6 ± 2.5 |
| | pH 7.4, 40° C. | 9.1 ± 0.8 | 342 ± 67 | 26.5 ± 5.2 |
| | pH 6.0, 37° C. | 5.7 ± 0.8 | 158 ± 17 | 36.15 ± 3.9 |
| | pH 6.5, 37° C. | 11.8 ± 0.4 | 399 ± 86 | 29.6 ± 6.4 |
| | pH 8.0, 37° C. | 5.6 ± 0.6 | 217 ± 67 | 25.6 ± 7.9 |
| TGG1 | pH 7.4, 34° C. | 6.9 ± 1.6 | 78 ± 8 | 88.2 ± 9.7 |
| | pH 7.4, 37° C. | 6.4 ± 1.1 | 71 ± 3 | 89.9 ± 4.2 |
| | pH 7.4, 40° C. | 6.5 ± 0.2 | 88 ± 9 | 73.7 ± 7.6 |
| | pH 6.0, 37° C. | 10.2 ± 0.6 | 361 ± 11 | 28.3 ± 0.9 |
| | pH 6.5, 37° C. | 8.6 ± 1.6 | 198 ± 20 | 43.7 ± 4.6 |
| | pH 8.0, 37° C. | 4.3 ± 0.7 | 137 ± 69 | 31.2 ± 15.7 |
| A6 | pH 7.4, 34° C. | 7.2 ± 1.3 | 47 ± 5 | 153.5 ± 18.1 |
| | pH 7.4, 37° C. | 5.2 ± 0.9 | 44 ± 4 | 118.3 ± 11.1 |
| | pH 7.4, 40° C. | 9.7 ± 1.3 | 189 ± 39 | 51.6 ± 10.7 |
| | pH 6.0, 37° C. | 6.6 ± 1.3 | 68 ± 2 | 96.3 ± 4.7 |
| | pH 6.5, 37° C. | 15.0 ± 1.5 | 187 ± 13 | 80.4 ± 5.6 |
| | pH 8.0, 37° C. | 9.3 ± 1.2 | 142 ± 22 | 65.4 ± 10.2 |
| C9 | pH 7.4, 34° C. | 11.2 ± 2.4 | 384 ± 28 | 29.1 ± 2.4 |
| | pH 7.4, 37° C. | 3.4 ± 0.6 | 38 ± 2 | 88.8 ± 5.6 |
| | pH 7.4, 40° C. | 9.0 ± 0.9 | 352 ± 68 | 25.6 ± 4.9 |
| | pH 6.0, 37° C. | 5.6 ± 0.8 | 439 ± 97 | 12.7 ± 2.8 |
| | pH 6.5, 37° C. | 9.0 ± 0.9 | 290 ± 31 | 31.1 ± 3.4 |
| | pH 8.0, 37° C. | 10.7 ± 1.3 | 842 ± 80 | 12.7 ± 1.2 |
| I1 | pH 7.4, 34° C. | 3.4 ± 0.7 | 49 ± 4 | 69.5 ± 6.3 |
| | pH 7.4, 37° C. | 15.0 ± 1.5 | 87 ± 7 | 173.2 ± 13.7 |
| | pH 7.4, 40° C. | 15.2 ± 1.5 | 87 ± 9 | 174.0 ± 15.2 |
| | pH 6.0, 37° C. | 6.6 ± 0.7 | 192 ± 40 | 41.1 ± 8.5 |
| | pH 6.5, 37° C. | 7.9 ± 1.1 | 183 ± 19 | 61.6 ± 6.5 |
| | pH 8.0, 37° C. | 6.6 ± 3.1 | 192 ± 17 | 96.4 ± 9.1 |
| Q5 | pH 7.4, 34° C. | 2.9 ± 1.4 | 225 ± 13 | 13.0 ± 1.3 |
| | pH 7.4, 37° C. | 2.1 ± 1.6 | 25 ± 7 | 82.7 ± 24.1 |
| | pH 7.4, 40° C. | 3.7 ± 1.6 | 49 ± 14 | 75.2 ± 22.2 |
| | pH 6.0, 37° C. | 4.6 ± 1.1 | 184 ± 15 | 25.3 ± 2.3 |
| | pH 6.5, 37° C. | 4.9 ± 1.2 | 127 ± 21 | 39.0 ± 6.8 |
| | pH 8.0, 37° C. | 2.8 ± 1.1 | 154 ± 24 | 18.4 ± 3.1 |
| Q9 | pH 7.4, 34° C. | 13.0 ± 3.5 | 1301 ± 280 | 10 ± 2.2 |
| | pH 7.4, 37° C. | 3.8 ± 1.5 | 130 ± 9 | 29.1 ± 3.9 |
| | pH 7.4, 40° C. | 12.8 ± 3.9 | 693 ± 23 | 18.5 ± 10.2 |
| | pH 6.0, 37° C. | 3.0 ± 0.6 | 111 ± 3 | 27.3 ± 10.4 |
| | pH 6.5, 37° C. | 7.8 ± 0.8 | 291 ± 5 | 26.9 ± 6.0 |
| | pH 8.0, 37° C. | 4.4 ± 1.0 | 473 ± 6 | 9.2 ± 1.3 |

TABLE 2

Table S2 Anti-cancer activity levels in various cancer cell lines treated separately with sulforaphane, allyl isothiocyanate (AITC) and myrosinase I1-converted AITC. NA represents unquantifiable values based on the experimental parameters (n = 3 independent experiments, each measurement performed in triplicates; mean ± s.d.).

| Type | Primary cells | Gastric | Colorectal | | Breast | |
|---|---|---|---|---|---|---|
| Table a. Various cell lines treated with L-sulforaphane | | | | | | |
| Cell line | SMC | AGS | LoVo | CT26 | HCT116 | MCF7 |
| GI 50 value (μM) | 375 ± 113 | 15 ± 3 | 23 ± 2 | 45 ± 3 | 30 ± 7 | 29 ± 3 |
| Complete inhibition (hour) | NA | <24 | <24 | <24 | <24 | <3 |
| Table b. Various cell lines treated with AITC | | | | | | |
| Cell line | SMC | AGS | LoVo | CT26 | HCT116 | MCF7 |
| GI 50 value (μM) | 589 ± 219 | 18 ± 1 | 74 ± 5 | 15 ± 4 | 116 ± 9 | 104 ± 17 |
| Complete inhibition (hour) | NA | <24 | <24 | <24 | <24 | <3 |
| Table c. Various cell lines treated with YebF-I1-converted AITC | | | | | | |
| Cell line | SMC | AGS | LoVo | CT26 | HCT116 | MCF7 |
| GI 50 value (μM) | NA | 26 ± 2 | 232 ± 18 | 46 ± 10 | 155 ± 32 | 139 ± 21 |
| Complete inhibition (hour) | NA | <24 | <24 | <24 | <24 | <24 |

Example 5

FIG. 29 is a flowchart demonstrating illustrative method of use. A method for colorectal cancer prevention comprising the steps of Administering 2901 *Escherichia coli* Nissle 1917 (EcN) reengineered to bind 2903 to the heparan sulfate proteoglycan (HSPG) on cancer cell surface and reengineered to secrete myrosinase for conversion of dietary-glucosinolate to sulforaphane and ingesting 2905 cruciferous vegetables adequate to initiate 2907 a therapeutic response against colorectal cancer.

Example 6

FIGS. 30-32 are genetic sequences utilized in a preferred embodiment of the claimed invention in both DNA and protein form. It will be clear to one skilled in the art that the selected linkers utilized are by illustration only and not by limitation. Fluorescent sequences may be omitted without detracting from the spirit and scope of the claimed invention as well.

In the description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments. Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus. Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

INDUSTRIAL APPLICABILITY

The claimed invention has industrial applicability in the biomedical arts. In particular, the claimed invention is directly relevant to the therapeutic administration of reengineered gut bacteria for mitigation of and therapeutic effects against colorectal cancer.

We claim:

1. A therapeutically enhanced probiotic organism comprising:
   a bacterial chassis genetically reengineered to bind to the heparan sulfate proteoglycan (HSPG) on a cancer cell surface and reengineered to secrete myrosinase for the conversion of dietary-glucosinolate to sulforaphane.

2. The therapeutically enhanced probiotic organism of claim 1 wherein the bacterial chassis is *Escherichia coli* Nissle 1917 (EcN).

3. The therapeutically enhanced probiotic organism of claim 2 wherein the bacterial chassis secretes myrosinase which inhibits growth and promotes apoptosis in cancer cells, resulting in colorectal tumor clearance.

4. The therapeutically enhanced probiotic organism of claim 3 wherein said therapeutically enhanced probiotic organism contains a genetic sequence for Myrosinase II secretion that is the polynucleotide of Seq ID No. 4.

5. The therapeutically enhanced probiotic organism of claim 3 wherein said therapeutically enhanced probiotic organism contains a genetic sequence for Myrosinase II secretion that has at least 80% sequence identity to the polynucleotide of Seq ID No. 4.

6. The therapeutically enhanced probiotic organism of claim 2 wherein said therapeutically enhanced probiotic organism contains a genetic sequence for Histone-like protein A (Hlp-A), wherein the probiotic organism expresses Hlp-A, and wherein the Hlp-A binds to HSPG on the surface of cancer cells.

7. The therapeutically enhanced probiotic organism of claim 6 wherein the genetic sequence for the Hlp-A has at least 80% sequence identity to the polynucleotide of Seq ID No. 5.

8. A method of treating colorectal cancer in a subject in need thereof, by administering to the subject (i) a therapeutically effective amount of the probiotic organism of claim 1 and (ii) a therapeutically effective amount of cruciferous vegetables comprising glucosinolate.

* * * * *

SEQUENCE LISTING

<160> NUMBER OF SEQ ID NOS: 7

<210> SEQ ID NO 1
<211> LENGTH: 3164
<212> TYPE: DNA
<213> ORGANISM: Artificial Sequence
<220> FEATURE:
<223> OTHER INFORMATION: Artificial sequece created by rational desisgn

<400> SEQUENCE: 1

| | | | | | |
|---|---|---|---|---|---|
| tttacggcta | gctcagtcct | aggtactatg | ctagcaaaaa | aaaagaggag | aaaaaaaaat | 60 |
| ggccgatcac | tgcggtctta | tctggccagc | gtccggtact | gtggaatctc | gttactggca | 120 |
| gtctacccgt | cgccatgaga | acggtctggt | aggtttactg | tggggtgctg | gcaccagcgc | 180 |
| attcctcagc | gtgcatgcag | atgctcgttg | gattgtctgt | gaagttgccg | ttgcagacat | 240 |
| catcagtctg | gaagagccgg | gtatggtgaa | gtttccgcgt | gccgaagtgg | ttcatgtcgg | 300 |
| cgaccgtatt | agcgcgtctc | acttcatttc | ggcacgtcag | gccgaccctg | cgtctacctc | 360 |
| aacttctacg | tccacgagta | cgctgactcc | aatgcctacg | gccattccga | cgccaatgcc | 420 |
| tgcggttgca | agcgtaacgc | tgccagtggc | agaacaggca | cgtcatgaag | tgtttgatgt | 480 |
| agcgtcggta | agcgctgctg | ccgcaccagt | caacactctg | ccagttacta | cgccgcagaa | 540 |
| tctgcagacc | gcaacttatg | gttctacgtt | gtccggcgac | aatcattctc | gtctgattgc | 600 |
| aggttatggt | tccaacgaga | ccgctggcaa | ccacagtgat | ctgattgggt | cctttggtac | 660 |
| catggcgaac | aaacaggatc | tgattgcgaa | agtggcggaa | gcgaccgaac | tgaccaaaaa | 720 |
| agatagcgcg | gcggcggtgg | atgcggtgtt | tagcgcgatt | gaaagttttc | tgagcgaagg | 780 |
| cgaaaaagtg | cagctgattg | gctttggcaa | ctttgaagtg | cgcgaacgcg | cggcgcgcaa | 840 |
| aggccgcaac | ccgcagaccg | cgcggaaat | taaaattgcg | gcgagcaaag | tgccggcgtt | 900 |
| taaagcgggc | aaagcgctga | agatgcggt | gaaataaaag | cttccaggca | tcaaataaaa | 960 |
| cgaaaggctc | agtcgaaaga | ctgggccttt | cgttttatct | gttgtttgtc | ggtgaacgct | 1020 |
| ctctactaga | gtcacactgg | ctcaccttcg | ggtgggcctt | tctgcgttta | taaaaaaact | 1080 |
| gacagctagc | tcagtcctag | gtataatgct | agcaaaaaaa | aagaggagaa | aaaaaatga | 1140 |
| aaaaagagg | ggcgttttta | gggctgttgt | tggtttctgc | ctgcgcatca | gttttcgctg | 1200 |
| ccaataatga | aaccagcaag | tcggtcactt | tcccaaagtg | tgaagacctg | gatgctgccg | 1260 |
| gaattgccgc | gagcgtaaaa | cgtgattatc | aacaaaatcg | cgtggcgcgt | tgggcagatg | 1320 |
| atcaaaaaat | tgtcggtcag | gccgatcccg | tggcttgggt | cagtttgcag | gacattcagg | 1380 |
| gtaaagatga | taaatggtca | gtaccgctaa | ccgtgcgtgg | taaaagtgcc | gatattcatt | 1440 |
| accaggtcag | cgtggactgc | aaagcgggaa | tggcggaata | tcagcggcgt | catatgatga | 1500 |
| gcatcccaaa | agctcattac | tctctggcaa | tcctggctgt | actgttcgtg | gtgtctaact | 1560 |
| cccagaacgt | atgcaacccg | gcctgcaagg | cgaaagaacc | attcaactgt | gacaacactc | 1620 |
| tgaccttcaa | ccagaccggc | ttcccgaaaa | actttacgtt | cggcgctgca | acctctgctt | 1680 |
| accagatcga | gggtgctgct | caccgtgcgc | tgaacgttg | ggattacttt | acccatcgtt | 1740 |
| atccggagaa | agtcccggac | cgtagctccg | gtgacctggc | ttgtgattcc | tatgacctgt | 1800 |
| ataaagatga | cgtgaaactg | ctgaaacgta | tgaacgtcca | agcataccgt | ctgtctatcg | 1860 |
| cttggagccg | tgttctgccg | aaaggccgtc | tgatcggtgg | tgtagacgaa | aatggtatta | 1920 |
| cctattacaa | caacctgatt | aacgaactga | agccaacgg | catcgaaccg | tacgttacca | 1980 |
| tcttccactg | ggatgtccca | caaacccctgg | aagacgaata | tggtggcttc | ctgtccccgc | 2040 |

```
gcatcgttga ggacttcacg aactttgcag aactgctgtt ccagcgtttt ggtgatcgtg    2100
ttaagttctg gatcaccctg aaccagccgt actccctggc cactaaaggt tacggtgacg    2160
gcagctatcc gcctggtcgt tgcaccgatt gtgaattcgg cggcgattct ggtaccgaac    2220
cgtacatcgt agcgcatcat cagctgctgg cgcatgctga aacggtttct ctgtaccgta    2280
aacgttacca aaaattccaa ggcggtaaaa tcggtactac cctgattggt cgttggttcc    2340
agccgctgaa ccagacctcc aatctggaca agctgcagc caaacgtgct tttgatttct    2400
tcgttggttg gttcctggat ccgctggtat acggtgagta ccgaaaatc atgaaagaaa    2460 tggtgggcga tcgcatgccg aagttcaccc cgcaagaatc tgatctggtg aaaggttctc    2520
tggacttcct gggcctgaac tattacgtca cccagtacgc gaccgatgcc cctccgtcca    2580
tcccgaccca gccgtctgct atcacggacc cgcgcgttac tctgggttac tatcgtaacg    2640
gcatcccgat tggtgttcag gcagcttcct tcgtttatta cccgactggc tttcgccaga    2700
tcctgaatca tatcaaggac aactataaaa cccgctgac ctatattact gaaaatggtg    2760
tggccgactt cggcaatctg accctggcga acgctctggc ggatattggc cgcatccaaa    2820
accattgttc ccatctgtct tgcctgaaat gtgcgattgc tgacggctgc aacgttggcg    2880
gttatttcgc ttggagcttt atggataatt atgagtttgg taacggctat accctgcgtt    2940
tcggtatgaa ctgggttaac tttaccaacc ctgcagaccg taagcagaaa gactccggca    3000
aatggtttag caaatttctg gctaaataac tcgagccagg catcaaataa aacgaaaggc    3060
tcagtcgaaa gactgggcct ttcgttttat ctgttgtttg tcggtgaacg ctctctacta    3120
gagtcacact ggctcacctt cgggtgggcc tttctgcgtt tata                    3164

<210> SEQ ID NO 2
<211> LENGTH: 879
<212> TYPE: DNA
<213> ORGANISM: Artificial Sequence
<220> FEATURE:
<223> OTHER INFORMATION: Artificial Sequence created by rational design

<400> SEQUENCE: 2
atggccgatc actgcggtct tatctggcca gcgtccggta ctgtggaatc tcgttactgg     60
cagtctaccc gtcgccatga gaacggtctg gtaggtttac tgtggggtgc tggcaccagc    120
gcattcctca gcgtgcatgc agatgctcgt tggattgtct gtgaagttgc cgttgcagac    180
atcatcagtc tggaagagcc gggtatggtg aagtttccgc gtgccgaagt ggttcatgtc    240
ggcgaccgta ttagcgcgtc tcacttcatt tcggcacgtc aggccgaccc tgcgtctacc    300
tcaacttcta cgtccacgag tacgctgact ccaatgccta cggccattcc gacgccaatg    360
cctgcggttg caagcgtaac gctgccagtg cagaacagg cacgtcatga agtgtttgat    420
gtagcgtcgg taagcgctgc tgccgcacca gtcaacactc tgccagttac tacgccgcag    480
aatctgcaga ccgcaactta tggttctacg ttgtccggcg acaatcattc tcgtctgatt    540
gcaggttatg gttccaacga gaccgctggc aaccacagtg atctgattgg gtccctttggt    600 accatggcga acaaacagga tctgattgcg aaagtggcgg aagcgaccga actgaccaaa    660
aaagatagcg cggcggcgt ggatgcgtg tttagcgcga ttgaaagttt ctgagcgaa    720 ggcgaaaaag tgcagctgat tggctttggc aactttgaag tgcgcgaacg cgcggcgcgc    780
aaaggccgca cccgcagac cggcgcggaa attaaaattg cggcgagcaa agtgccggcg    840
tttaaagcgg gcaaagcgct gaaagatgcg gtgaaataa                           879
```

<210> SEQ ID NO 3
<211> LENGTH: 1893
<212> TYPE: DNA
<213> ORGANISM: Artificial Sequence
<220> FEATURE:
<223> OTHER INFORMATION: Artificial sequence created by rational design

<400> SEQUENCE: 3

```
atgaaaaaaa gaggggcgtt tttagggctg ttgttggttt ctgcctgcgc atcagttttc      60
gctgccaata atgaaaccag caagtcggtc actttcccaa agtgtgaaga cctggatgct     120
gccggaattg ccgcgagcgt aaaacgtgat tatcaacaaa atcgcgtggc gcgttgggca     180
gatgatcaaa aaattgtcgg tcaggccgat cccgtggctt gggtcagttt gcaggacatt     240
cagggtaaag atgataaatg gtcagtaccg ctaaccgtgc gtggtaaaag tgccgatatt     300
cattaccagg tcagcgtgga ctgcaaagcg ggaatggcgg aatatcagcg cgtcatatg     360
atgagcatcc aaaagctca ttactctctg gcaatcctgg ctgtactgtt cgtggtgtct     420
aactcccaga acgtatgcaa cccggcctgc aaggcgaaag aaccattcaa ctgtgacaac     480
actctgacct caaccagac cggcttcccg aaaaacttta cgttcggcgc tgcaacctct     540
gcttaccaga tcgagggtgc tgctcaccgt gcgctgaacg gttgggatta ctttacccat     600
cgttatccgg agaaagtccc ggaccgtagc tccggtgacc tggcttgtga ttcctatgac     660
ctgtataaag atgacgtgaa actgctgaaa cgtatgaact ccaagcata ccgtctgtct     720
atcgcttgga gccgtgttct gccgaaaggc cgtctgatcg gtggtgtaga cgaaaatggt     780
attacctatt acaacaacct gattaacgaa ctgaaagcca acggcatcga accgtacgtt     840
accatcttcc actgggatgt cccacaaacc ctggaagacg aatatggtgg cttcctgtcc     900
ccgcgcatcg ttgaggactt cacgaacttt gcagaactgc tgttccagcg ttttggtgat     960
cgtgttaagt tctggatcac cctgaaccag ccgtactccc tggccactaa aggttacggt    1020
gacggcagct atccgcctgg tcgttgcacc gattgtgaat cggcggcga ttctggtacc    1080
gaaccgtaca tcgtagcgca tcatcagctg ctggcgcatg ctgaaacggt ttctctgtac    1140
cgtaaacgtt accaaaaatt ccaaggcggt aaaatcggta ctaccctgat ggtcgttgg    1200
ttccagccgc tgaaccagac ctccaatctg gacaaagctg cagccaaacg tgcttttgat    1260
ttcttcgttg gttggttcct ggatccgctg gtatacggtg agtatccgaa atcatgaaa    1320
gaaatggtgg gcgatcgcat gccgaagttc accccgcaag aatctgatct ggtgaaaggt    1380
tctctggact tcctgggcct gaactattac gtcacccagt acgcgaccga tgcccctccg    1440
tccatcccga cccagccgtc tgctatcacg gacccgcgcg ttactctggg ttactatcgt    1500
aacggcatcc cgattggtgt tcaggcagct tccttcgttt attacccgac tggctttcgc    1560
cagatcctga atcatatcaa ggacaactat aaaaacccgc tgacctatat tactgaaaat    1620
ggtgtggccg acttcggcaa tctgacgct gcgaacgctc tggcggatat ggccgcatc    1680
caaaaccatt gttcccatct gtcttgcctg aaatgtgcga ttgctgacgg ctgcaacgtt    1740
ggcggttatt tcgcttggag ctttatggat aattatgagt ttggtaacgg ctataccctg    1800
cgtttcggta tgaactgggt taactttacc aaccctgcag accgtaagca gaaagactcc    1860
ggcaaatggt ttagcaaatt tctggctaaa taa                                 1893
```

<210> SEQ ID NO 4
<211> LENGTH: 1533
<212> TYPE: DNA
<213> ORGANISM: Armoracia rusticana (I1)

<400> SEQUENCE: 4

```
atgagcatcc caaaagctca ttactctctg caatcctggg ctgtactgtt cgtggtgtct      60
aactcccaga acgtatgcaa cccggcctgc aaggcgaaag aaccattcaa ctgtgacaac     120
actctgacct tcaaccagac cggcttcccg aaaaacttta cgttcggcgc tgcaacctct     180
gcttaccaga tcgagggtgc tgctcaccgt gcgctgaacg gttgggatta ctttacccat     240
cgttatccgg agaaagtccc ggaccgtagc tccggtgacc tggcttgtga ttcctatgac     300
ctgtataaag atgacgtgaa actgctgaaa cgtatgaacg tccaagcata ccgtctgtct     360
atcgcttgga ccgtgttctg ccgaaaggc cgtctgatcg tggtgtaga cgaaaatggt      420
attacctatt acaacaacct gattaacgaa ctgaaagcca acggcatcga accgtacgtt     480
accatcttcc actgggatgt cccacaaacc ctggaagaca atatggtgg cttcctgtcc      540
ccgcgcatcg ttgaggactt cacgaacttt gcagaactgc tgttccagcg ttttggtgat     600
cgtgttaagt tctggatcac cctgaaccag ccgtactccc tggccactaa aggttacggt     660
gacggcagct atccgcctgg tcgttgcacc gattgtgaat cggcggcga ttctggtacc      720
gaaccgtaca tcgtagcgca tcatcagctg ctggcgcatg ctgaaacggt ttctctgtac     780
cgtaaacgtt accaaaaatt ccaaggcggt aaaatcggta ctaccctgat tggtcgttgg    840
ttccagccgc tgaaccagac ctccaatctg acaaagctg cagccaaacg tgcttttgat      900
ttcttcgttg gttggttcct ggatccgctg gtatacggtg agtatccgaa aatcatgaaa     960
gaaatggtgg gcgatcgcat gccgaagttc accccgcaag aatctgatct ggtgaaaggt    1020
tctctggact tcctgggcct gaactattac gtcacccagt acgcgaccga tgccctccg    1080
tccatcccga cccagccgtc tgctatcacg gacccgcgcg ttactctggg ttactatcgt    1140
aacggcatcc cgattggtgt tcaggcagct tccttcgttt attacccgac tggctttcgc    1200
cagatcctga atcatatcaa ggacaactat aaaaacccgc tgacctatat tactgaaaat    1260
ggtgtggccg acttcggcaa tctgacccctg gcgaacgctc tggcggatat tggccgcatc    1320
caaaaccatt gttcccatct gtcttgcctg aaatgtgcga ttgctgacgg ctgcaacgtt    1380
ggcggttatt tcgcttggag cttatggat aattatgagt ttggtaacgg ctataccctg     1440
cgtttcggta tgaactgggt taactttacc aaccctgcag accgtaagca gaaagactcc    1500
ggcaaatggt ttagcaaatt tctggctaaa taa                                 1533
```

<210> SEQ ID NO 5
<211> LENGTH: 276
<212> TYPE: DNA
<213> ORGANISM: Streptococcus gallolyticus

<400> SEQUENCE: 5

```
atggcgaaca aacaggatct gattgcgaaa gtggcggaag cgaccgaact gaccaaaaaa      60
gatagcgcgg cggcggtgga tgcggtgttt agcgcgattg aaagttttct gagcgaaggc     120
gaaaaagtgc agctgattgg ctttggcaac tttgaagtgc gcgaacgcgc ggcgcgcaaa     180
ggccgcaacc cgcagaccgg cgcggaaatt aaaattgcgg cgagcaaagt gccggcgttt     240
aaagcgggca agcgctgaa agatgcggtg aaataa                               276
```

<210> SEQ ID NO 6
<211> LENGTH: 510
<212> TYPE: PRT
<213> ORGANISM: Armoracia rusticana (I1)

<400> SEQUENCE: 6

```
Met Ser Ile Pro Lys Ala His Tyr Ser Leu Ala Ile Leu Ala Val Leu
1               5                   10                  15

Phe Val Val Ser Asn Ser Gln Asn Val Cys Asn Pro Ala Cys Lys Ala
            20                  25                  30

Lys Glu Pro Phe Asn Cys Asp Asn Thr Leu Thr Phe Asn Gln Thr Gly
        35                  40                  45

Phe Pro Lys Asn Phe Thr Phe Gly Ala Ala Thr Ser Ala Tyr Gln Ile
    50                  55                  60

Glu Gly Ala Ala His Arg Ala Leu Asn Gly Trp Asp Tyr Phe Thr His
65                  70                  75                  80

Arg Tyr Pro Glu Lys Val Pro Asp Arg Ser Ser Gly Asp Leu Ala Cys
                85                  90                  95

Asp Ser Tyr Asp Leu Tyr Lys Asp Val Lys Leu Leu Lys Arg Met
            100                 105                 110

Asn Val Gln Ala Tyr Arg Leu Ser Ile Ala Trp Ser Arg Val Leu Pro
        115                 120                 125

Lys Gly Arg Leu Ile Gly Val Asp Glu Asn Gly Ile Thr Tyr Tyr
    130                 135                 140

Asn Asn Leu Ile Asn Glu Leu Lys Ala Asn Gly Ile Glu Pro Tyr Val
145                 150                 155                 160

Thr Ile Phe His Trp Asp Val Pro Gln Thr Leu Glu Asp Glu Tyr Gly
                165                 170                 175

Gly Phe Leu Ser Pro Arg Ile Val Glu Asp Phe Thr Asn Phe Ala Glu
            180                 185                 190

Leu Leu Phe Gln Arg Phe Gly Asp Arg Val Lys Phe Trp Ile Thr Leu
        195                 200                 205

Asn Gln Pro Tyr Ser Leu Ala Thr Lys Gly Tyr Gly Asp Gly Ser Tyr
    210                 215                 220

Pro Pro Gly Arg Cys Thr Asp Cys Glu Phe Gly Gly Asp Ser Gly Thr
225                 230                 235                 240

Glu Pro Tyr Ile Val Ala His His Gln Leu Leu Ala His Ala Glu Thr
                245                 250                 255

Val Ser Leu Tyr Arg Lys Arg Tyr Gln Lys Phe Gln Gly Gly Lys Ile
            260                 265                 270

Gly Thr Thr Leu Ile Gly Arg Trp Phe Gln Pro Leu Asn Gln Thr Ser
        275                 280                 285

Asn Leu Asp Lys Ala Ala Lys Arg Ala Phe Asp Phe Val Gly
    290                 295                 300

Trp Phe Leu Asp Pro Leu Val Tyr Gly Glu Tyr Pro Lys Ile Met Lys
305                 310                 315                 320

Glu Met Val Gly Asp Arg Met Pro Lys Phe Thr Pro Gln Glu Ser Asp
                325                 330                 335

Leu Val Lys Gly Ser Leu Asp Phe Leu Gly Leu Asn Tyr Tyr Val Thr
            340                 345                 350

Gln Tyr Ala Thr Asp Ala Pro Pro Ser Ile Pro Thr Gln Pro Ser Ala
        355                 360                 365

Ile Thr Asp Pro Arg Val Thr Leu Gly Tyr Tyr Arg Asn Gly Ile Pro
    370                 375                 380

Ile Gly Val Gln Ala Ala Ser Phe Val Tyr Pro Thr Gly Phe Arg
385                 390                 395                 400

Gln Ile Leu Asn His Ile Lys Asp Asn Tyr Lys Asn Pro Leu Thr Tyr
                405                 410                 415
```

```
Ile Thr Glu Asn Gly Val Ala Asp Phe Gly Asn Leu Thr Leu Ala Asn
            420                 425                 430

Ala Leu Ala Asp Ile Gly Arg Ile Gln Asn His Cys Ser His Leu Ser
            435                 440                 445

Cys Leu Lys Cys Ala Ile Ala Asp Gly Cys Asn Val Gly Gly Tyr Phe
            450                 455                 460

Ala Trp Ser Phe Met Asp Asn Tyr Glu Phe Gly Asn Gly Tyr Thr Leu
465                 470                 475                 480

Arg Phe Gly Met Asn Trp Val Asn Phe Thr Asn Pro Ala Asp Arg Lys
                485                 490                 495

Gln Lys Asp Ser Gly Lys Trp Phe Ser Lys Phe Leu Ala Lys
            500                 505                 510

<210> SEQ ID NO 7
<211> LENGTH: 91
<212> TYPE: PRT
<213> ORGANISM: Streptococcus gallolyticus

<400> SEQUENCE: 7

Met Ala Asn Lys Gln Asp Leu Ile Ala Lys Val Ala Glu Ala Thr Glu
1               5                   10                  15

Leu Thr Lys Lys Asp Ser Ala Ala Val Asp Ala Val Phe Ser Ala
                20                  25                  30

Ile Glu Ser Phe Leu Ser Glu Gly Glu Lys Val Gln Leu Ile Gly Phe
            35                  40                  45

Gly Asn Phe Glu Val Arg Glu Arg Ala Ala Arg Lys Gly Arg Asn Pro
    50                  55                  60

Gln Thr Gly Ala Glu Ile Lys Ile Ala Ala Ser Lys Val Pro Ala Phe
65                  70                  75                  80

Lys Ala Gly Lys Ala Leu Lys Asp Ala Val Lys
                85                  90
```